(12) United States Patent
Kano et al.

(10) Patent No.: US 11,094,417 B2
(45) Date of Patent: Aug. 17, 2021

(54) MEDICAL INFORMATION PROCESSING APPARATUS AND MEDICAL INFORMATION PROCESSING METHOD

(71) Applicant: CANON MEDICAL SYSTEMS CORPORATION, Otawara (JP)

(72) Inventors: Yusuke Kano, Nasushiobara (JP); Kazuki Utsunomiya, Nasushiobara (JP); Shinya Sugiyama, Nasushiobara (JP); Longxun Piao, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 106 days.

(21) Appl. No.: 16/163,053

(22) Filed: Oct. 17, 2018

(65) Prior Publication Data

US 2019/0051412 A1 Feb. 14, 2019

Related U.S. Application Data

(63) Continuation of application No. PCT/JP2018/013976, filed on Mar. 30, 2018.

(30) Foreign Application Priority Data

Mar. 31, 2017 (JP) .............................. JP2017-070998

(51) Int. Cl.
*G16H 50/20* (2018.01)
*G16H 10/60* (2018.01)
(Continued)

(52) U.S. Cl.
CPC ............... *G16H 50/20* (2018.01); *G06F 3/14* (2013.01); *G16H 10/60* (2018.01); *G16H 15/00* (2018.01); *G16H 30/20* (2018.01); *G16H 40/63* (2018.01)

(58) Field of Classification Search
CPC ........ G16H 50/20; G16H 10/60; G16H 15/00; G16H 30/20; G16H 40/63; G06F 3/14
See application file for complete search history.

(56) References Cited

U.S. PATENT DOCUMENTS

| | | | | |
|---|---|---|---|---|
| 5,724,128 A | * | 3/1998 | January ............... | G01B 11/275 33/203.18 |
| 2004/0013292 A1 | * | 1/2004 | Raunig ................. | G06T 7/0012 382/128 |

(Continued)

FOREIGN PATENT DOCUMENTS

| | | |
|---|---|---|
| JP | 2004-178435 | 6/2004 |
| JP | 2010-205045 | 9/2010 |

(Continued)

OTHER PUBLICATIONS

International Search Report dated May 22, 2018 in PCT/JP2018/013976, filed on Mar. 30, 2018 (with English Translation).

(Continued)

*Primary Examiner* — Abderrahim Merouan
(74) *Attorney, Agent, or Firm* — Oblon, McClelland, Maier & Neustadt, L.L.P.

(57) ABSTRACT

A medical information processing apparatus according to an embodiment includes processing circuitry. The processing circuitry is configured to display medical examination data on the basis of a medical examination data space having a dimension corresponding to a data display format determined for each piece of medical examination data. The processing circuitry is configured to perform space conversion with reference to a specified conversion reference point in the medical examination data space to switch display of the medical examination data that is displayed.

17 Claims, 49 Drawing Sheets

(51) Int. Cl.
*G16H 15/00* (2018.01)
*G16H 30/20* (2018.01)
*G06F 3/14* (2006.01)
*G16H 40/63* (2018.01)

(56) References Cited

U.S. PATENT DOCUMENTS

| | | | | |
|---|---|---|---|---|
| 2005/0234670 A1* | 10/2005 | Hagen | ............... | G06T 11/206 702/85 |
| 2006/0012596 A1* | 1/2006 | Fukuya | ............... | G11B 27/034 345/419 |
| 2007/0276224 A1* | 11/2007 | Lang | ............... | A61B 5/1038 600/410 |
| 2010/0121201 A1* | 5/2010 | Papaioannou | ............... | A61B 5/445 600/477 |
| 2012/0002844 A1* | 1/2012 | Ikeda | ............... | G16B 45/00 382/106 |
| 2013/0088512 A1* | 4/2013 | Suzuki | ............... | A61B 6/463 345/629 |
| 2013/0111416 A1* | 5/2013 | Nakagawa | ............... | G03F 1/70 716/51 |
| 2013/0208955 A1* | 8/2013 | Zhao | ............... | G06F 19/321 382/128 |
| 2013/0290024 A1* | 10/2013 | Kawanaka | ............... | G16H 10/60 705/3 |
| 2014/0310584 A1* | 10/2014 | Tanaka | ............... | G16H 15/00 715/227 |
| 2015/0317452 A1* | 11/2015 | Kozuka | ............... | G16H 15/00 705/2 |
| 2017/0024516 A1 | 1/2017 | Okabe et al. | | |
| 2017/0230632 A1* | 8/2017 | Okabe | ............... | A61B 5/743 |
| 2017/0319184 A1* | 11/2017 | Sano | ............... | A61B 5/742 |

FOREIGN PATENT DOCUMENTS

JP 2017-27266 2/2017
WO WO-2016080066 A1 * 5/2016 ........... A61B 5/7435

OTHER PUBLICATIONS

Written Opinion dated May 22, 2018 in PCT/JP2018/013976, filed on Mar. 30, 2018.

* cited by examiner

FIG.3

| MEDICATION ID | DATE AND TIME | DATA |
|---|---|---|
| Med0001 | 2017/02/10_09:00 | MEDICINE (1) |
| Med0002 | 2017/02/10_13:00 | MEDICINE (1) |
| Med0003 | 2017/02/10_17:00 | MEDICINE (1) |
| Med0004 | 2017/02/11_09:00 | MEDICINE (1) |
| Med0005 | 2017/02/11_13:00 | MEDICINE (1) |
| ... | ... | ... |

FIG.4

| MEDICATION SUMMARY ID | ORDER ID |
|---|---|
| MedSum0001 | Med0001, Med0002, ... |
| MedSum0002 | Med0010, Med0011, ... |
| MedSum0003 | Med0060, Med0061, ... |
| MedSum0004 | Med0155, Med0156, ... |
| MedSum0005 | Med0232, Med0233, ... |
| ... | ... |

FIG.5

| IMAGE ID | DATE AND TIME | DATA |
|---|---|---|
| Img0001 | 2017/02/10_10:20 | 20170210_1020.dcm |
| Img0002 | 2017/02/11_08:50 | 20170211_0850.dcm |
| Img0003 | 2017/02/12_13:53 | 20170212_1353.dcm |
| Img0004 | 2017/02/13_15:10 | 20170213_1510.dcm |
| Img0005 | 2017/02/13_17:34 | 20170213_1734.dcm |
| … | … | … |

FIG.6

| MEASUREMENT VALUE ID | IMAGE ID | MEASUREMENT TYPE | DATA |
|---|---|---|---|
| ImgMes0001 | Img0001 | TUMOR DIAMETER | 10 mm |
| ImgMes0002 | Img0001 | BLOOD VESSEL DIAMETER | 5 mm |
| ImgMes0003 | Img0002 | TUMOR DIAMETER | 23 mm |
| ImgMes0004 | Img0003 | TUMOR DIAMETER | 12 mm |
| ImgMes0005 | Img0003 | FLOW RATE | 200 ml/min |
| … | … | … | … |

FIG.7

| IMAGE READING REPORT ID | IMAGE ID | REPORT |
|---|---|---|
| ImgRep0001 | Img0001 | REPORT 0001.doc |
| ImgRep0002 | Img0002 | REPORT 0002.doc |
| ImgRep0003 | Img0003 | REPORT 0003.doc |
| ImgRep0004 | Img0004 | REPORT 0004.doc |
| ImgRep0005 | Img0005 | REPORT 0005.doc |
| ... | ... | ... |

FIG.8

| ELECTROCARDIOGRAM ID | DATE AND TIME | DATA |
|---|---|---|
| Ecd0001 | 2017/02/10_09:30 | 20170210_0930.png |
| Ecd0002 | 2017/02/11_08:30 | 20170211_0830.png |
| Ecd0003 | 2017/02/12_12:30 | 20170212_1230.png |
| Ecd0004 | 2017/02/13_14:30 | 20170213_1430.png |
| Ecd0005 | 2017/02/13_16:30 | 20170213_1630.png |
| ... | ... | ... |

FIG.9

| MEASUREMENT VALUE ID | ELECTROCARDIOGRAM ID | MEASUREMENT TYPE | DATA |
|---|---|---|---|
| EcdMes0001 | Ecd0001 | HEART RATE | 63 |
| EcdMes0002 | Ecd0001 | P-WAVE LEVEL | 0.25 mV |
| EcdMes0003 | Ecd0001 | P-WAVE WIDTH | 0.08 sec |
| EcdMes0004 | Ecd0002 | HEART RATE | 75 |
| EcdMes0005 | Ecd0003 | HEART RATE | 57 |
| ... | ... | ... | ... |

FIG.10

| ELECTROCARDIOGRAM REPORT ID | ELECTROCARDIOGRAM ID | REPORT |
|---|---|---|
| EcdRep0001 | Ecd0001 | REPORT 1001.doc |
| EcdRep0002 | Ecd0002 | REPORT 1002.doc |
| EcdRep0003 | Ecd0003 | REPORT 1003.doc |
| EcdRep0004 | Ecd0004 | REPORT 1004.doc |
| EcdRep0005 | Ecd0005 | REPORT 1005.doc |
| ... | ... | ... |

FIG.11

| VITAL ID | DATE AND TIME | DATA |
| --- | --- | --- |
| Vit0001 | 2017/02/10_09:30 | BLOOD PRESSURE: 141/83, PULSE: 63, BODY TEMPERATURE: 36.5 |
| Vit0002 | 2017/02/11_08:30 | BLOOD PRESSURE: 145/80, PULSE: 75, BODY TEMPERATURE: 37.1 |
| Vit0003 | 2017/02/12_12:30 | BLOOD PRESSURE: 135/76, PULSE: 57, BODY TEMPERATURE: 35.6 |
| Vit0004 | 2017/02/13_14:30 | BLOOD PRESSURE: 153/95, PULSE: 56, BODY TEMPERATURE: 36.7 |
| Vit0005 | 2017/02/13_16:30 | BLOOD PRESSURE: 137/87, PULSE: 62, BODY TEMPERATURE: 36.8 |
| ... | ... | ... |

FIG.12

| VITAL SUMMARY ID | VITAL ID |
| --- | --- |
| VitSum0001 | Vit0001, Vit0002, ... |
| VitSum0002 | Vit0023, Vit0024, ... |
| VitSum0003 | Vit0125, Vit0126, ... |
| VitSum0004 | Vit0264, Vit0265, ... |
| VitSum0005 | Vit0486, Vit0487, ... |
| ... | ... |

FIG.13

| NURSING RECORD ID | VITAL ID | REPORT |
|---|---|---|
| VitRep0001 | Vit0001 | REPORT 3001.doc |
| VitRep0002 | Vit0002 | REPORT 3002.doc |
| VitRep0003 | Vit0003 | REPORT 3003.doc |
| VitRep0004 | Vit0004 | REPORT 3004.doc |
| VitRep0005 | Vit0005 | REPORT 3005.doc |
| ... | ... | ... |

FIG.14

| SPECIMEN INSPECTION ID | DATE AND TIME | DATA |
|---|---|---|
| Lab0001 | 2017/02/10_09:45 | TP: 6.7 g/dl, UA: 4.5 mg/dl, ... |
| Lab0002 | 2017/02/11_08:45 | TP: 6.9 g/dl, UA: 4.6 mg/dl, ... |
| Lab0003 | 2017/02/12_12:45 | TP: 6.3 g/dl, UA: 4.7 mg/dl, ... |
| Lab0004 | 2017/02/13_14:45 | TP: 6.0 g/dl, UA: 4.6 mg/dl, ... |
| Lab0005 | 2017/02/13_16:45 | TP: 6.4 g/dl, UA: 4.9 mg/dl, ... |
| ... | ... | ... |

FIG.15

| SPECIMEN INSPECTION SUMMARY ID | SPECIMEN INSPECTION ID |
|---|---|
| LabSum0001 | Lab0001, Lab0002, ⋯ |
| LabSum0002 | Lab0012, Lab0013, ⋯ |
| LabSum0003 | Lab0043, Lab0044, ⋯ |
| LabSum0004 | Lab0051, Lab0052, ⋯ |
| LabSum0005 | Lab0060, Lab0061, ⋯ |
| ⋯ | ⋯ |

FIG.16

| SPECIMEN INSPECTION REPORT ID | SPECIMEN INSPECTION ID | REPORT |
|---|---|---|
| LabRep0001 | Lab0001 | REPORT 5001.doc |
| LabRep0002 | Lab0002 | REPORT 5002.doc |
| LabRep0003 | Lab0003 | REPORT 5003.doc |
| LabRep0004 | Lab0004 | REPORT 5004.doc |
| LabRep0005 | Lab0005 | REPORT 5005.doc |
| ⋯ | ⋯ | ⋯ |

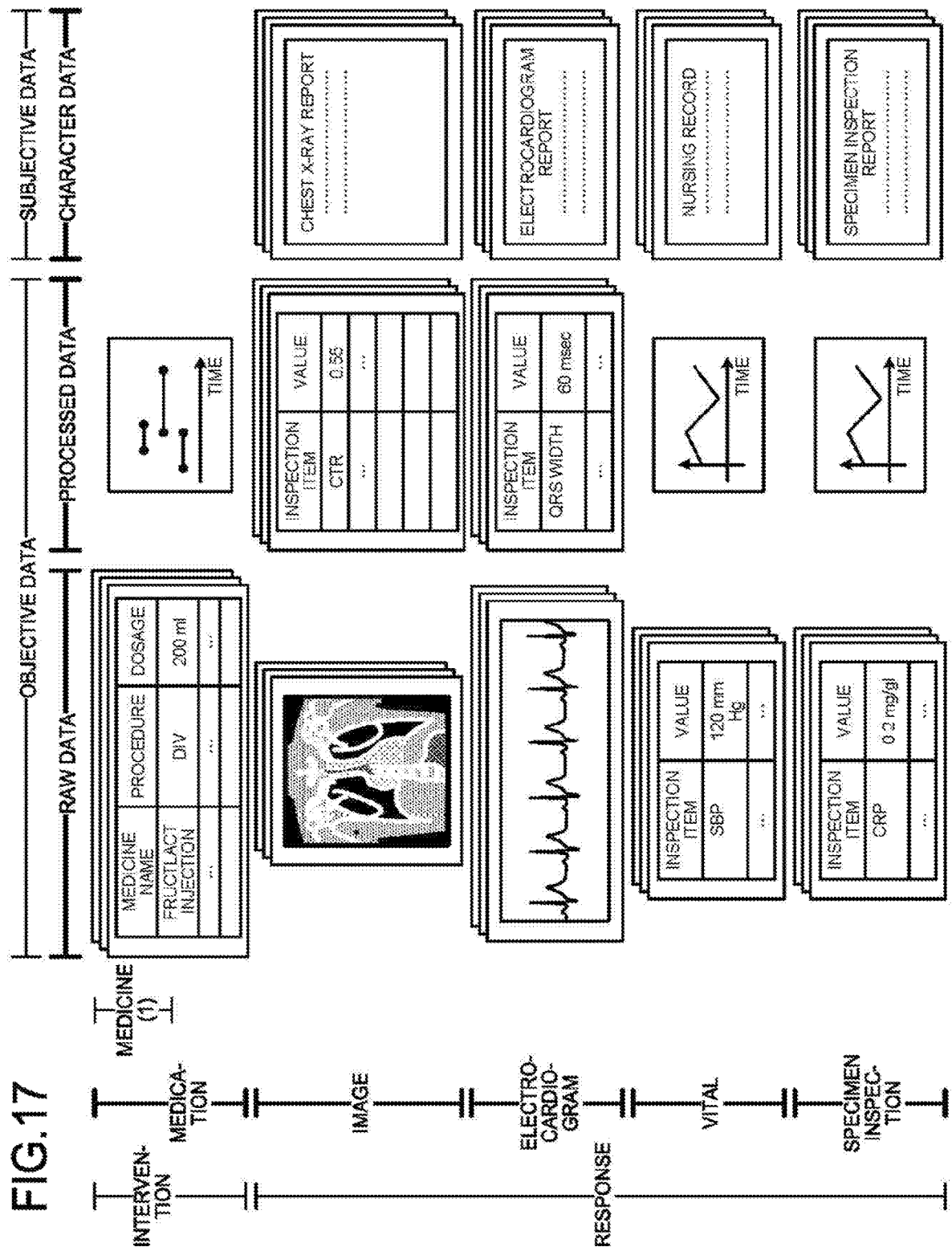

FIG.18

| PANEL ID | PANEL |
|---|---|
| Panel0001 | TABLE FORMAT PANEL |
| Panel0002 | TIME-SERIES FORMAT PANEL |
| Panel0003 | IMAGE DISPLAY PANEL |
| Panel0004 | ELECTROCARDIOGRAM DISPLAY PANEL |
| Panel0005 | REPORT DISPLAY PANEL |
| ... | ... |

FIG.19

| DATA DISPLAY ID | PANEL ID | DATA ID |
|---|---|---|
| DView0001 | Panel0001 | Med0001 |
| DView0002 | Panel0003 | Img0001 |
| DView0003 | Panel0001 | ImgMes0001, ImgMes0002, ... |
| DView0004 | Panel0004 | Ecd0001 |
| DView0005 | Panel0001 | Vit0001 |
| DView0006 | Panel0001 | Lab0001 |
| DView0007 | Panel0002 | MedSum0001 |
| DView0008 | Panel0002 | VitSum0001 |
| DView0009 | Panel0002 | LabSum0001 |
| DView0010 | Panel0005 | ImgRep0001 |
| ... | ... | ... |

FIG.20

| COORDINATE ID | DATA DISPLAY ID | Width | Time | Depth |
|---|---|---|---|---|
| Coor0001 | DView0001 | 1 | 1 | 1 |
| Coor0002 | DView0002 | 2 | 1 | 1 |
| Coor0003 | DView0003 | 2 | 1 | 2 |
| Coor0004 | DView0004 | 3 | 1 | 1 |
| Coor0005 | DView0005 | 4 | 1 | 1 |
| Coor0006 | DView0006 | 5 | 1 | 1 |
| Coor0007 | DView0007 | 1 | 1, 2, 3 | 2 |
| Coor0008 | DView0008 | 4 | 2 TO 6 | 2 |
| Coor0009 | DView0009 | 5 | * | 2 |
| Coor0010 | DView0010 | 2 | 1 | 3 |
| ... | ... | ... | ... | ... |

FIG.25

CASE OF (W, T, D) = (2, 1, 2)

| INSPECTION ITEM | VALUE |
|---|---|
| CTR | 0.55 |
| ... | ... |
|  |  |
|  |  |
|  |  |

CASE OF (W, T, D) = (2, 1, 3)

CHEST X-RAY REPORT

3

FIG.40
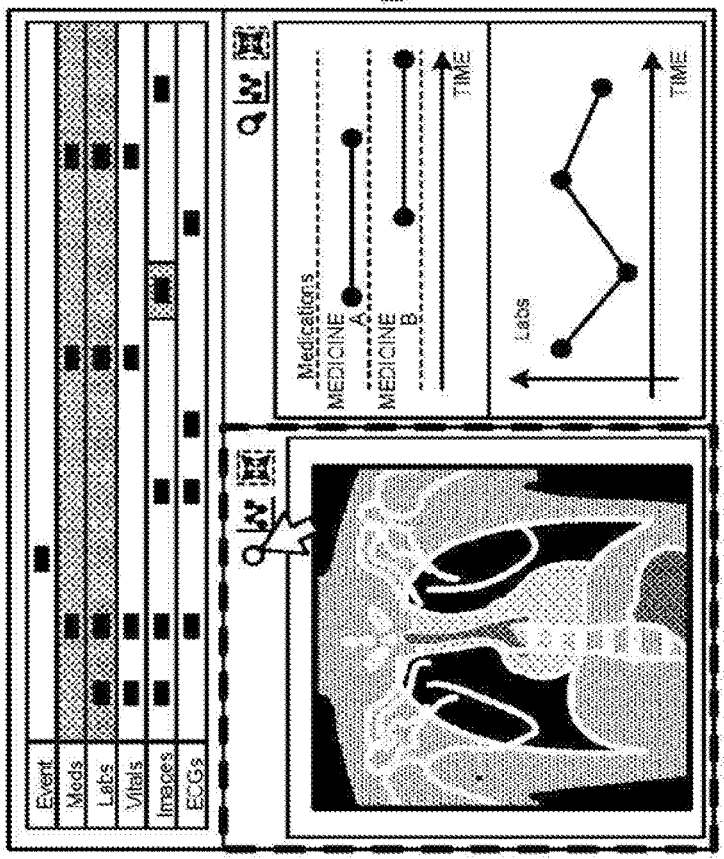
$(W, T, D) = (W_A, T_A, D_A)$
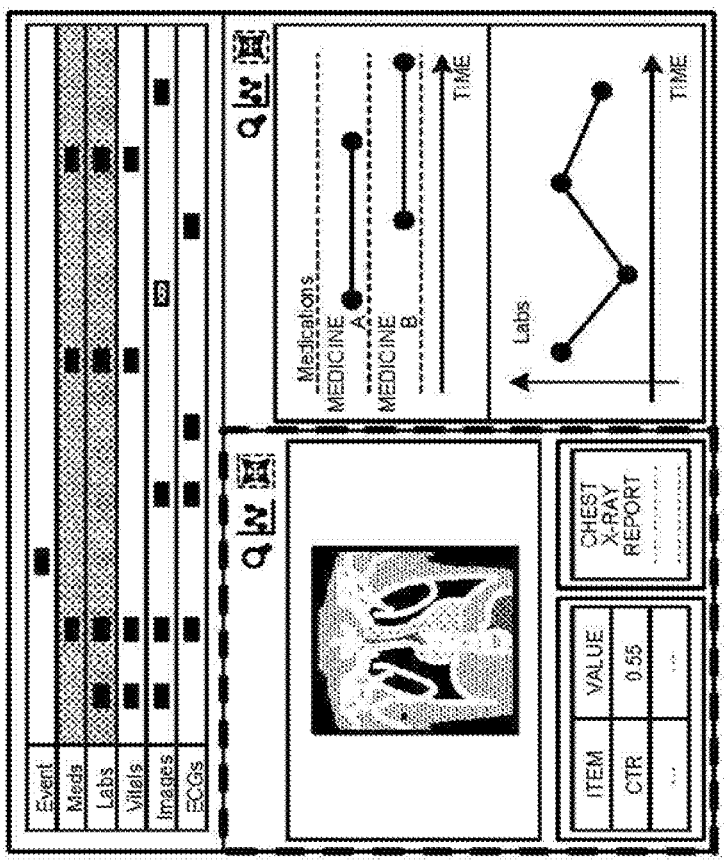
$(W, T, D) = (W_A, T_A, *)$ FIG.41
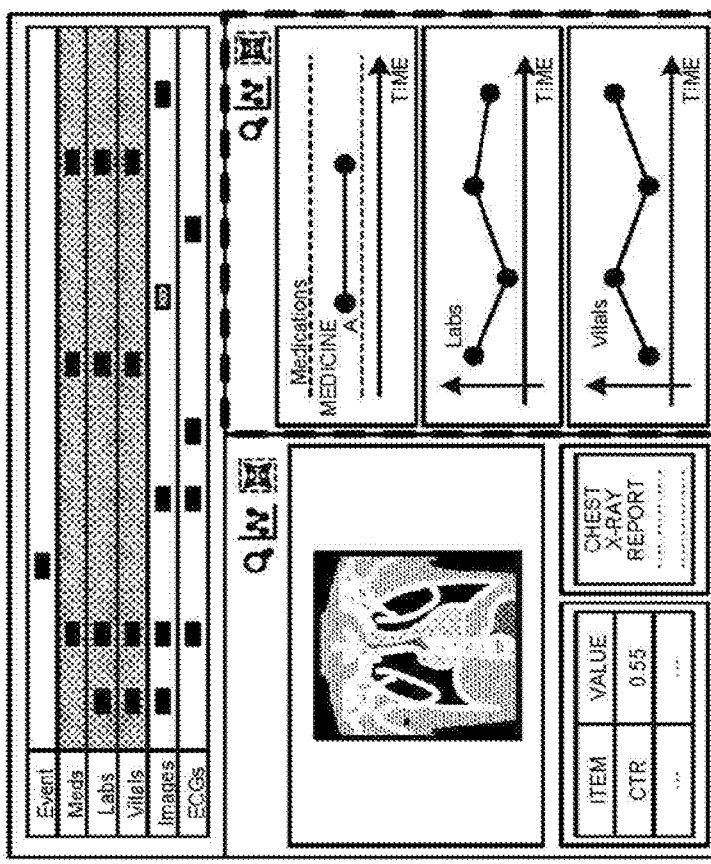
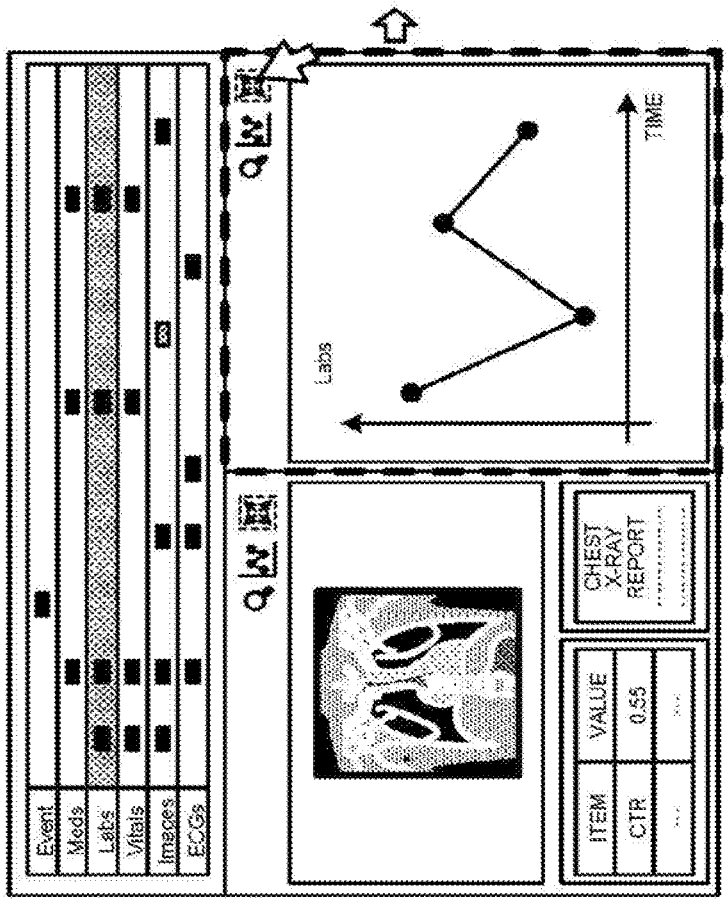

FIG.51

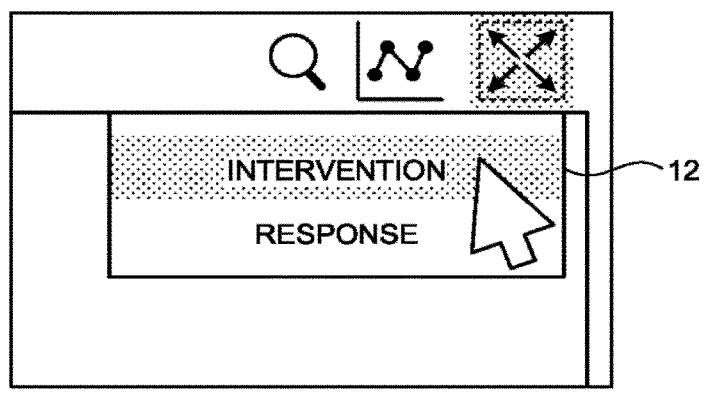

FIG.52

| MAPPING ID | NAME | TABLE |
|---|---|---|
| Map0001 | MEDICATION | MEDICATION (1) TABLE, MEDICATION (2) TABLE, MEDICATION (3) TABLE, ··· |
| Map0002 | INTERVENTION | MEDICATION TABLE, MEAL TABLE, ··· |
| Map0003 | RESPONSE | IMAGE TABLE, ELECTROCARDIOGRAM TABLE, VITAL TABLE, ··· |
| Map0004 | OBJECTIVE DATA | MEDICATION TABLE, MEDICATION SUMMARY TABLE, ··· |
| Map0005 | SUBJECTIVE DATA | IMAGE READING REPORT TABLE, ELECTROCARDIOGRAM REPORT TABLE, ··· |
| ··· | ··· | ··· |

FIG.54

| COORDINATE ID | DATA DISPLAY ID | LARGE WIDTH | SMALL WIDTH | TIME | DEPTH |
|---|---|---|---|---|---|
| Coor0001 | DView0001 | 1 | 1 | 1 | 1 |
| Coor0002 | DView0002 | 2 | 2 | 1 | 1 |
| Coor0003 | DView0003 | 2 | 2 | 1 | 2 |
| Coor0004 | DView0004 | 2 | 3 | 1 | 1 |
| Coor0005 | DView0005 | 2 | 4 | 1 | 1 |
| Coor0006 | DView0006 | 2 | 5 | 1 | 1 |
| Coor0007 | DView0007 | 1 | 1 | 1, 2, 3 | 2 |
| Coor0008 | DView0008 | 2 | 4 | 2 TO 6 | 2 |
| Coor0009 | DView0009 | 2 | 5 | * | 2 |
| Coor0010 | DView0010 | 2 | 2 | 1 | 3 |
| ... | ... | ... | ... | ... | ... |

FIG.57
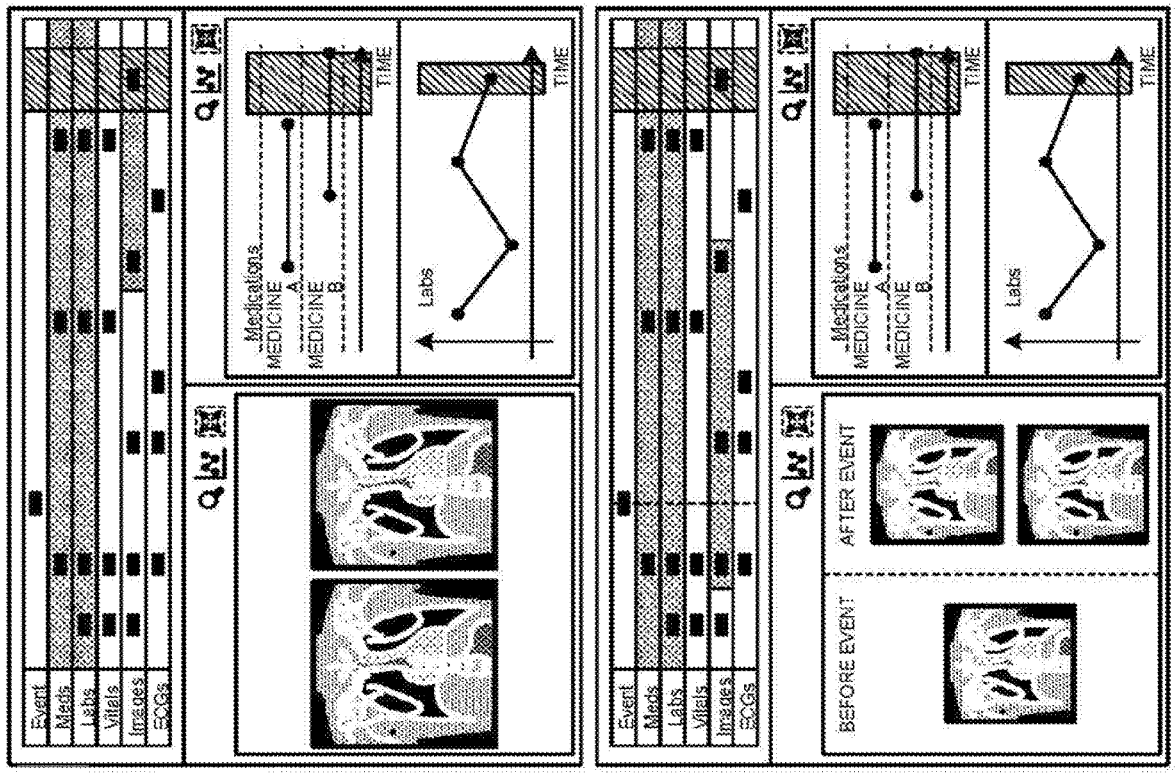
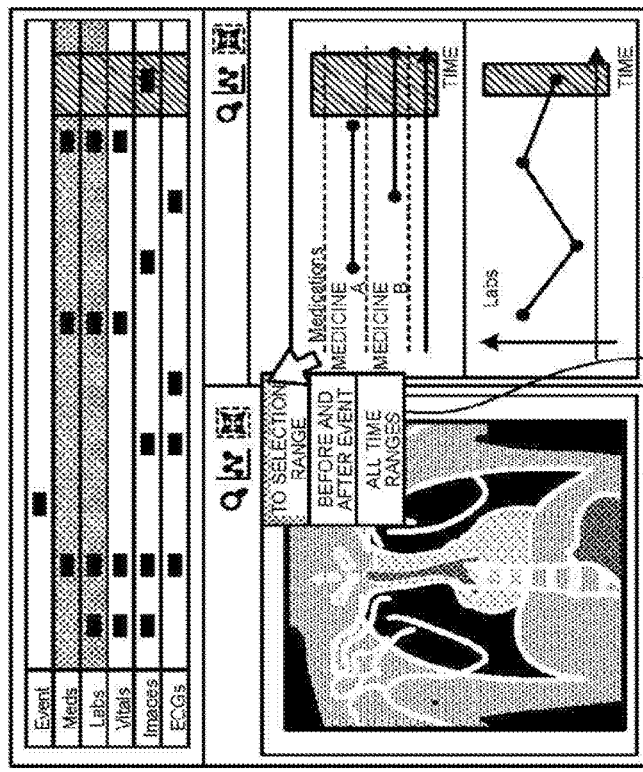

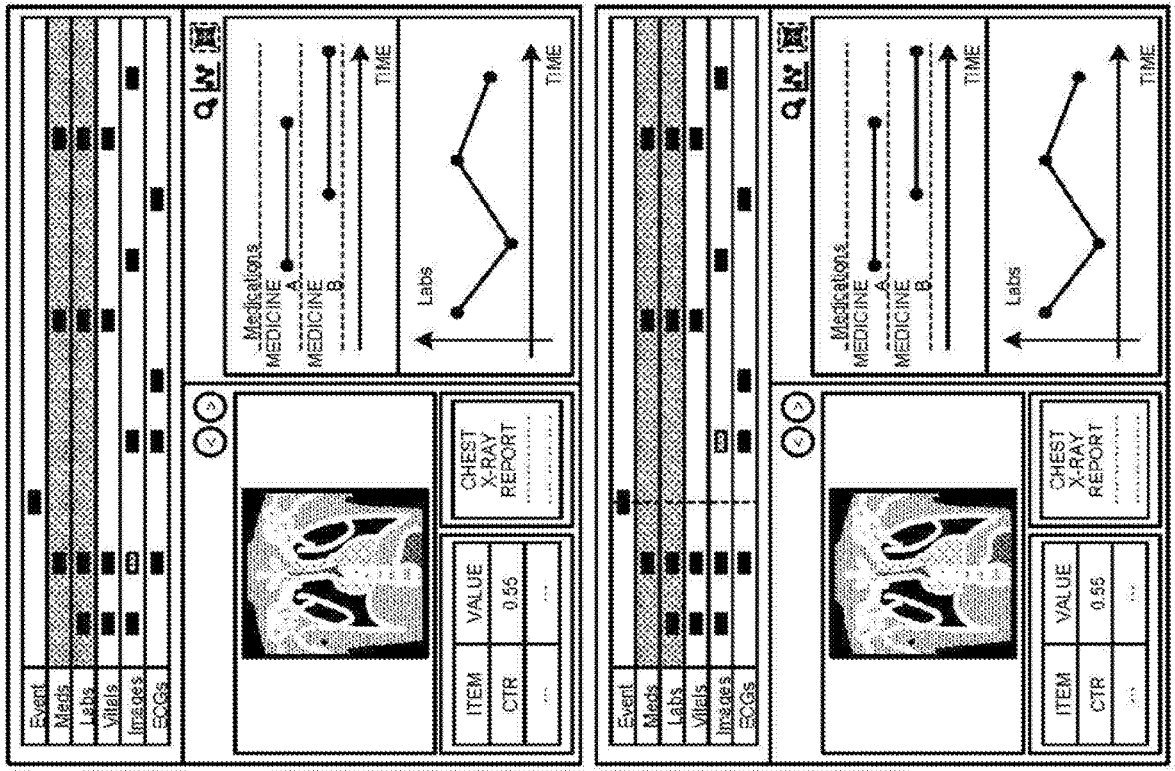
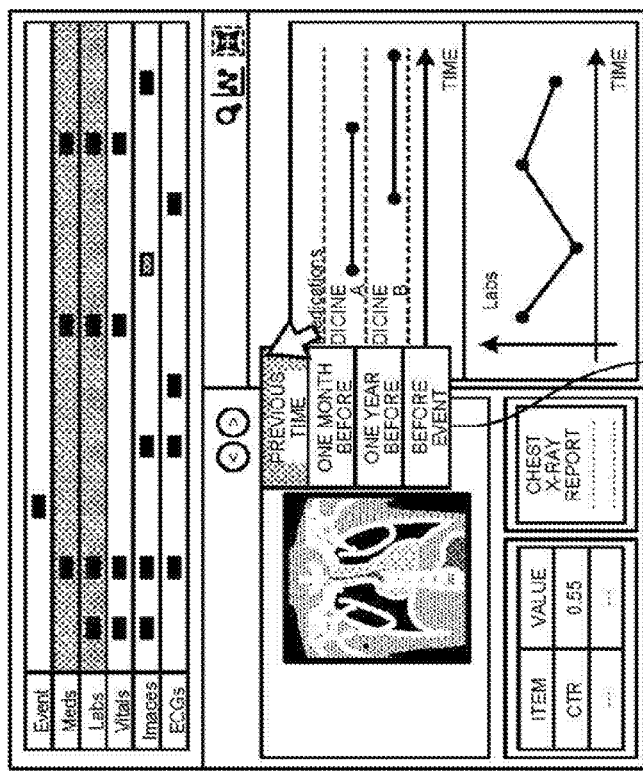
FIG.58

MEDICAL INFORMATION PROCESSING APPARATUS AND MEDICAL INFORMATION PROCESSING METHOD

CROSS-REFERENCE TO RELATED APPLICATIONS

This application is a continuation of PCT international application Ser. No. PCT/JP2018/013976 filed on Mar. 30, 2018 which designates the United States, incorporated herein by reference, and which claims the benefit of priority from Japanese Patent Application No. 2017-070998, filed on Mar. 31, 2017, the entire contents of which are incorporated herein by reference.

FIELD

Embodiments described herein relate generally to a medical information processing apparatus and a medical information processing method.

BACKGROUND

Conventionally, a system that displays, on one screen, various pieces of medical examination data necessary for diagnosis and consideration of a treatment plan by a physician has been desired. For example, a system that enables the physician to simultaneously check information about treatment such as medication, information about inspection such as specimen inspection and image inspection, and the like while comparing them and a system that enables the physician to grasp a condition of a subject, current treatment contents, and the like with high browsability have been expected.

BRIEF DESCRIPTION OF THE DRAWINGS

FIG. 3 is a diagram illustrating an example of a medication table in the first embodiment;

FIG. 4 is a diagram illustrating an example of a medication summary table in the first embodiment;

FIG. 5 is a diagram illustrating an example of an image table in the first embodiment;

FIG. 6 is a diagram illustrating an example of an image measurement value table in the first embodiment;

FIG. 7 is a diagram illustrating an example of an image reading report table in the first embodiment;

FIG. 8 is a diagram illustrating an example of an electrocardiogram table in the first embodiment;

FIG. 9 is a diagram illustrating an example of an electrocardiogram measurement value table in the first embodiment;

FIG. 10 is a diagram illustrating an example of an electrocardiogram report table in the first embodiment;

FIG. 11 is a diagram illustrating an example of a vital table in the first embodiment;

FIG. 12 is a diagram illustrating an example of a vital summary table in the first embodiment;

FIG. 13 is a diagram illustrating an example of a nursing record table in the first embodiment;

FIG. 14 is a diagram illustrating an example of a specimen inspection table in the first embodiment;

FIG. 15 is a diagram illustrating an example of a specimen inspection summary table in the first embodiment;

FIG. 16 is a diagram illustrating an example of a specimen inspection report table in the first embodiment;

FIG. 17 is a diagram illustrating an example of classification of data display formats in the first embodiment;

FIG. 18 is a diagram illustrating an example of a panel master table in the first embodiment;

FIG. 19 is a diagram illustrating an example of a data display table in the first embodiment;

FIG. 20 is a diagram illustrating an example of a display coordinate master table in the first embodiment;

FIG. 25 is a diagram illustrating another example of the display screen that the display control function generates;

FIG. 26 is a diagram illustrating still another example of the display screen that the display control function generates;

FIG. 40 is a diagram illustrating an example of magnification conversion that the converting function performs in the first embodiment;

FIG. 41 is a diagram illustrating another example of the magnification conversion that the converting function performs in the first embodiment;

FIG. 51 is a diagram illustrating an example of a pull-down menu that the display control function displays in the second embodiment;

FIG. 52 is a diagram illustrating an example of a granularity mapping table in the second embodiment;

FIG. 54 is a diagram illustrating an example of a display coordinate master table in the second embodiment;

FIG. 57 is a diagram illustrating another example of the magnification or reduction conversion that the converting function performs in the second embodiment;

FIG. 58 is a diagram illustrating an example of parallel movement conversion that the converting function performs in the second embodiment;

DETAILED DESCRIPTION

A medical information processing apparatus according to an embodiment includes processing circuitry. The processing circuitry is configured to display medical examination data on the basis of a medical examination data space having a dimension corresponding to a data display format determined for each piece of medical examination data. The processing circuitry is configured to perform space conversion with reference to a specified conversion reference point in the medical examination data space to switch display of the medical examination data that is displayed.

Hereinafter, embodiments of the medical information processing apparatus and a medical information processing method will be described in detail with reference to the accompanying drawings.

First Embodiment

Figure 1:
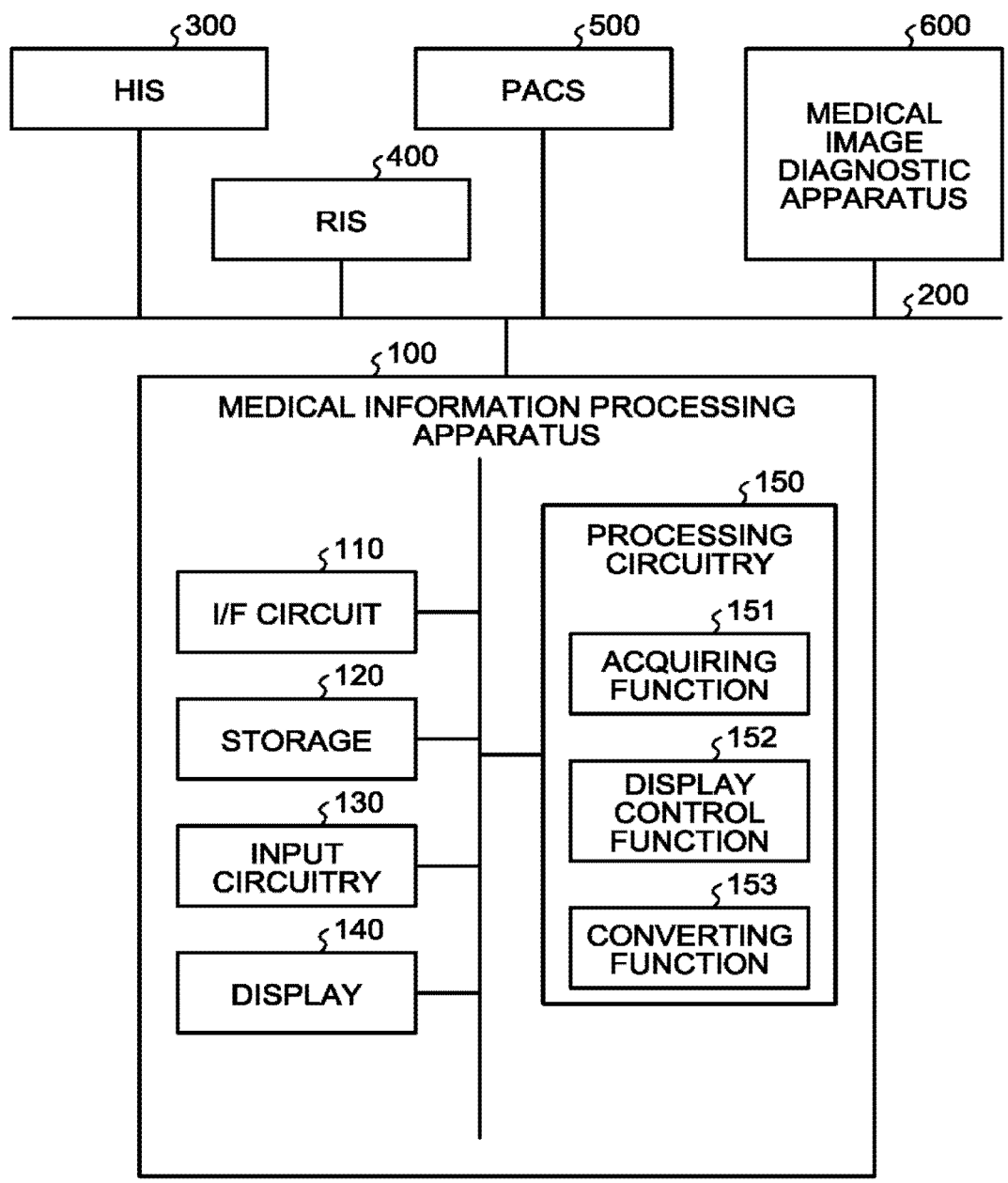
FIG. 1 is a diagram illustrating an example of the configuration of a medical information processing apparatus according to a first embodiment.

FIG. 1 is a diagram illustrating an example of the configuration of a medical information processing apparatus according to a first embodiment.

For example, as illustrated in FIG. 1, a medical information processing apparatus 100 in the embodiment is connected to a hospital information system (HIS) 300, a radiology information system (RIS) 400, picture archiving and communication systems (PACS) 500, and a medical image diagnostic apparatus 600 via a network 200 in a communicable manner. These apparatuses and systems are installed, for example, in a hospital and are connected to one another via the network 200 such as an in-hospital local area network (LAN).

The medical image diagnostic apparatus 600 is an apparatus that generates a medical image on the basis of pieces of data collected from a subject. The medical image diagnostic apparatus 600 is, for example, an X-ray diagnostic apparatus, an X-ray computed tomography (CT) apparatus, a magnetic resonance imaging (MRI) apparatus, an ultrasonic diagnostic apparatus, a single photon emission computed tomography (SPECT) apparatus, a positron emission computed tomography (PET) apparatus, a SPECT-CT apparatus in which the SPECT apparatus and the X-ray CT apparatus are integrated, or a PET-CT apparatus in which the PET apparatus and the X-ray CT apparatus are integrated.

The medical information processing apparatus 100 acquires various pieces of medical examination data from the HIS 300, the RIS 400, the PACS 500, and the medical image diagnostic apparatus 600 via the network 200 and performs various pieces of information processing using the pieces of acquired medical examination data. The medical information processing apparatus 100 is implemented by, for example, a computer apparatus such as a workstation.

To be specific, the medical information processing apparatus 100 includes an interface (I/F) circuit 110, a storage 120, input circuitry 130, a display 140, and processing circuitry 150.

The I/F circuit 110 is connected to the processing circuitry 150 and controls transmission of various pieces of data and communication with the HIS 300, the RIS 400, the PACS 500, and the medical image diagnostic apparatus 600. The I/F circuit 110, for example, receives pieces of medical examination data from the HIS 300, the RIS 400, the PACS 500, and the medical image diagnostic apparatus 600, and outputs the pieces of received medical examination data to the processing circuitry 150. The I/F circuit 110 is implemented by, for example, a network card, a network adapter, or a network interface controller (NIC).

The storage 120 is connected to the processing circuitry 150 and stores therein various pieces of data. The storage 120 stores therein, for example, the pieces of medical examination data received from the HIS 300, the RIS 400, the PACS 500, and the medical image diagnostic apparatus 600. The storage 120 is implemented by, for example, a random access memory (RAM), a semiconductor memory device such as a flash memory, a hard disk, or an optical disk.

The input circuitry 130 is connected to the processing circuitry 150, converts input operations received from an operator into electric signals, and outputs them to the processing circuitry 150. The input circuitry 130 is implemented by, for example, a track ball, a switch button, a mouse, a keyboard, or a touch panel.

The display 140 is connected to the processing circuitry 150 and displays various pieces of information and various pieces of image data output from the processing circuitry 150. The display 140 is implemented by, for example, a liquid crystal monitor, a cathode ray tube (CRT) monitor, or a touch panel.

The processing circuitry 150 controls components of the medical information processing apparatus 100 in accordance with the input operations received from the operator through the input circuitry 130. The processing circuitry 150, for example, controls to store the pieces of medical examination data output from the I/F circuit 110 in the storage 120. The processing circuitry 150, for example, reads the medical examination data from the storage 120 and displays it on the display 140. The processing circuitry 150 is implemented by, for example, a processor.

The example of the configuration of the medical information processing apparatus 100 in the embodiment has been described above. With this configuration, the medical information processing apparatus 100 in the embodiment displays various pieces of medical examination data related to a subject on the display 140.

Figure 2:
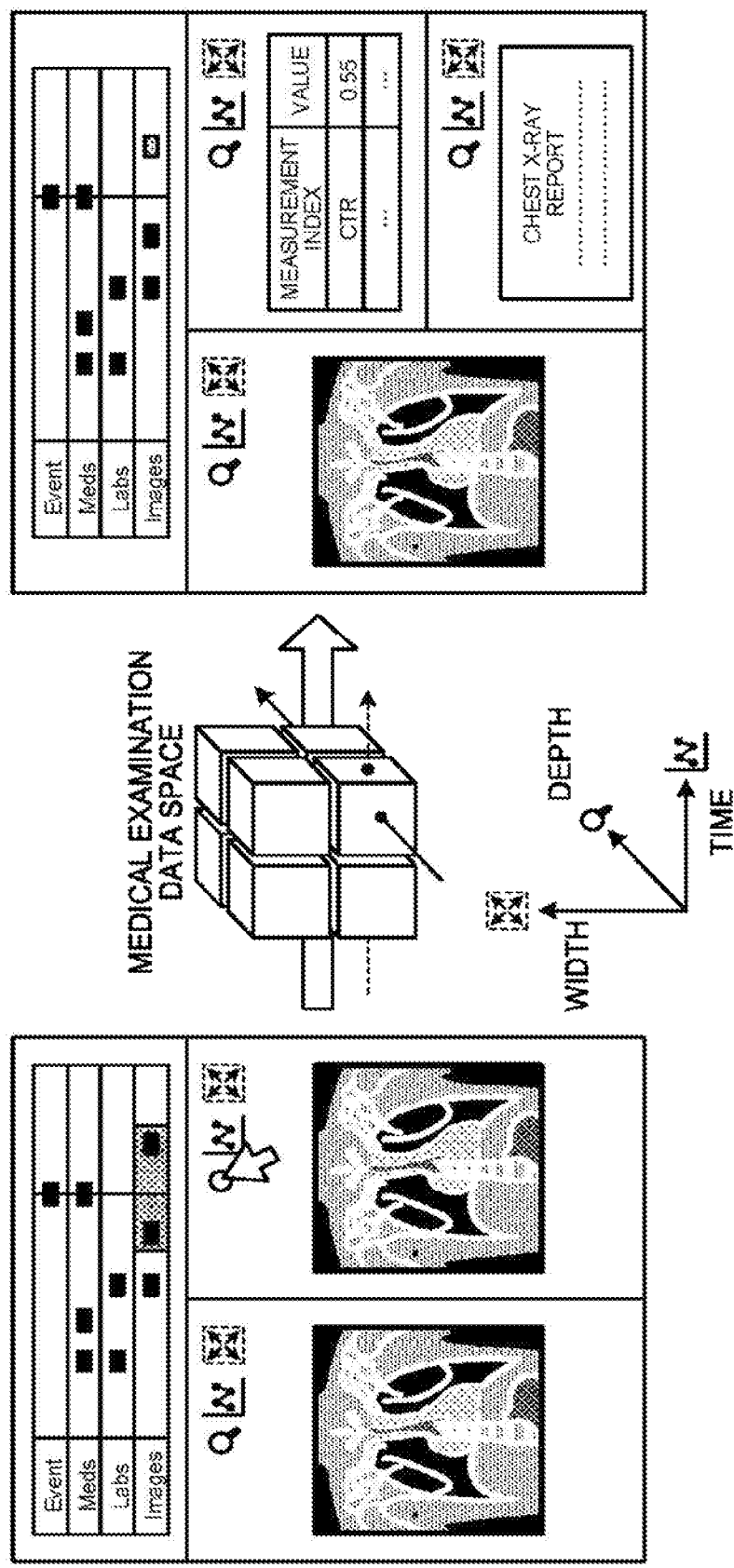
FIG. 2 is a diagram illustrating outline of display of medical examination data that the medical information processing apparatus performs in the first embodiment.

FIG. 2 is a diagram illustrating outline of display of the medical examination data that the medical information processing apparatus 100 performs in the first embodiment.

As illustrated in FIG. 2, the medical information processing apparatus 100 in the embodiment displays, on a display screen, various pieces of medical examination data such as image data, image measurement values, and an image reading report related to a subject, for example. The embodiment describes an example of the case in which the subject is a patient.

When the various pieces of medical examination data are simultaneously displayed on the display screen, increase in the quantity of information can cause visibility to be deteriorated. Data display is therefore desired to be appropriately switched in accordance with scenes in which the pieces of medical examination data are used. The display of the pieces of medical examination data requires switching for multilaterally browsing the pieces of medical examination data as in the case of focusing on time-series variations in inspection results, checking various pieces of data in a broad view, and so on.

In consideration of the desire, the medical information processing apparatus 100 in the embodiment has a function for presenting the pieces of medical examination data in appropriate display formats in accordance with clinical examination objects.

To be specific, in the embodiment, the processing circuitry 150 includes an acquiring function 151, a display control function 152, and a converting function 153. The display control function 152 is an example of a display controller. The converting function 153 is an example of a conversion unit.

The display control function 152 displays the medical examination data on the basis of a medical examination data space having a dimension corresponding to a data display format determined for each piece of medical examination data. The converting function 153 performs space conversion with reference to a specified conversion reference point in the medical examination data space to thereby switch display of the medical examination data that the display control function 152 displays. In the embodiment, the medical examination data space has three dimensions of a width, a depth, and time.

The "width" indicates a data type. The "depth" indicates data interpretation classification. The "data interpretation classification" referred herein is defined by, for example, a Data-Information-Knowledge-Wisdom (DIKW) model. With the DIKW model, pieces of data are classified into the following four types: Data, Information, Knowledge, and Wisdom. The amount of data is decreased and the value thereof as information is increased in the order of Data, Information, Knowledge, and Wisdom. For example, raw data such as an image and a numerical value corresponds to Data, and data with high-level data interpretation, such as a report, corresponds to Knowledge or Wisdom.

As mentioned above, the embodiment enables the pieces of medical examination data to be multilaterally browsed using information being currently displayed as a starting point by switching the display of the medical examination data with the space conversion with reference to the specified conversion reference point. The embodiment can thereby present the pieces of medical examination data in the appropriate display formats in accordance with the clinical examination objects.

The respective processing functions that the processing circuitry 150 has are stored in the storage 120 in a form of, for example, computer executable programs. The processing circuitry 150 reads the respective programs from the storage 120 and executes the respective read programs to implement the processing functions corresponding to the respective programs. In other words, the processing circuitry 150 that has read the respective programs has the respective processing functions illustrated in FIG. 1.

Hereinafter, the respective functions that the above-mentioned processing circuitry 150 has will be described in detail.

The acquiring function 151 acquires various pieces of medical examination data from the HIS 300, the RIS 400, the PACS 500, and the medical image diagnostic apparatus 600, and stores the pieces of acquired medical examination data in an integrated medical examination database (DB) that is constructed by the storage 120. The acquiring function 151 acquires, for example, pieces of information about medical examination, such as patient information, order information, order execution information, image inspection information, and various pieces of measurement information, as the pieces of medical examination data. The pieces of information that the acquiring function 151 acquires may be pieces of information held by the HIS 300, the RIS 400, the PACS 500, and the medical image diagnostic apparatus 600 as they are, information provided by integrating these pieces of information, or information created for secondary use.

For example, the processing, by the acquiring function 151, of acquiring the above-mentioned pieces of medical examination data from the HIS 300, the RIS 400, the PACS 500, and the medical image diagnostic apparatus 600 is executed asynchronously with pieces of processing that the display control function 152 and the converting function 153 perform, which will be described below. For example, the processing circuitry 150 reads a predetermined program corresponding to the acquiring function 151 from the storage 120 and executes it to thereby implement the processing that the acquiring function 151 performs.

The integrated medical examination DB has a plurality of tables prepared for respective types of the pieces of medical examination data. The integrated medical examination DB has, for example, a medication table, a medication summary table, an image table, an image measurement value table, an image reading report table, an electrocardiogram table, an electrocardiogram measurement value table, an electrocardiogram report table, a vital table, a vital summary table, a nursing record table, a specimen inspection table, a specimen inspection summary table, and a specimen inspection report table.

The medication table and the medication summary table are examples of tables based on the order information or the order execution information. The image table, the image measurement value table, and the image reading report table described herein are examples of tables based on the image inspection information. The electrocardiogram table, the electrocardiogram measurement value table, the electrocardiogram report table, the vital table, the vital summary table, the nursing record table, the specimen inspection table, the specimen inspection summary table, and the specimen inspection report table are examples of tables based on the various pieces of measurement information.

FIG. 3 is a diagram illustrating an example of the medication table in the first embodiment. The medication table stores therein pieces of medical examination data related to medications that have been performed on the patient.

As illustrated in FIG. 3, the medication table stores therein, for example, pieces of information while a medication ID, date and time, and data are made to correspond to one another. Identification information for uniquely identifying the medical examination data related to the medication is set to the medication ID. The date and time at which the medication was executed are set to the date and time. Information indicating a medicine used for the medication is set to the data. The medication table is prepared for each medicine type, for example.

FIG. 4 is a diagram illustrating an example of the medication summary table in the first embodiment. The medication summary table stores therein pieces of medical examination data related to pieces of medication summary data summarizing medications that have been performed on the patient at a plurality of time points.

As illustrated in FIG. 4, the medication summary table stores therein, for example, pieces of information while a medication summary ID and an order ID are made to correspond to each other. Identification information for uniquely identifying the medication summary data is set to the medication summary ID. The medication IDs of the respective medications contained in the medication summary data are set to the order ID.

The integrated medical examination DB may further have, for example, tables related to various orders of images, meals, rehabilitation, surgery, intravascular treatment, and radiotherapy and tables related to execution of the various orders in addition to the medication table and the medication summary table, as the tables based on the order information and the order execution information.

FIG. 5 is a diagram illustrating an example of the image table in the first embodiment. The image table stores therein pieces of medical examination data related to images provided by image capturing of the patient.

As illustrated in FIG. 5, the image table stores therein, for example, pieces of information while an image ID, date and time, and data are made to correspond to one another. Identification information for uniquely identifying the medical examination data related to the image is set to the image ID. The date and time at which the image was captured are set to the date and time. Image data of the image is set to the data. The image referred herein is a medical image provided by image capturing by the medical image diagnostic apparatus 600 (for example, various medical image diagnostic apparatuses such as the X-ray diagnostic apparatus, the X-ray CT apparatus, the MRI apparatus, the ultrasonic diagnostic apparatus, the SPECT apparatus, and the PET apparatus, the SPECT-CT apparatus in which the SPECT apparatus and the X-ray CT apparatus are integrated, the PET-CT apparatus in which the PET apparatus and the X-ray CT apparatus are integrated, or an apparatus group thereof). The image referred herein is generated in a format of, for example, a digital imaging and communication in medicine (DICOM) image (dcm), a portable network graphics (PNG) image, or a joint photographic experts group (JPEG) image. The image referred herein may be a still image or a moving image.

FIG. 6 is a diagram illustrating an example of the image measurement value table in the first embodiment. The image measurement value table stores therein pieces of medical examination data related to measurement values measured on the basis of the images provided by the image capturing of the patient.

As illustrated in FIG. 6, the image measurement value table stores therein, for example, pieces of information while a measurement value ID, the image ID, a measurement type, and data are made to correspond to one another. Identification information for uniquely identifying the medical examination data related to the image measurement value is set to the measurement value ID. Identification information for uniquely identifying the image used for measurement of the measurement value is set to the image ID. Information indicating a type (for example, a tumor diameter, a blood vessel diameter, and a flow rate) of the measurement value is set to the measurement type. The measurement value is set to the data.

FIG. 7 is a diagram illustrating an example of the image reading report table in the first embodiment. The image reading report table stores therein pieces of medical examination data related to image reading reports created on the basis of the images provided by the image capturing of the patient.

As illustrated in FIG. 7, the image reading report table stores therein, for example, pieces of information while an image reading report ID, the image ID, and a report are made to correspond to one another. Identification information for uniquely identifying the medical examination data related to the image reading report is set to the image reading report ID. Identification information for uniquely identifying the image used for creation of the image reading report is set to the image ID. Document data of the image reading report is set to the report. The document data of the image reading report referred herein may be in various document formats other than a doc format, or a text format.

FIG. 8 is a diagram illustrating an example of the electrocardiogram table in the first embodiment. The electrocardiogram table stores therein pieces of medical examination data related to electrocardiograms of the patient that have been measured in inspections.

As illustrated in FIG. 8, the electrocardiogram table stores therein, for example, pieces of information while an electrocardiogram ID, date and time, and data are made to correspond to one another. Identification information for uniquely identifying the medical examination data related to the electrocardiogram is set to the electrocardiogram ID. The date and time at which the electrocardiogram was measured are set to the date and time. Image data of the electrocardiogram is set to the data. The electrocardiogram referred herein is generated in a format of, for example, a PNG image or a JPEG image. The electrocardiogram referred herein may be a waveform data that is represented by medical waveform format encoding rules (MFER) and a comma separated value (CSV).

FIG. 9 is a diagram illustrating an example of the electrocardiogram measurement value table in the first embodiment. The electrocardiogram measurement value table stores therein pieces of medical examination data related to measurement values measured on the basis of the electrocardiograms of the patient.

As illustrated in FIG. 9, the electrocardiogram measurement value table stores therein, for example, pieces of information while a measurement value ID, the electrocardiogram ID, a measurement type, and data are made to correspond to one another. Identification information for uniquely identifying the medical examination data related to the electrocardiogram measurement value is set to the measurement value ID. Identification information for uniquely identifying the electrocardiogram used for measurement of the measurement value is set to the electrocardiogram ID. Information indicating a type (for example, a heart rate, a P-wave level, or a P-wave width) of the measurement value is set to the measurement type. The measurement value is set to the data.

FIG. 10 is a diagram illustrating an example of the electrocardiogram report table in the first embodiment. The electrocardiogram report table stores therein pieces of medical examination data related to electrocardiogram reports created on the basis of the electrocardiograms of the patient.

As illustrated in FIG. 10, the electrocardiogram report table stores therein, for example, pieces of information while an electrocardiogram report ID, the electrocardiogram ID, and a report are made to correspond to one another. Identification information for uniquely identifying the medical examination data related to the electrocardiogram report is set to the electrocardiogram report ID. Identification information for uniquely identifying the electrocardiogram used for creation of the electrocardiogram report is set to the electrocardiogram ID. Document data of the electrocardiogram report is set to the report. The document data of the electrocardiogram report referred herein may be in various document formats other than a doc format, or a text format.

FIG. 11 is a diagram illustrating an example of the vital table in the first embodiment. The vital table stores therein pieces of medical examination data related to vitals of the patient that have been measured in inspections.

As illustrated in FIG. 11, the vital table stores therein, for example, pieces of information while a vital ID, date and time, and data are made to correspond to one another. Identification information for uniquely identifying the medical examination data related to the vitals is set to the vital ID. The date and time at which the vitals were measured are set to the date and time. Measurement values (for example, a blood pressure, a pulse, and a body temperature) of the vitals are set to the data.

FIG. 12 is a diagram illustrating an example of a vital summary table in the first embodiment. The vital summary table stores therein pieces of medical examination data related to pieces of vital summary data summarizing the vitals that was measured from the patient at a plurality of time points.

As illustrated in FIG. 12, the vital summary table stores therein, for example, pieces of information while a vital summary ID and the vital ID are made to correspond to each other. Identification information for uniquely identifying the vital summary data is set to the vital summary ID. The vital IDs of the respective vitals contained in the vital summary data are set to the vital ID.

FIG. 13 is a diagram illustrating an example of the nursing record table in the first embodiment. The nursing record table stores therein pieces of medical examination data related to nursing records created on the basis of the vitals of the patient.

As illustrated in FIG. 13, the nursing record table stores therein, for example, pieces of information while a nursing record ID, the vital ID, and a report are made to correspond to one another. Identification information for uniquely identifying the medical examination data related to the nursing report is set to the nursing record ID. Identification information for uniquely identifying the vitals used for creation of the nursing report is set to the vital ID. Document data of the nursing report is set to the report. The document data of the nursing record referred herein may be in various document formats other than a doc format, or a text format.

FIG. 14 is a diagram illustrating an example of the specimen inspection table in the first embodiment. The specimen inspection table stores therein pieces of medical examination data related to specimen inspections of the patient.

As illustrated in FIG. 14, the specimen inspection table stores therein, for example, pieces of information while a specimen inspection ID, date and time, and data are made to correspond to one another. Identification information for uniquely identifying the medical examination data related to the specimen inspection is set to the specimen inspection ID. The date and time at which the specimen inspection was performed are set to the date and time. Measurement values (for example, measurement values of uric acid (UA), total protein (TP), and the like) of the specimen inspection are set to the data.

FIG. 15 is a diagram illustrating an example of the specimen inspection summary table in the first embodiment. The medication summary table stores therein pieces of medical examination data related to pieces of specimen inspection summary data summarizing specimen inspections that have been performed on the patient at a plurality of time points.

As illustrated in FIG. 15, the specimen inspection summary table stores therein, for example, pieces of information while a specimen inspection summary ID and the specimen inspection ID are made to correspond to each other. Identification information for uniquely identifying the specimen inspection summary data is set to the specimen inspection summary ID. The specimen inspection IDs of the respective specimen inspections contained in the specimen inspection summary data are set to the specimen inspection ID.

FIG. 16 is a diagram illustrating an example of the specimen inspection report table in the first embodiment. The specimen inspection report table stores therein pieces of medical examination data related to specimen inspection reports created on the basis of the specimen inspections of the patient.

As illustrated in FIG. 16, the specimen inspection report table stores therein, for example, pieces of information while a specimen inspection report ID, the specimen inspection ID, and a report are made to correspond to one another. Identification information for uniquely identifying the medical examination data related to the specimen inspection report is set to the specimen inspection report ID. Identification information for uniquely identifying the specimen inspection used for creation of the specimen inspection report is set to the specimen inspection ID. Document data of the specimen inspection report is set to the report. The document data of the specimen inspection report referred herein may be various document formats other than a doc format, or the text format.

In the embodiment, data display formats that are appropriate for browsing the above-mentioned respective pieces of medical examination data are determined for them. To be specific, the data display format is determined by a combination of the medical examination data and a panel indicating a specific display format (for example, a table format, a time-series format, an image display format, an electrocardiogram display format, or a report display format) when the medical examination data is displayed.

In the embodiment, the data display formats that are determined for the respective pieces of medical examination data are classified from various viewpoints in accordance with the clinical examination objects.

FIG. 17 is a diagram illustrating an example of classification of the data display formats in the first embodiment.

As indicated in the up-down direction in FIG. 17, the data display formats are classified into, for example, data display formats related to intervention and data display formats related to response. The data display formats related to the intervention are further classified into data display formats related to the medication and the data display formats related to the medication are further classified for each medicine type. The data display formats related to the response are further classified into data display formats related to the image, data display formats related to the electrocardiogram, data display formats related to the vitals, and data display formats related to the specimen inspection.

From another viewpoint, as illustrated in the right-left direction in FIG. 17, the data display formats are classified into, for example, data display formats related to objective data and data display formats related to subjective data. The data display formats related to the objective data are further classified into data display formats related to raw data and data display formats related to processed data. The data display formats related to the subjective data are further classified into data display formats related to character data.

From still another viewpoint, as illustrated in the right-upward oblique direction in FIG. 17, the data display formats are classified for each time-series time point.

For example, the data display format of the medical examination data that is stored in the above-mentioned medication table is classified as the data display format related to the medication and the raw data for each time-series time point as indicated in the first line from the top and the first column from the left in FIG. 17. The data display format of the medical examination data that is stored in the above-mentioned medication summary table is classified as the data display format related to the medication and the processed data in a data format summarizing the medications at a plurality of time points as indicated in the first line from the top and the second column from the left in FIG. 17.

The data display format of the medical examination data that is stored in the above-mentioned image table is classified as the data display format related to the image and the raw data for each time-series time point as indicated in the second line from the top and the first column from the left in FIG. 17. The data display format of the medical examination data that is stored in the above-mentioned image measurement value table is classified as the data display format related to the image and the processed data for each time-series time point as indicated in the second line from the top and the second column from the left in FIG. 17. The data display format of the medical examination data that is stored in the above-mentioned image reading report table is classified as the data display format related to the image and the character data for each time-series time point as indicated in the second line from the top and the third column from the left in FIG. 17.

The data display format of the medical examination data that is stored in the above-mentioned electrocardiogram table is classified as the data display format related to the electrocardiogram and the raw data for each time-series time point as indicated in the third line from the top and the first column from the left in FIG. 17. The data display format of the medical examination data that is stored in the above-mentioned electrocardiogram measurement value table is classified as the data display format related to the electrocardiogram and the processed data for each time-series time point as indicated in the third line from the top and the second column from the left in FIG. 17. The data display format of the medical examination data that is stored in the above-mentioned electrocardiogram report table is classified as the data display format related to the electrocardiogram and the character data for each time-series time point as indicated in the third line from the top and the third column from the left in FIG. 17.

The data display format of the medical examination data that is stored in the above-mentioned vital table is classified as the data display format related to the vitals and the raw data for each time-series time point as indicated in the fourth line from the top and the first column from the left in FIG. 17. The data display format of the medical examination data that is stored in the above-mentioned vital summary table is classified as the data display format related to the vitals and the processed data in a data format summarizing the measurement values of the vitals at a plurality of time points as indicated in the fourth line from the top and the second column from the left in FIG. 17. The data display format of the medical examination data that is stored in the above-mentioned nursing record table is classified as the data display format related to the vitals and the character data for each time-series time point as indicated in the fourth line from the top and the third column from the left in FIG. 17.

The data display format of the medical examination data that is stored in the above-mentioned specimen inspection table is classified as the data display format related to the specimen inspection and the raw data for each time-series time point as indicated in the fifth line from the top and the first column from the left in FIG. 17. The data display format of the medical examination data that is stored in the above-mentioned specimen inspection summary table is classified as the data display format related to the specimen inspection and the processed data in a data format summarizing the measurement values of the specimen inspections at a plurality of time points as indicated in the fifth line from the top and the second column from the left in FIG. 17. The data display format of the medical examination data that is stored in the above-mentioned specimen inspection report table is classified as the data display format related to the specimen inspection and the character data for each time-series time point as indicated in the fifth line from the top and the third column from the left in FIG. 17.

In the embodiment, the storage 120 stores therein a master for causing the respective data display formats to coordinates in the medical examination data space in accordance with the above-mentioned classification of the data display formats. As mentioned above, in the embodiment, the medical examination data space has the three dimensions of the width, depth, and time and is defined by three coordinate axes corresponding to the respective dimensions. That is to say, the medical examination data space is a space having three axes of the data type, time, and data interpretation classification as the coordinate axes.

The storage 120 stores therein, for example, a data display format master and a display coordinate master. The data display format master stores therein information indicating formats (hereinafter, referred to as panels) for displaying the pieces of medical examination data stored in the integrated medical examination DB. The data display format master has, for example, a panel master table and a data display table. The display coordinate master stores therein information indicating mapping representing coordinates to which the panels and the pieces of medical examination data correspond. The display coordinate master has, for example, a display coordinate master table.

FIG. 18 is a diagram illustrating an example of the panel master table in the first embodiment. The panel master table stores therein pieces of information related to various panels for displaying the pieces of medical examination data.

As illustrated in FIG. 18, the panel master table stores therein, for example, pieces of information while a panel ID and the panel are made to correspond to each other. Identification information for uniquely identifying the panel is set to the panel ID. A specific format of the panel is set to the panel.

FIG. 19 is a diagram illustrating an example of the data display table in the first embodiment. The data display table stores therein pieces of information related to the data display formats determined by the combinations of the pieces of medical examination data and the panels.

As illustrated in FIG. 19, the data display table stores therein, for example, pieces of information while a data display ID, the panel ID, and a data ID are made to correspond to one another. Identification information for uniquely identifying the data display format is set to the data display ID. The panel ID of the panel that is used in the data display format is set to the panel ID. The data ID of the medical examination data that is displayed in the data display format is set to the data ID.

Any one of the medication ID (see FIG. 3), the medication summary ID (see FIG. 4), the image ID (see FIG. 5), the measurement value ID (see FIG. 6), the image reading report ID (see FIG. 7), the electrocardiogram ID (see FIG. 8), the measurement value ID (see FIG. 9), the electrocardiogram report ID (see FIG. 10), the vital ID (see FIG. 11), the vital summary ID (see FIG. 12), the nursing record ID (see FIG. 13), the specimen inspection ID (see FIG. 14), the specimen inspection summary ID (see FIG. 15), and the specimen inspection report ID (see FIG. 16) as mentioned above is set to the data ID. The panels with which the respective pieces of medical examination data stored in the tables in the integrated medical examination DB are displayed are thereby determined.

FIG. 20 is a diagram illustrating an example of the display coordinate master table in the first embodiment. The display coordinate master table stores therein pieces of information while coordinates in the medical examination data space are made to correspond to the respective data display formats determined by the combinations of the pieces of medical examination data and the panels. The medical examination data thereby has a data structure corresponding to the coordinate axes of the medical examination data space.

As illustrated in FIG. 20, the display coordinate master table stores therein, for example, pieces of information while a coordinate ID, the data display ID, Width, Time, and Depth are made to correspond to one another. Identification information for uniquely identifying the coordinates in the medical examination data space is set to the coordinate ID. The data display ID of the data display format corresponding to the coordinates is set to the data display ID. Coordinate values indicating the coordinates are set to Width, Time, and Depth.

In the example illustrated in FIG. 20, for example, coordinate values (1,(1,2,3),2) corresponding to a coordinate ID "Coor0007" and coordinate values (4,(2 to 6),2) corresponding to a coordinate ID "Coor0008" respectively indicate segments along the time direction in the medical examination data space. Coordinate values (5,*,2) corresponding to a coordinate ID "Coor0009" indicate a line along the time direction in the medical examination data space. In this manner, a line in the medical examination data space is indicated by setting a plurality of coordinate values or "*" to any one of the coordinate values for Width, Time, and Depth. A point in the medical examination data space is indicated by setting one numerical value to each of Width, Time, and Depth like coordinate values set to other pieces of information illustrated in FIG. 20. Although not illustrated in FIG. 20, a plane in the medical examination data space is indicated by setting "*" to any two of the coordinate values for Width, Time, and Depth.

Figure 21:
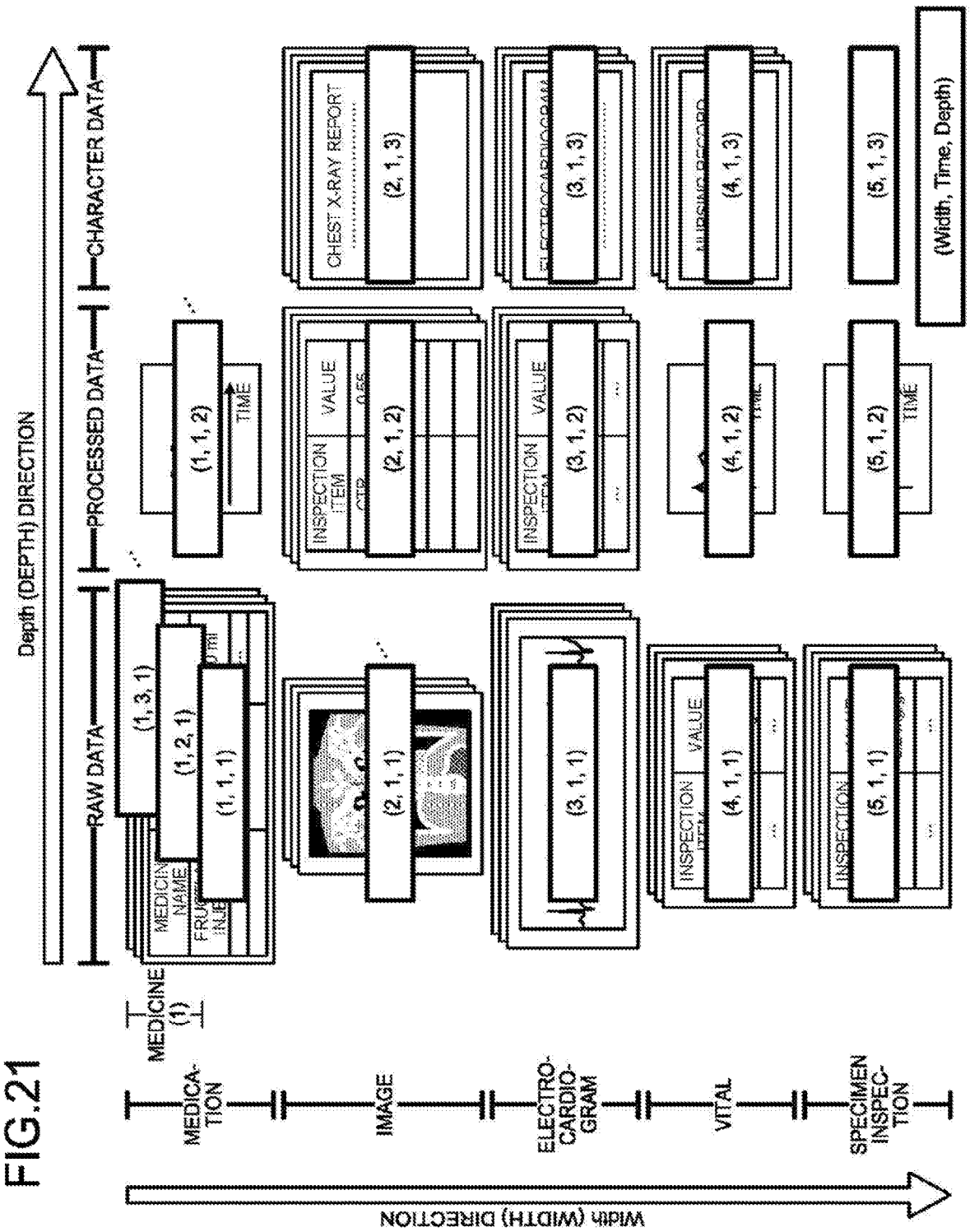
FIG. 21 is a diagram illustrating an example of correspondence between the data display formats and coordinates in a medical examination data space by a display coordinate master in the first embodiment.

FIG. 21 is a diagram illustrating an example of correspondence between the data display formats and coordinates in the medical examination data space by the display coordinate master in the first embodiment. FIG. 21 illustrates an example of the case in which coordinates in the medical examination data space are made to correspond to the respective data display formats illustrated in FIG. 17.

As illustrated in FIG. 21, the display coordinate master causes coordinates (Width, Time, and Depth) in the medical examination data space to correspond to the respective data display formats determined for the respective pieces of medical examination data in accordance with the respective classifications, for example.

For example, coordinates are made to correspond to the respective data display formats such that the coordinate values are increased in the order of the medication, the image, the electrocardiogram, the vital, and the specimen inspection in the Width direction. Coordinates are made to correspond to the respective data display formats such that the coordinate values are increased in the order of the raw data, the processed data, and the character data in the Depth direction. Coordinates are made to correspond to the respective data display formats such that the coordinate values are increased in the time-series order in the Time direction (right-upward oblique direction in FIG. 21).

In the above-mentioned example, the pieces of medical examination data held in the integrated medical examination DB are stored in the tables for the raw data, the processed data, and the character data, as an example. The embodiment is, however, not limited to the case. The integrated medical examination DB may store therein the pieces of medical examination data in units of tables that are different from the above-mentioned tables, for example. The pieces of medical examination data that the integrated medical examination DB holds are not limited to those mentioned above and various other pieces of medical examination data may be used.

The display control function 152 and the converting function 153 will be described with reference to FIG. 1, again.

The display control function 152 displays the medical examination data on the basis of the medical examination data space having the dimension corresponding to the data display format determined for each piece of medical examination data. The converting function 153 performs space conversion with reference to the specified conversion reference point in the medical examination data space to thereby switch display of the medical examination data that the display control function 152 displays.

Figure 22:
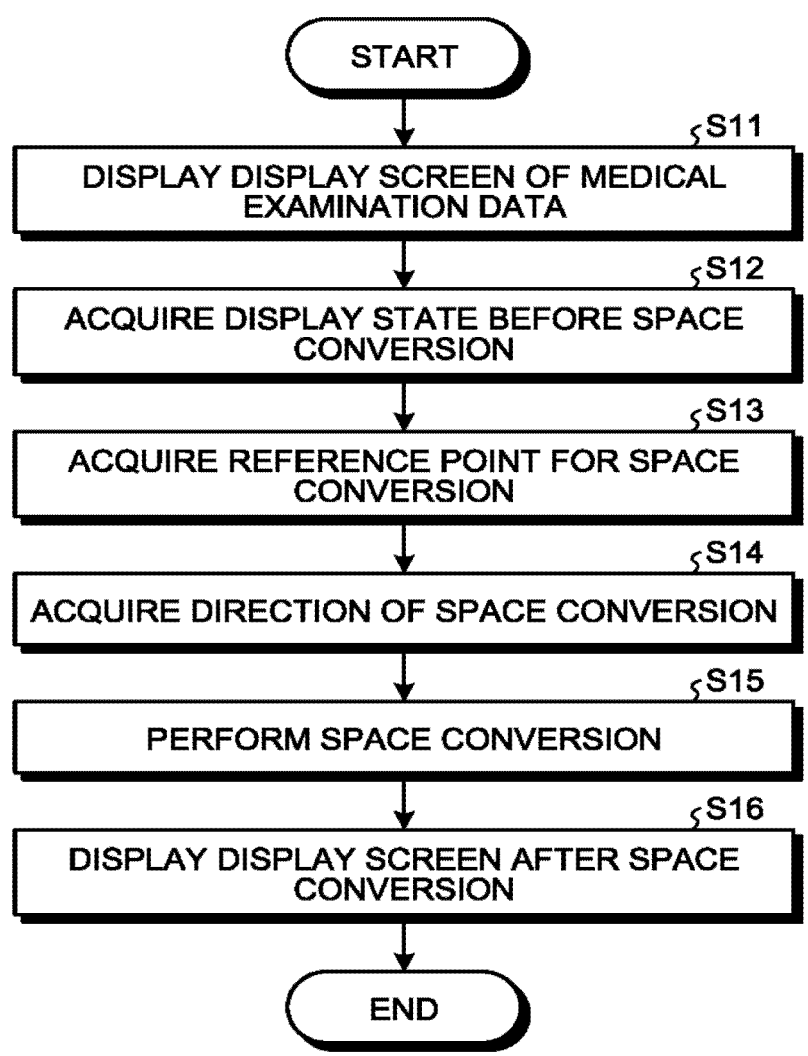
FIG. 22 is a flowchart illustrating flow of pieces of processing that a display control function and a converting function perform in the first embodiment.

FIG. 22 is a flowchart illustrating flow of pieces of processing that the display control function 152 and the converting function 153 perform in the first embodiment. FIG. 22 illustrates overall flow of the pieces of processing that the display control function 152 and the converting function 153 perform.

As illustrated in FIG. 22, in the embodiment, for example, the display control function 152 displays a display screen of the medical examination data (step S11). To be specific, the display control function 152 generates the display screen for displaying the medical examination data on the basis of the above-mentioned medical examination data space and displays the generated display screen on the display 140.

The converting function 153 acquires a display state before space conversion (step S12). To be specific, the converting function 153 acquires the display state (the coordinates that are displayed and the dimension (a point, line, plane, or the like) that is displayed) before the space conversion on the basis of information being displayed on the display screen and a screen operation by an operator. The display state before the space conversion is indicated by a point, line, or plane in the medical examination data space. It should be noted that hereinafter, the display state before the space conversion is referred to as a "pre-conversion state".

The converting function 153 acquires a reference point for the space conversion (step S13). To be specific, the converting function 153 acquires the reference point for the space conversion on the basis of a screen operation by the operator. The reference point for the space conversion is indicated by a point, line, or plane in the medical examination data space. It should be noted that hereinafter, the reference point for the space conversion is referred to as a "conversion reference point".

The converting function 153 further acquires a direction of the space conversion (step S14). To be specific, the converting function 153 acquires the direction of the space conversion on the basis of a screen operation by the operator. It should be noted that hereinafter, the direction of the space conversion is referred to as a "conversion direction".

The converting function 153 then performs the space conversion (step S15). To be specific, the converting function 153 acquires a display state (the coordinates that are displayed and the dimension (a point, line, plane, or the like) that is displayed) after the space conversion on the basis of the acquired pre-conversion state, conversion reference point, and conversion direction, and information of the display coordinate master. The display state after the space conversion is indicated by a point, line, or plane in the medical examination data space. It should be noted that hereinafter, the display state after the space conversion is referred to as a "post-conversion state".

Thereafter, the display control function 152 displays a display screen after the space conversion (step S16). To be specific, the display control function 152 generates a display screen after the space conversion on the basis of the post-conversion state acquired by the space conversion by the converting function 153, and pieces of information of the data display format master and the integrated medical examination DB, and displays the generated display screen on the display 140.

For example, the processing circuitry 150 reads the predetermined program corresponding to the display control function 152 from the storage 120 and executes it to thereby implement the above-mentioned pieces of processing at steps S11 and S16. For example, the processing circuitry 150 reads the predetermined program corresponding to the converting function 153 from the storage 120 and executes it to thereby implement the above-mentioned pieces of processing at steps S12 to S15.

Hereinafter, the above-mentioned processing that each of the display control function 152 and the converting function 153 performs will be described more in detail.

First, the display control function 152 will be described. The display control function 152 determines the data display format (a layout, a type of the medical examination data, and the like) of the post-conversion state using the post-conversion state acquired by the converting function 153 and the information of the data display format master. The display control function 152 generates the display screen using the pieces of data that the integrated medical examination DB holds and displays the generated display screen on the display 140.

Figure 23:
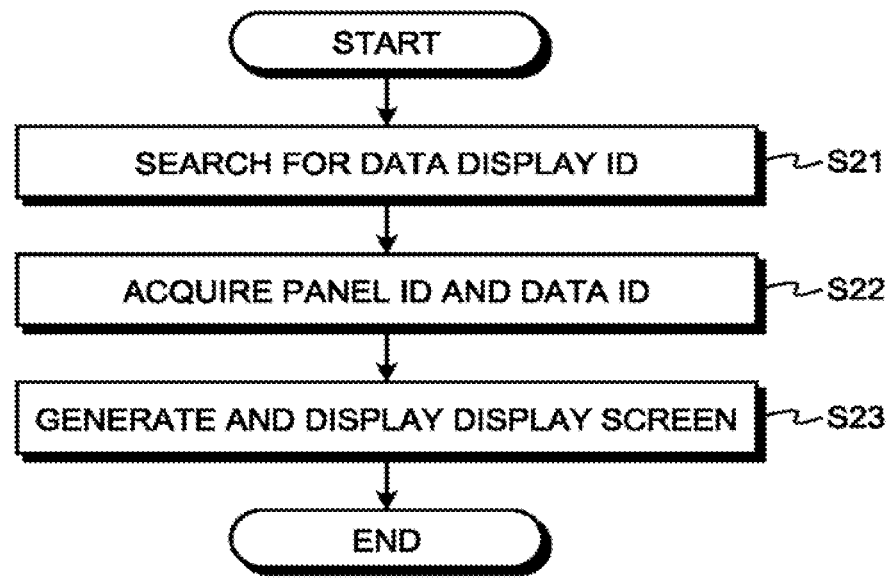
FIG. 23 is a flowchart illustrating flow of processing that the display control function performs in the first embodiment.

FIG. 23 is a flowchart illustrating flow of the processing that the display control function 152 performs in the first embodiment.

As illustrated in FIG. 23, for example, the display control function 152 first searches the display coordinate master table for the data display ID on the basis of the coordinates that the converting function 153 has calculated as the post-conversion state (step S21). In this case, the display control function 152 searches for the data display IDs when the coordinates that the converting function 153 has calculated indicate a line or a plane.

Subsequently, the display control function 152 acquires the panel ID and the data ID from the data display table of the data display format master on the basis of the searched data display ID (step S22). In this case, the display control function 152 acquires a plurality of combinations of the panels ID and the data IDs when there are the searched data display IDs.

Thereafter, the display control function 152 acquires the corresponding data from the integrated medical examination DB on the basis of the acquired data ID, acquires the corresponding panel from the panel master table of the data display format master, and generates the display screen by assigning the acquired data to the panel. The display control function 152 displays the generated display screen on the display 140 (step S23).

FIGS. 24 to 27 are diagrams illustrating examples of the display screen that the display control function 152 generates. The examples illustrated in FIGS. 24 to 27 are examples when the data display formats illustrated in FIG. 17 and FIG. 21 are displayed. The examples illustrated in FIGS. 24 to 27 correspond to the image table illustrated in FIG. 5, the image measurement value table illustrated in FIG. 6, the image reading report table illustrated in FIG. 7, the panel master table illustrated in FIG. 18, the data display table illustrated in FIG. 19, and the display coordinate master table illustrated in FIG. 20. In the following description, the coordinates (Width,Time,Depth) indicating the position in the medical examination data space are expressed as (W,T,D) simply.

Figure 24:
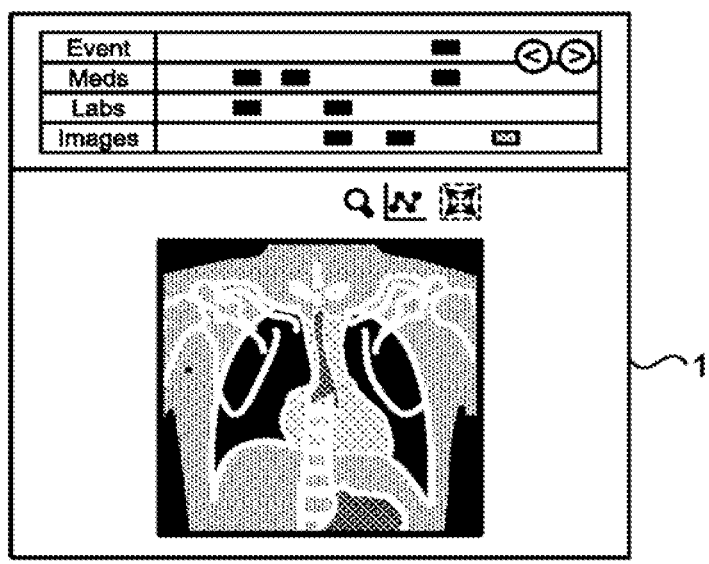
FIG. 24 is a diagram illustrating an example of a display screen that the display control function generates.

For example, as illustrated in FIG. 24, when the coordinates that the converting function 153 has calculated are (W,T,D)=(2,1,1), the display control function 152 generates a display screen on which a data display format 1 of image data that is made to correspond to the coordinates in the medical examination data space is arranged.

To be specific, the display control function 152 acquires the data display ID of "DView0002" from the display coordinate master table on the basis of the coordinates (2,1,1) that the converting function 153 has calculated. Subsequently, the display control function 152 acquires the panel ID of "Panel0003" and the data ID of "Img0001" from the data display table on the basis of the acquired data display ID of "DView0002". Thereafter, the display control function 152 acquires data of "20170210_1020.dcm" from the image table in the integrated medical examination DB on the basis of the acquired data ID of "Img0001" and further acquires "image display panel" from the panel master table on the basis of the acquired panel ID of "Panel0003". Then, the display control function 152 assigns the acquired data of "20170210_1020.dcm" to "image display panel" to generate the data display format 1 of the image data and generate the display screen on which the data display format 1 is arranged.

For example, as illustrated in FIG. 25, when the coordinates that the converting function 153 has calculated are (W,T,D)=(2,1,2), the display control function 152 generates a display screen on which a data display format 2 of image measurement values that is made to correspond to the coordinates in the medical examination data space is arranged.

To be specific, the display control function 152 acquires the data display ID of "DView0003" from the display coordinate master table on the basis of the coordinates (2,1,2) that the converting function 153 has calculated. Subsequently, the display control function 152 acquires the panel ID of "Panel0001" and the data IDs "ImgMes0001", "ImgMes0002", . . . from the data display table on the basis of the acquired data display ID of "DView0003". Thereafter, the display control function 152 acquires the measurement types and the pieces of data corresponding to the respective data IDs from the image measurement value table in the integrated medical examination DB on the basis of the acquired data IDs of "ImgMes0001", "ImgMes0002", . . . , and further acquires "table format panel" from the panel master table on the basis of the acquired panel ID of "Panel0001". Then, the display control function 152 assigns the respective acquired measurement types and pieces of data to "table format panel" to generate the data display format 2 of the image measurement values and generate the display screen on which the data display format 2 is arranged.

For example, as illustrated in FIG. 26, when the coordinates that the converting function 153 has calculated are (W,T,D)=(2,1,3), the display control function 152 generates a display screen on which a data display format 3 of an image reading report that is made to correspond to the coordinates in the medical examination data space is arranged.

To be specific, the display control function 152 acquires the data display ID of "DView0010" from the display coordinate master table on the basis of the coordinates (2,1,3) that the converting function 153 has calculated. Subsequently, the display control function 152 acquires the panel ID of "Panel0005" and the data ID of "ImgRep0001" from the data display table on the basis of the acquired data display ID of "DView0010". Thereafter, the display control function 152 acquires data of "report0001.doc" from the image reading report table in the integrated medical examination DB on the basis of the acquired data ID of "ImgRep0001" and further acquires "report display panel" from the panel master table on the basis of the acquired panel ID of "Panel0005". Then, the display control function 152 assigns the acquired data of "report0001.doc" to "image display panel" to generate the data display format 3 of the image reading report and generate the display screen on which the data display format 3 is arranged.

Figure 27:
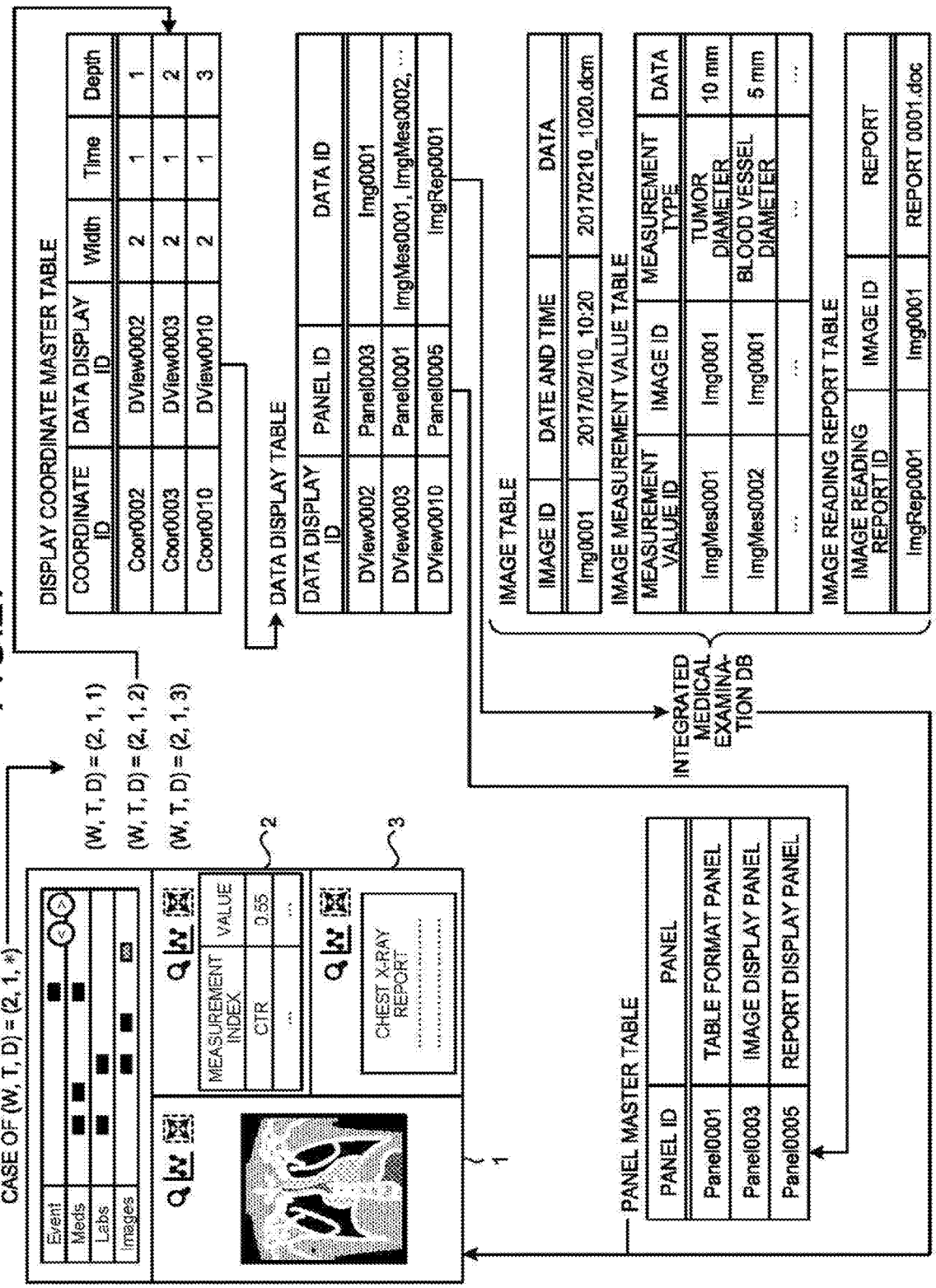
FIG. 27 is a diagram illustrating still another example of the display screen that the display control function generates.

For example, as illustrated in FIG. 27, when the coordinates that the converting function 153 has calculated are (W,T,D)=(2,1,*), the display control function 152 generates a display screen on which the data display formats 1 to 3 for simultaneously displaying the pieces of medical examination data that are made to correspond to a plurality of points contained in a line indicated by the coordinates in the medical examination data space are arranged.

To be specific, the display control function 152 acquires the data display IDs of "DView0002", "DView0003", and "DView0010" corresponding to the coordinates (2,1,1), (2,1,2), and (2,1,3) from the display coordinate master table on the basis of the coordinates (2,1,*) that the converting function 153 has calculated. Subsequently, the display control function 152 acquires a combination of "Panel0003" and "Img0001", a combination of "Panel0001" and "ImgMes0001", "ImgMes0002", . . . , and a combination of "Panel0005" and "ImgRep0001" as the combinations of the panel IDs and the data IDs from the data display table on the basis of the respective acquired data display IDs.

Thereafter, the display control function 152 acquires the data of "20170210_1020.dcm" from the image table in the integrated medical examination DB and acquires "image display panel" from the panel master table on the basis of the acquired combination of "Panel0003" and "Img0001". Then, the display control function 152 assigns the acquired data of "20170210_1020.dcm" to "image display panel" to generate the data display format 1 of the image data. The display control function 152 acquires the measurement types and the pieces of data corresponding to the respective data IDs from the image measurement value table in the integrated medical examination DB and acquires "table format panel" from the panel master table on the basis of the acquired combination of "Panel0001" and "ImgMes0001", "ImgMes0002", . . . . Then, the display control function 152 assigns the respective acquired measurement types and pieces of data to "table format panel" to generate the data display format 2 of the image measurement values. The display control function 152 acquires the data of "report0001.doc" from the image reading report table in the integrated medical examination DB and acquires "report display panel" from the panel master table on the basis of the acquired combination of "Panel0005" and "ImgRep0001". Then, the display control function 152 assigns the acquired data of "report0001.doc" to "report display panel" and generates the data display format 3 of the image reading report.

The display control function 152 generates the display screen on which the generated data display formats 1 to 3 are arranged. In this case, the display control function 152 generates the data display formats when there are the combinations of the panel IDs and the data IDs acquired from the data display table of the data display format master. Then, the display control function 152 generates a layout of the display screen in accordance with predetermined rules when it generates the data display formats. The display control function 152 generates the layout of the display screen such that, for example, the respective pieces of data are arranged in the order of the raw data, the processed data, and the character data from the left for display. The display control function 152 generates the layout of the display screen such that, for example, the data related to the image is largely displayed at the left side and the processed data and the character data are arranged vertically on the right side for display.

In the embodiment, the display control function 152 provides a reception unit for receiving, from the operator, specification of the pre-conversion state, the conversion reference point, and the conversion direction through the display screen.

Figure 28:
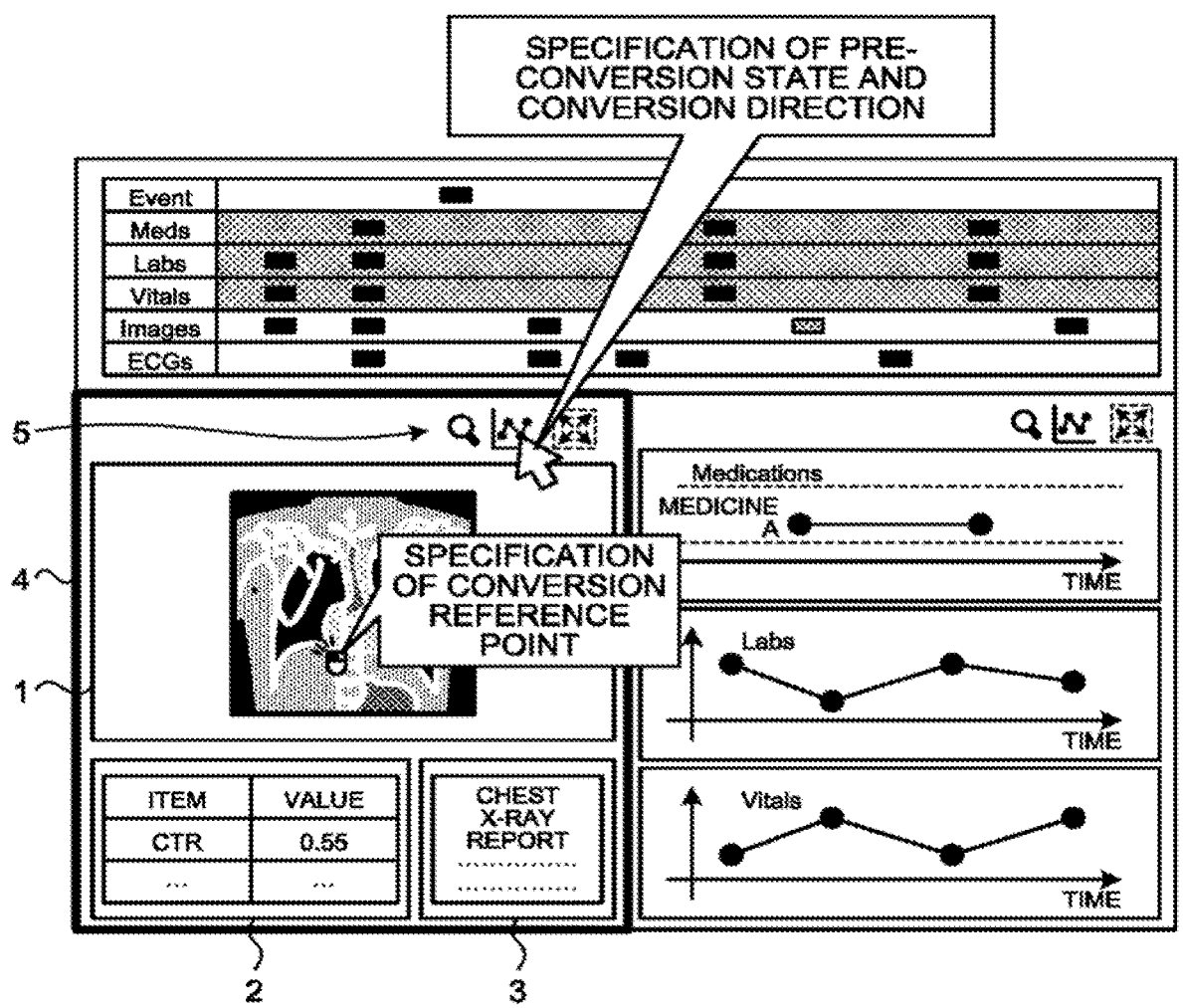
FIG. 28 is a diagram illustrating an example of a reception unit that the display control function provides in the first embodiment.

FIG. 28 is a diagram illustrating an example of the reception unit that the display control function 152 provides in the first embodiment.

As illustrated in FIG. 28, the display control function 152, for example, arranges, on the display screen, an operation reception unit for receiving an operation of specifying the pre-conversion state and the conversion direction by a unit of a data display format 4 collectively displaying the data display formats 1 to 3 as a unit of the pre-conversion state using the data display format 4.

The display control function 152 arranges, as the operation reception unit, three icons 5 side by side in the right and left direction on the data display format 4 collectively displaying the data display formats 1 to 3, for example. When the display control function 152 receives an operation on any one of the three icons 5, it identifies that the data display format on which the icon is arranged has been specified as the pre-conversion state. When an operation on the icon at the left side is performed, for example, the display control function 152 identifies that the depth direction has been specified as the conversion direction. When an operation on the icon at the center is performed, for example, the display control function 152 identifies that the time direction has been specified as the conversion direction. When an operation on the icon at the right side is performed, for example, the display control function 152 identifies that the width direction has been specified as the conversion direction.

Furthermore, the display control function 152 arranges, on the display screen, an operation reception unit for receiving the specification of the conversion reference point by a unit of the individual data display formats contained in the data display format 4 collecting the data display formats 1 to 3. The display control function 152 sets each of regions in the respective panels of the individual data display formats to the operation reception unit, for example. When the display control function 152 receives an operation on the region in the panel of any one of the data display formats, it identifies that the data display format has been specified as the conversion reference point.

Although the specification of the pre-conversion state is received by the unit provided by collecting the data display formats indicated by the points, as an example, the embodiment is not limited thereto. The display control function 152 may receive the specification of the conversion direction, for example, for each data display format of a line provided by collecting a plurality of points or each data display format of a plane provided by collecting a plurality of lines using the data display format indicated by the line or the data display format indicated by the plane.

The display control function 152 may receive an operation not by previously arranging the icons on the display screen but in accordance with an operation type (position on the display screen on which the operation has been performed, a click with a mouse, or the like), for example.

Figure 29:
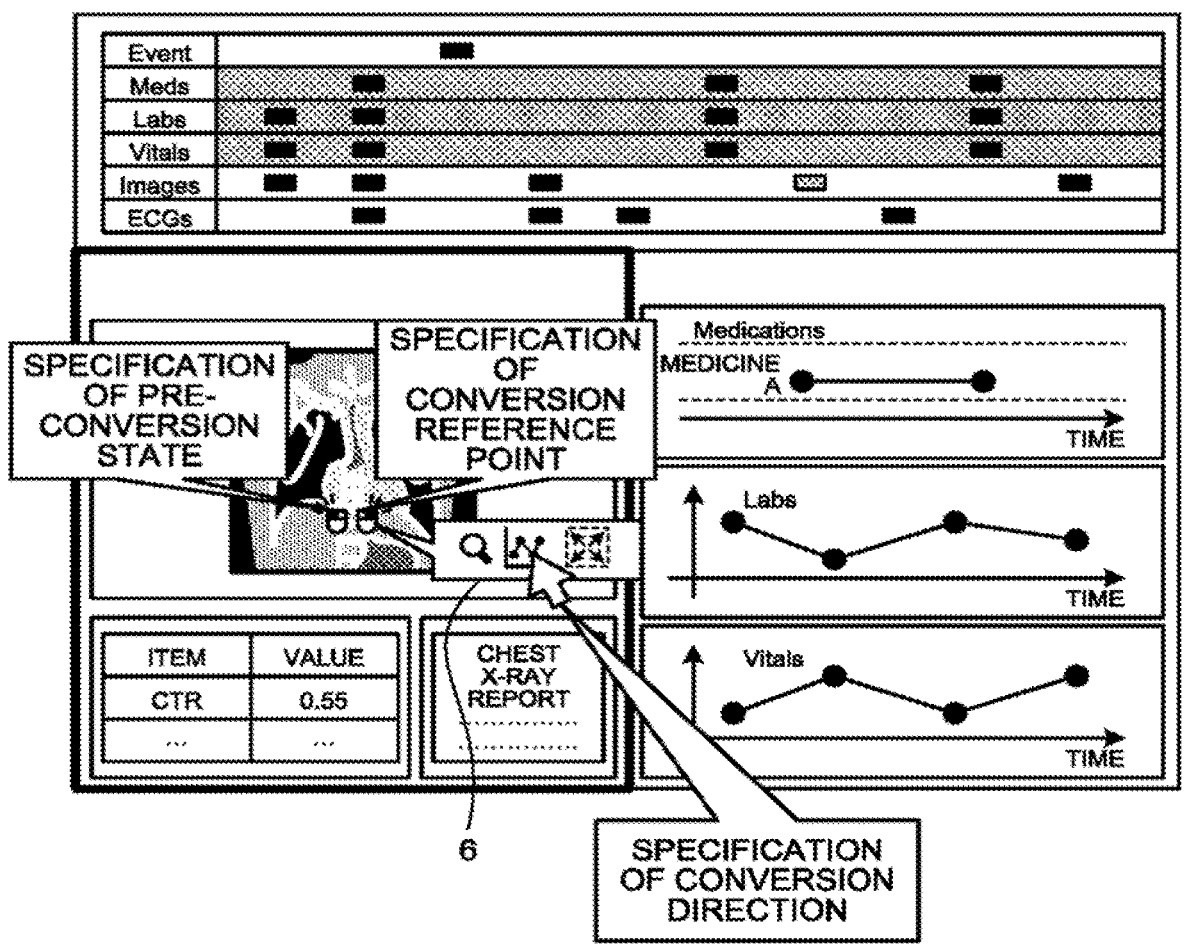
FIG. 29 is a diagram illustrating another example of the reception unit that the display control function provides in the first embodiment.

FIG. 29 is a diagram illustrating another example of the reception unit that the display control function 152 provides in the first embodiment.

As illustrated in FIG. 29, the display control function 152, for example, identifies, as the pre-conversion state, the data display format at a position specified by a left click with a mouse and identifies, as the conversion reference point, the data display format at a position specified by a right click with the mouse. Furthermore, for example, when the right click with the mouse is performed, the display control function 152 displays a context menu 6 on which an icon for specifying the depth direction, an icon for specifying the time direction, and an icon for specifying the width direction are arranged side by side and receives specification of the conversion direction.

In the example illustrated in FIG. 29, the pre-conversion state and the conversion reference point are specified on the same data display format and an operation of specifying a point in the medical examination data space is therefore performed. When the pre-conversion state and the conversion reference point are set to be the same as mentioned above, for example, the operation of the left click may be omitted. In this case, the display control function 152 identifies, as the pre-conversion state and the conversion reference point, the data display format at the position specified by the right click.

When the display control function 152 receives the operation of specifying the pre-conversion state and the conversion reference point, it may receive an operation of specifying a point or a segment in the time direction in the medical examination data space, for example.

Figure 30:
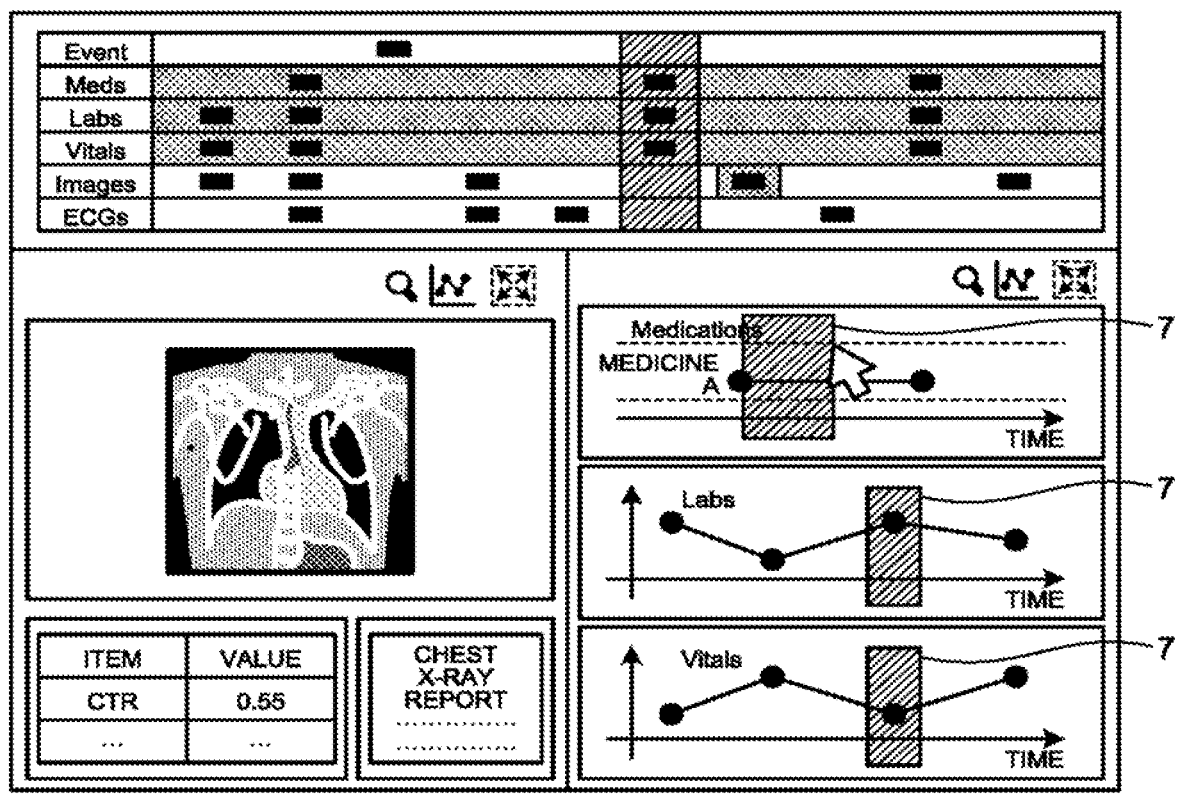
FIG. 30 is a diagram illustrating still another example of the reception unit that the display control function provides in the first embodiment.

FIG. 30 is a diagram illustrating still another example of the reception unit that the display control function 152 provides in the first embodiment.

As illustrated in FIG. 30, the display control function 152, for example, displays a graphic 7 for specifying a time point or a time range on the data display format containing a component in the time direction. The display control function 152 identifies a point or a segment in the time direction by receiving an operation of changing a position or a size of the graphic 7 with an operation such as a click and drag with the mouse, for example. When the data display formats containing the component in the time direction are displayed on the display screen, for example, the display control function 152 displays the graphics 7 on the respective data display formats and links the respective graphics so as to indicate the same time point or the same time range.

The display control function 152 may further display guide information indicating a position in the medical examination data space that corresponds to the data display format being displayed, for example.

Figure 31:
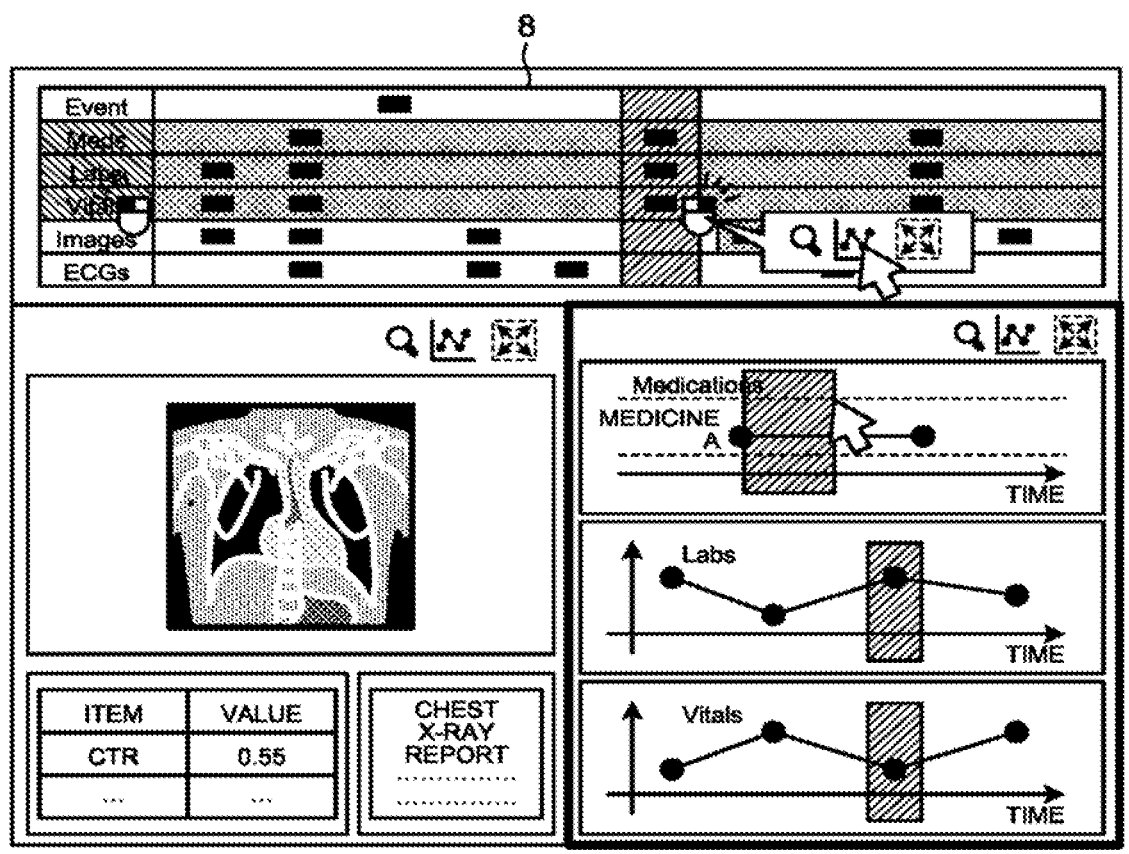
FIG. 31 is a diagram illustrating still another example of the reception unit that the display control function provides in the first embodiment.

FIG. 31 is a diagram illustrating still another example of the reception unit that the display control function 152 provides in the first embodiment.

As illustrated in FIG. 31, the display control function 152, for example, displays guide information 8 corresponding to the medical examination data space on the display screen so as to enable the operator to grasp a position of the data display format being displayed in the medical examination data space. The display control function 152 displays as the guide information 8, for example, icons indicating presence and absence of the pieces of medical examination data in a display format in which the transverse axis indicates the times series and the longitudinal axis is the data type. The display control function 152 highlights the position corresponding to the medical examination data being currently displayed in the guide information 8. The display control function 152 may perform highlight display using colors, icons, and the like in order to display axes of equal to or higher than the two dimensions.

The display control function 152 may dynamically switch the axes that are displayed as the guide information 8 in accordance with the medical examination data being displayed, for example. When the display control function 152 displays a plane in the depth direction and the time direction for medical examination data related to the image, for example, the longitudinal axis is set to the axis of depth instead of the data type.

The display control function 152 may receive, on the guide information 8, an operation of specifying the pre-conversion state, the conversion reference point, and the conversion direction by the operator, for example. In this case, the display control function 152, for example, highlights the data display format being displayed that corresponds to a selected position on the guide information 8. The operator can thereby select the pre-conversion state and the conversion reference point intuitively.

Next, the converting function 153 will be described. The converting function 153 acquires respective coordinates of the pre-conversion state, the conversion reference point, and the conversion direction specified by the operator and performs the space conversion on the basis of the respective acquired coordinates to calculate coordinates indicating the post-conversion state.

Figure 32:
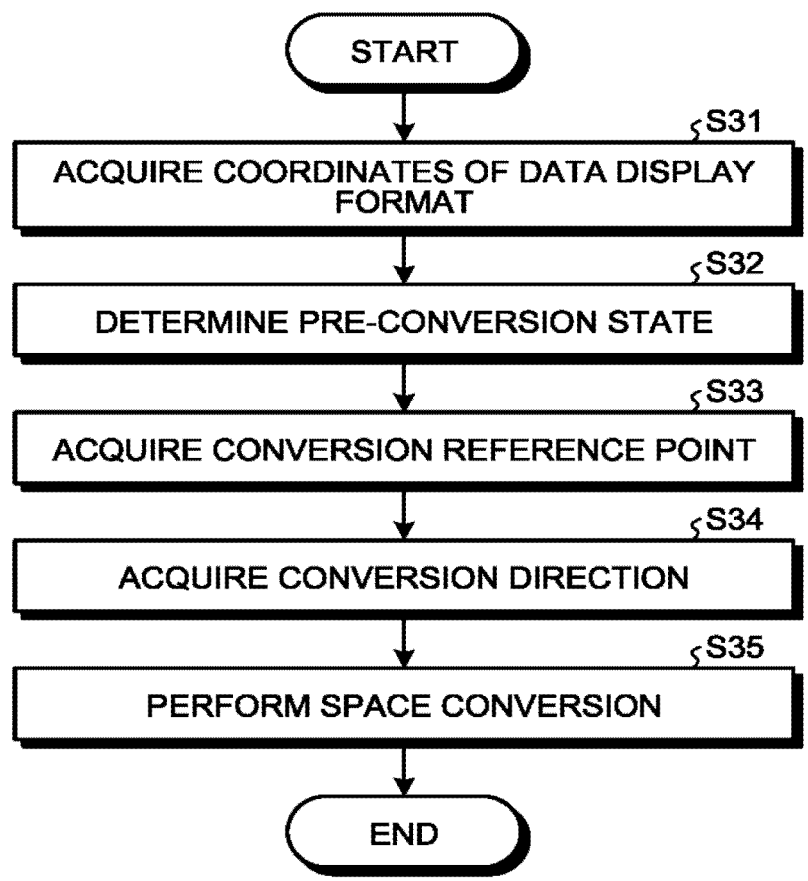
FIG. 32 is a flowchart illustrating flow of processing that the converting function performs in the first embodiment.

FIG. 32 is a flowchart illustrating flow of processing that the converting function 153 performs in the first embodiment.

As illustrated in FIG. 32, for example, the converting function 153 first acquires the coordinates of the data display formats being displayed on the display screen (step S31). In this case, the converting function 153 acquires the coordinates in the medical examination data space on the basis of the display coordinate master table of the display coordinate master for all of the data display formats that the operator has specified as the pre-conversion state using the reception unit provided by the display control function 152. For example, when the data display format provided by collecting the data display formats is specified, the converting function 153 acquires the coordinates for all of the data display formats contained in the data display format. Alternatively, the converting function 153 may acquire the coordinates for all of the data display formats that the display control function 152 displays on the display screen.

Then, the converting function 153 determines the pre-conversion state (step S32). In this case, the converting function 153 determines a display state of the data display formats selected by the operator or the data display formats being displayed on the display screen on the basis of the acquired coordinates. The converting function 153 sets the coordinates indicating the determined display state as the coordinates indicating the pre-conversion state.

FIGS. 33 to 37 are diagrams illustrating examples of the determination of the display state by the converting function 153 in the first embodiment.

Figure 33:
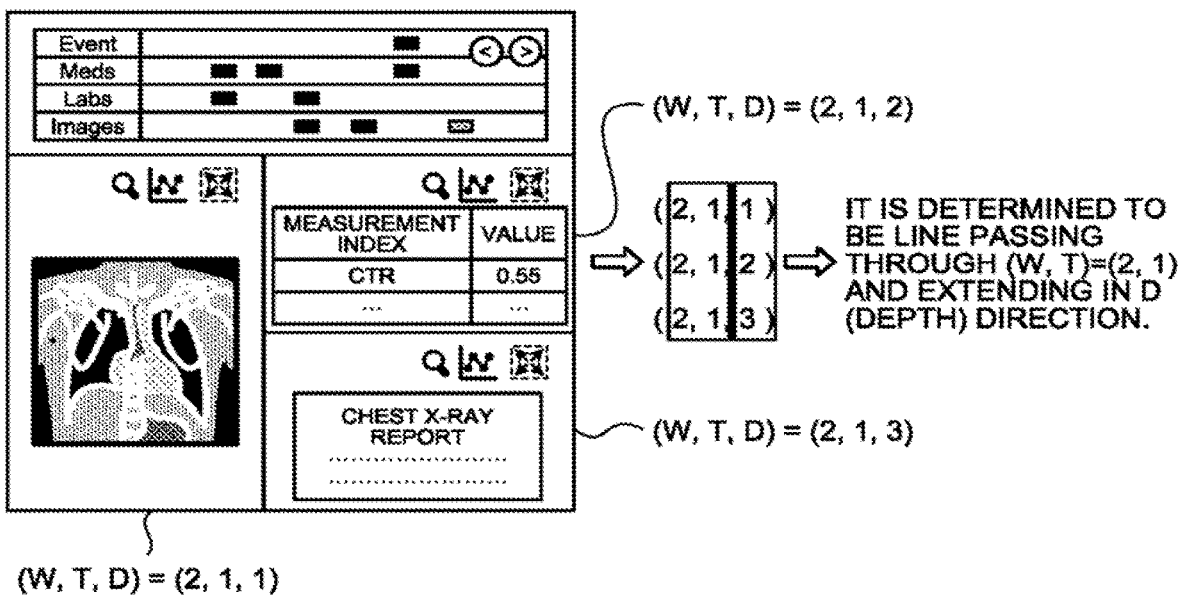
FIG. 33 is a diagram illustrating an example of determination of a display state by the converting function in the first embodiment.

For example, it is assumed that the data display format of (W,T,D)=(2,1,1), the data display format of (W,T,D)=(2,1,2), and the data display format of (W,T,D)=(2,1,3) are displayed on the display screen, as illustrated on the left side in FIG. 33. In this case, for example, as illustrated on the right side in FIG. 33, the converting function 153 determines that the display state of these data display formats is a line passing through (W,T)=(2,1) and extending in the D (depth) direction. The converting function 153 sets (W,T,D)=(2,1,*) as the coordinates indicating the pre-conversion state in this case.

Figure 34:
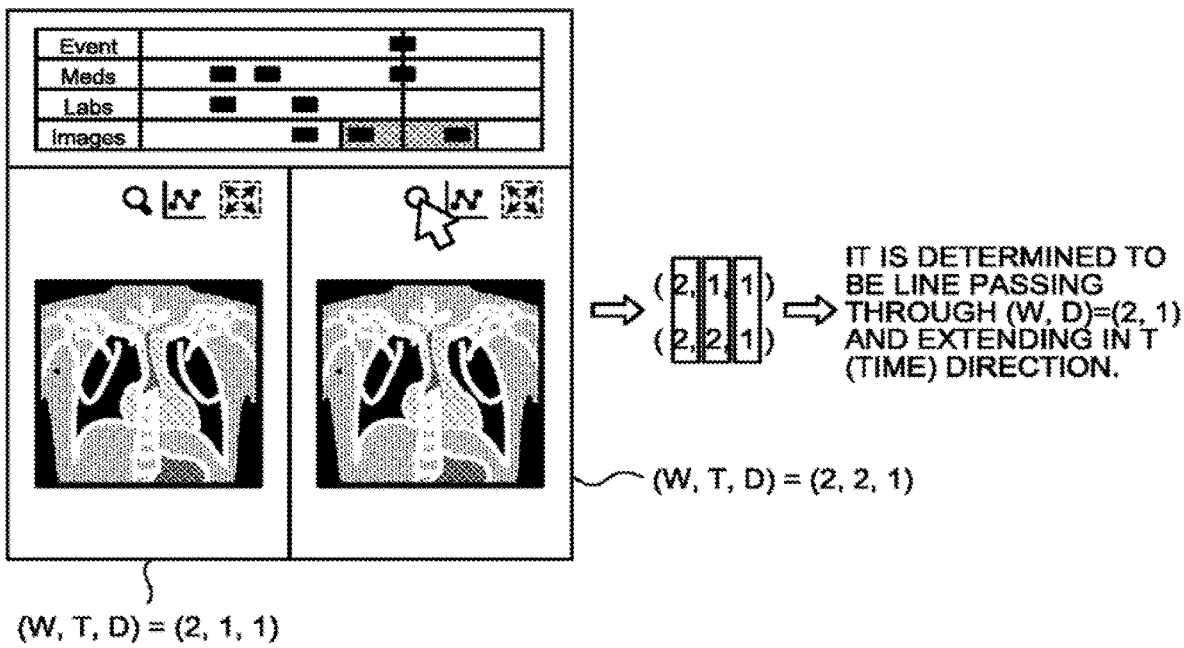
FIG. 34 is a diagram illustrating another example of the determination of the display state by the converting function in the first embodiment.

For example, it is assumed that the data display format of (W,T,D)=(2,1,1) and the data display format of (W,T,D)=(2,2,1) are displayed on the display screen, as illustrated on the left side in FIG. 34. In this case, for example, as illustrated on the right side in FIG. 34, the converting function 153 determines that the display state of these data display formats is a line passing through (W,D)=(2,1) and extending in the T (time) direction. The converting function 153 sets (W,T,D)=(2,*,1) as the coordinates indicating the pre-conversion state in this case.

Figure 35:
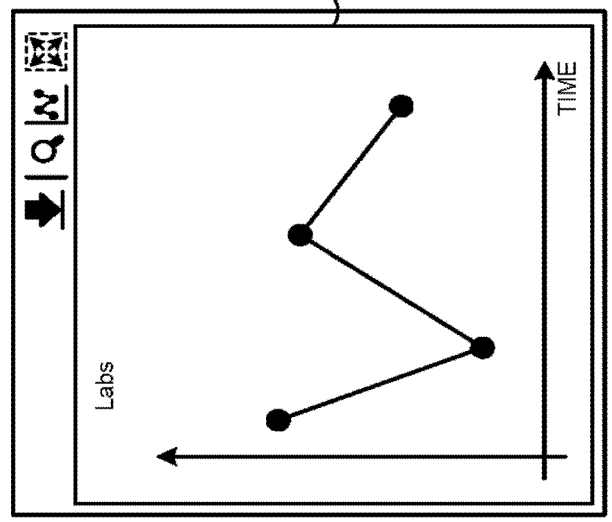
FIG. 35 is a diagram illustrating still another example of the determination of the display state by the converting function in the first embodiment.

For example, it is assumed that the data display format of (W,T,D)=(5,(1 to 4),2) is displayed on the display screen, as illustrated on the left side in FIG. 35. In this case, for example, as illustrated on the right side in FIG. 35, the converting function 153 determines that the display state of the data display format is a line passing through (W,D)=(5,2) and extending in the T (time) direction. The converting function 153 sets (W,T,D)=(5,*,2) as the coordinates indicating the pre-conversion state in this case.

Figure 36:
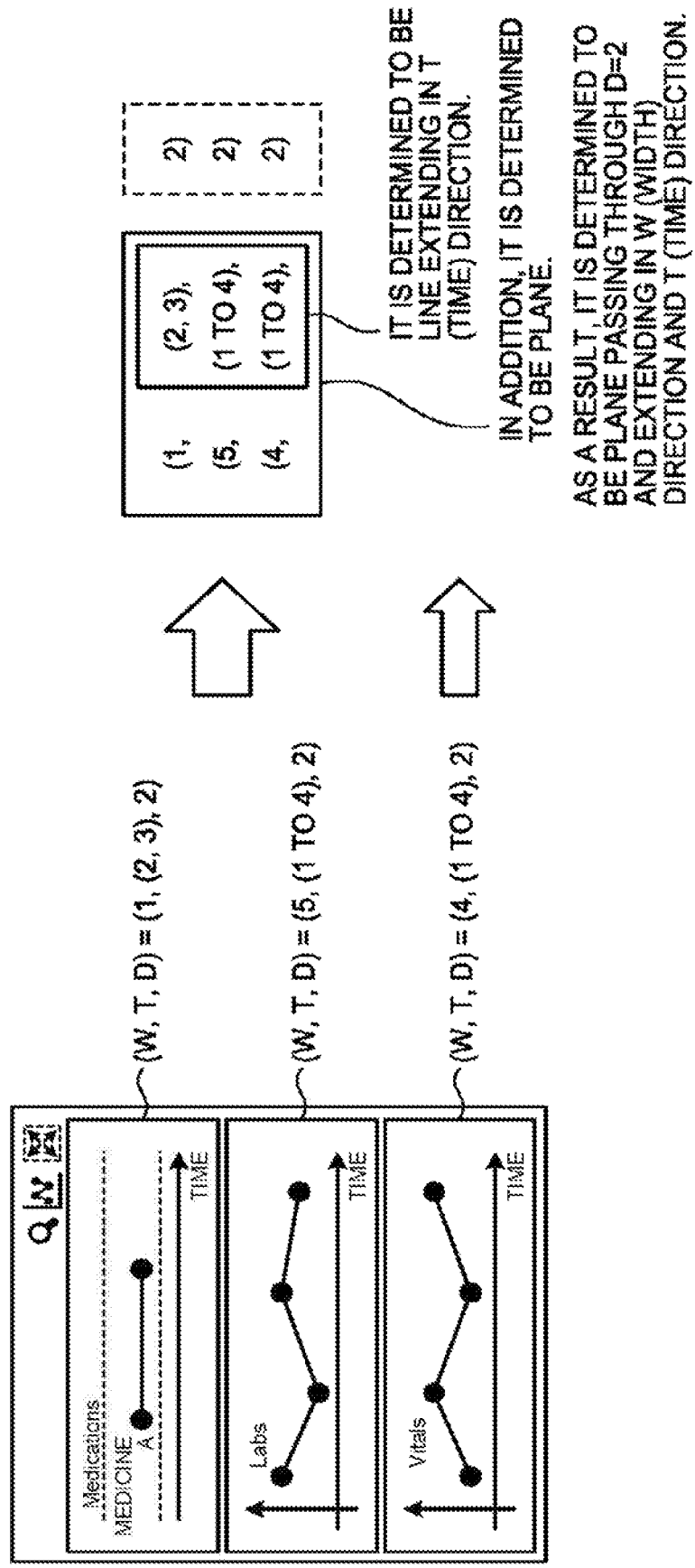
FIG. 36 is a diagram illustrating still another example of the determination of the display state by the converting function in the first embodiment.

For example, it is assumed that the data display format of (W,T,D)=(1,(2,3),2), the data display format of (W,T,D)=(5,(1 to 4),2), and the data display format of (W,T,D)=(4,(1 to 4),2) are displayed on the display screen, as illustrated on the left side in FIG. 36. In this case, for example, as illustrated on the right side in FIG. 36, the converting function 153 first determines that the first data display format is a line passing through (W,D)=(1,2) and extending in the T (time) direction, the second data display format is a line passing through (W,D)=(5,2) and extending in the T (time) direction, and the third data display format is a line passing through (W,D)=(4,2) and extending in the T (time) direction. In addition, the converting function 153 determines that the display state of these data display formats is a plane passing through D=2 and extending in the W (width) direction and the T (time) direction. The converting function 153 sets (W,T,D)=(*,*,2) as the coordinates indicating the pre-conversion state in this case.

Figure 37:
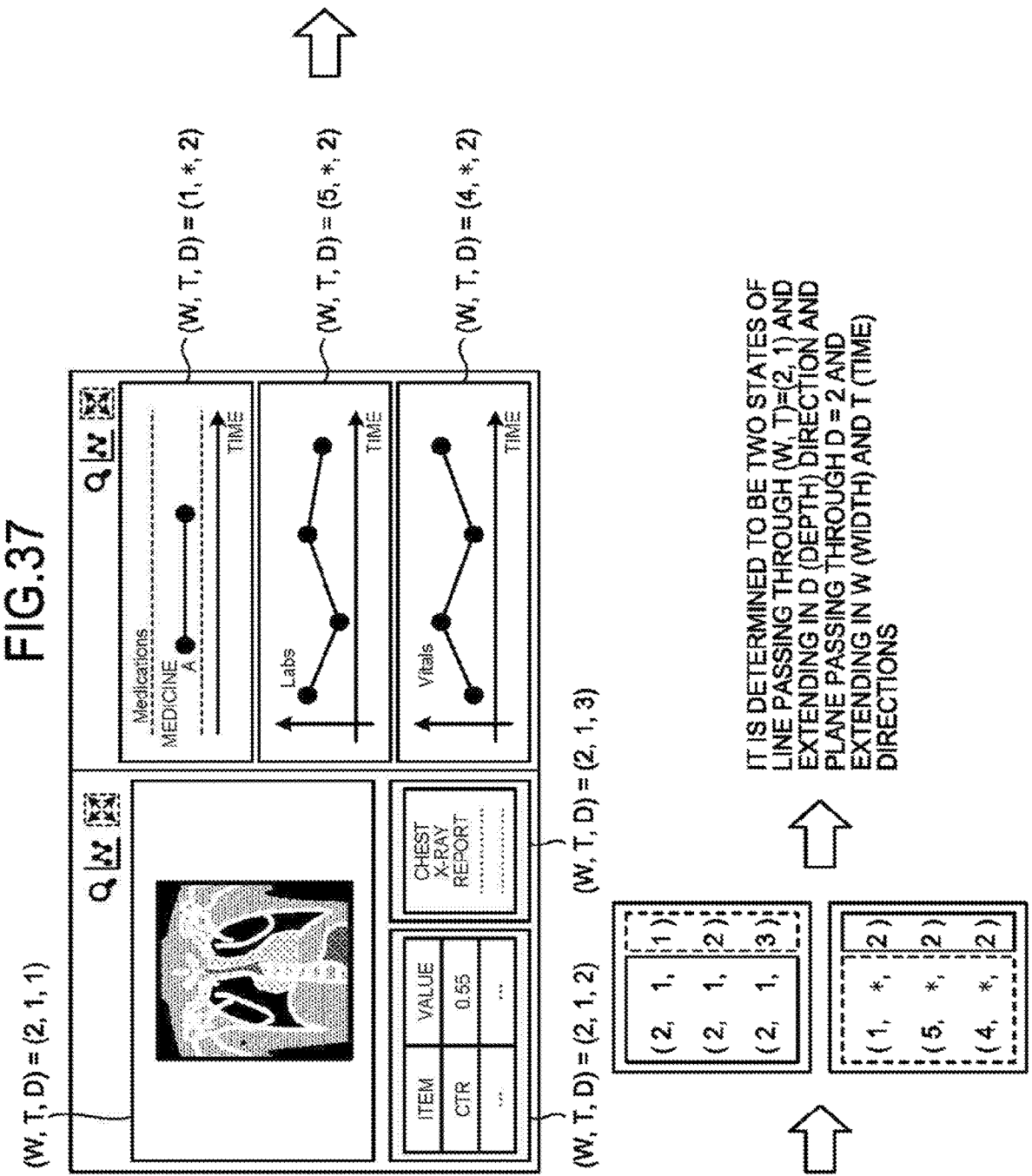
FIG. 37 is a diagram illustrating still another example of the determination of the display state by the converting function in the first embodiment.

For example, it is assumed that the data display format of (W,T,D)=(2,1,1), the data display format of (W,T,D)=(2,1,2), the data display format of (W,T,D)=(2,1,3), the data display format of (W,T,D)=(1,*,2), the data display format of (W,T,D)=(5,*,2), and the data display format of (W,T,D)=(4,*,2) are displayed on the display screen, as illustrated on the left side in FIG. 37. In this case, for example, as illustrated on the right side in FIG. 37, the converting function 153 determines that the display states of these data display formats are two states of a line passing through (W,T)=(2,1) and extending in the D (depth) direction and a plane passing through D=2 and extending in the W (width) and T (time) directions. The converting function 153 sets (W,T,D)=(2,1,*) and (W,T,D)=(*,*,2) as the coordinates indicating the pre-conversion state in this case.

With reference to FIG. 32 again, the converting function 153 subsequently acquires the conversion reference point (step S33). In this case, the converting function 153 acquires coordinates in the medical examination data space on the basis of the display coordinate master table of the display coordinate master for the data display format that the operator has specified as the conversion reference point using the reception unit provided by the display control function 152. The converting function 153 sets the acquired coordinates as the coordinates indicating the conversion reference point.

Then, the converting function 153 acquires the conversion direction (step S34). In this case, the converting function 153 sets, as the coordinates indicating the conversion direction, coordinates indicating the direction that the operator has specified as the conversion direction using the reception unit provided by the display control function 152.

Figure 38:
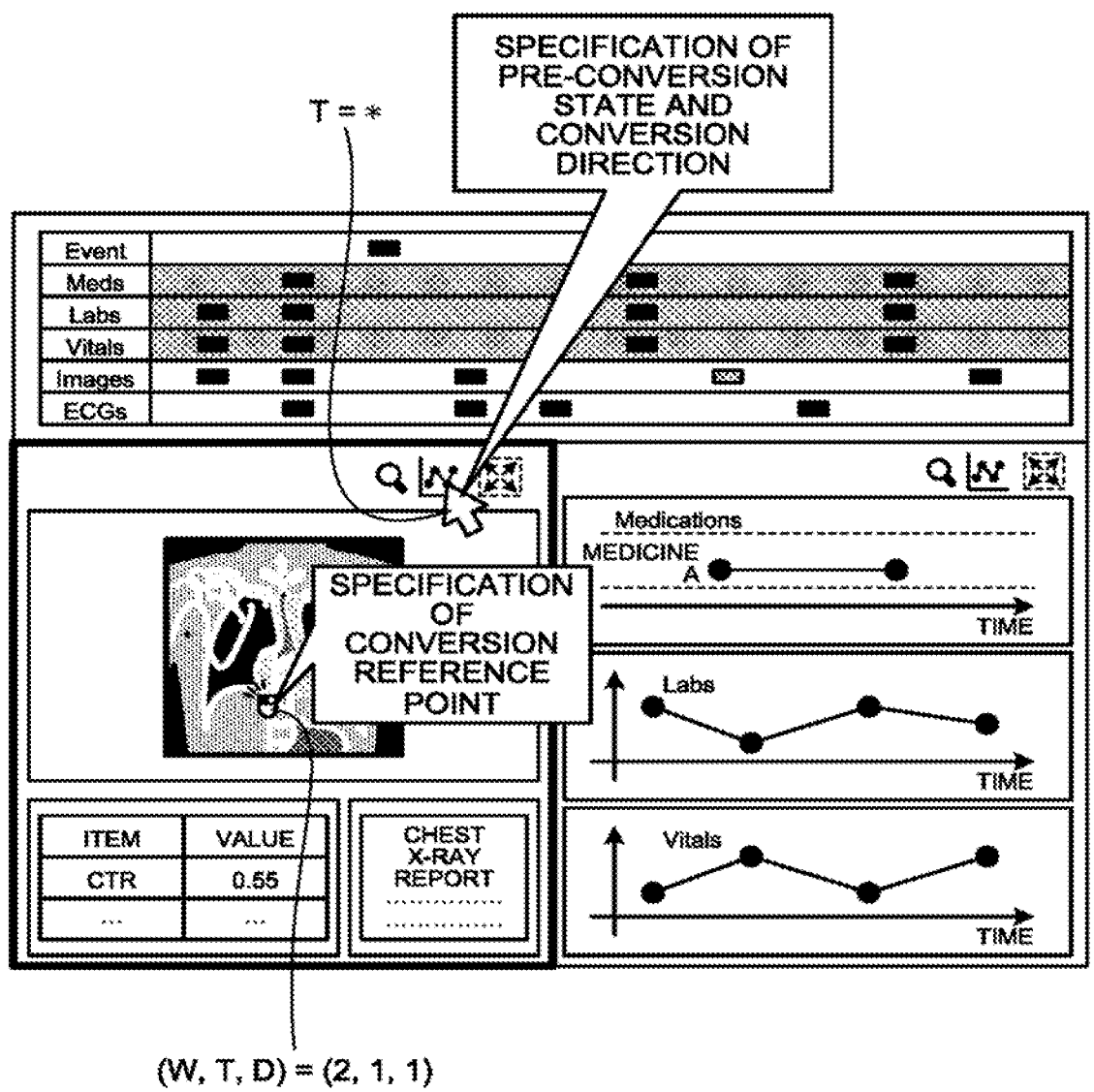
FIG. 38 is a diagram illustrating an example of acquisition of a conversion reference point and a conversion direction by the converting function in the first embodiment.

FIG. 38 is a diagram illustrating an example of acquisition of the conversion reference point and the conversion direction by the converting function 153 in the first embodiment.

For example, it is assumed that the operator specifies a data display format of (W,T,D)=(2,1,1) as the conversion reference point, as illustrated in FIG. 38. In this case, the converting function 153 acquires the corresponding coordinates (2,1,1) from the display coordinate master on the basis of the data display ID of the data display format. The converting function 153 sets T=* indicating a line extending in the T (time) direction as the coordinates indicating the conversion direction when the operator specifies the time direction as the conversion direction.

With reference to FIG. 32 again, the converting function 153 subsequently performs the space conversion (step S35). In this case, the converting function 153 calculates coordinates indicating the post-conversion state on the basis of the coordinates indicating the pre-conversion state, the coordinates indicating the conversion reference point, and the coordinates indicating the conversion direction provided by the above-mentioned pieces of processing.

Figure 39:
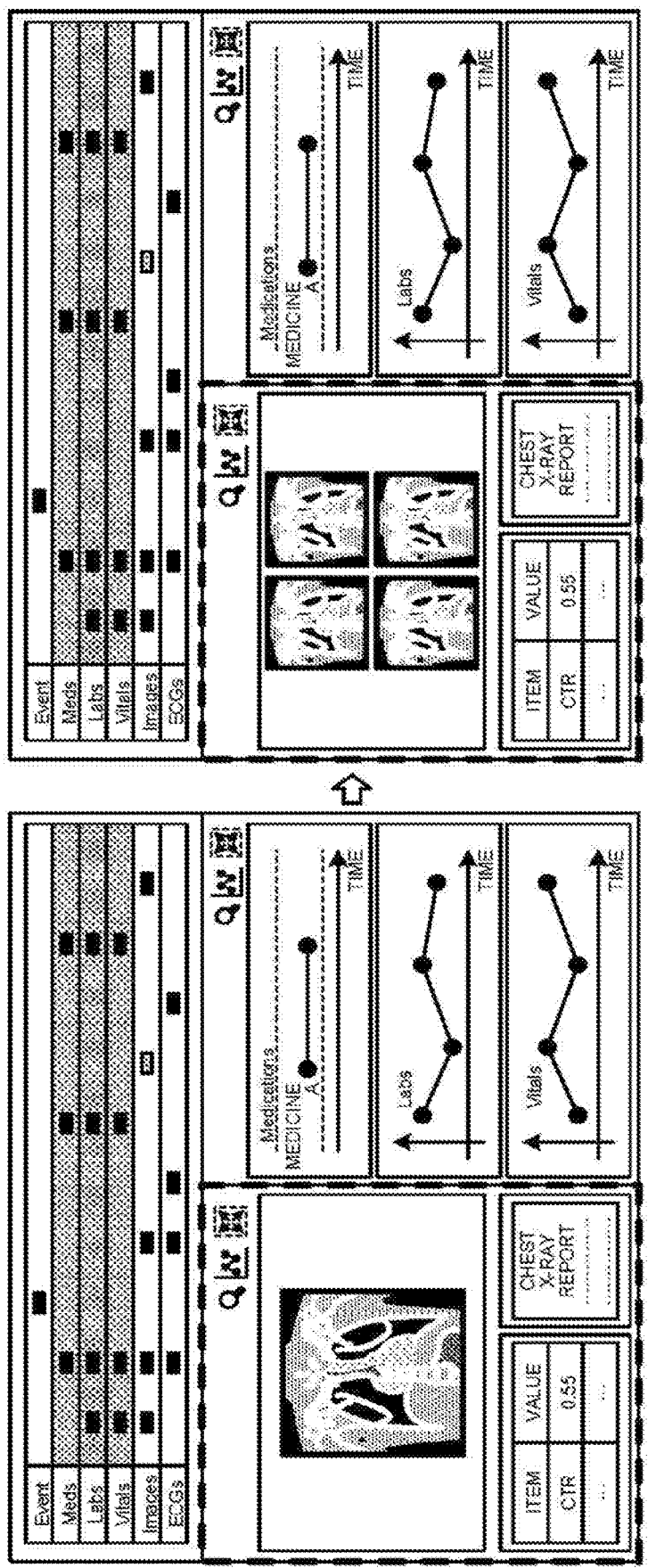
FIG. 39 is a diagram illustrating an example of calculation of coordinates indicating a post-conversion state by the converting function in the first embodiment.

FIG. 39 is a diagram illustrating an example of calculation of the coordinates indicating the post-conversion state by the converting function 153 in the first embodiment.

For example, it is assumed that the coordinates indicating the pre-conversion state are (W,T,D)=(2,1,*), the coordinates indicating the conversion reference point are (W,T,D)=(2,1,1), and the coordinate indicating the conversion direction is T=*, as illustrated on the upper side in FIG. 39. The converting function 153 calculates (W,T,D)=(2,*,1) as the coordinates indicating the post-conversion state in this case.

That is to say, in the example illustrated in FIG. 39, the pre-conversion state indicated by a line passing through (W,T)=(2,1) and extending in the D (depth) direction is subject to the space conversion in the conversion direction indicated by a line extending in the T (time) direction with reference to the conversion reference point indicated by a point of (W,T,D)=(2,1,1). With this space conversion, the pre-conversion state is converted into the post-conversion state indicated by a line passing through (W,D)=(2,1) and extending in the T (time) direction.

As a result, for example, as illustrated on the lower side in FIG. 39, the display control function 152 switches the state before the conversion in which the image data, the image measurement values, and the image reading report are displayed for one time point to a state after the conversion in which pieces of image data are displayed for a plurality of time points, and the time measurement values and the image reading report are displayed for the one time point.

The converting function 153 thus converts, as the space conversion, the pre-conversion state indicated by a point, line, or plane into the post-conversion state indicated by another point, line, or plane with reference to the conversion reference point specified in the pre-conversion state. The conversion reference point is also indicated by a point, line, or plane in the medical examination data space.

To be specific, the converting function 153 performs rotation, parallel movement, or magnification or reduction in the medical examination data space as the space conversion.

Hereinafter, the space conversion that the converting function 153 performs in the first embodiment will be described using specific examples.

FIG. 40 is a diagram illustrating an example of magnification conversion that the converting function 153 performs in the first embodiment. FIG. 40 illustrates an example of the case in which a point is converted into a line for display by magnification.

For example, it is assumed that the operator specifies a data display format of $(W,T,D)=(W_A,T_A,D_A)$ as the pre-conversion state and the conversion reference point and specifies the depth direction (D=*) as the conversion direction, as illustrated on the left side in FIG. 40. In this case, for example, as illustrated on the right side in FIG. 40, the converting function 153 converts the coordinates $(W_A,T_A,D_A)$ indicating the pre-conversion state into coordinates $(W_A,T_A,*)$ indicating the post-conversion state.

The above-mentioned space conversion corresponds to conversion of the pre-conversion state indicated by a point into the post-conversion state indicated by a line extending in the depth direction by the magnification in the depth direction with reference to the conversion reference point indicated by the above-mentioned point.

As a result, for example, as illustrated in FIG. 40, the display control function 152 switches the state before the conversion in which image data is displayed for one time point to a state after the conversion in which the image data, an image measurement value, and an image reading report are displayed for the same time point.

FIG. 41 is a diagram illustrating another example of the magnification conversion that the converting function 153 performs in the first embodiment. FIG. 41 illustrates an example of the case in which a line is converted into a plane for display by magnification.

For example, it is assumed that the operator specifies a data display format of $(W,T,D)=(W_B,*,D_B)$ as the pre-conversion state and the conversion reference point and specifies the width direction (W=*) as the conversion direction, as illustrated on the left side in FIG. 41. In this case, for example, as illustrated on the right side in FIG. 41, the converting function 153 converts the coordinates $(W_B,*,D_B)$ indicating the pre-conversion state into coordinates $(*,*,D_B)$ indicating the post-conversion state.

The above-mentioned space conversion corresponds to conversion of the pre-conversion state indicated by a line extending in the time direction into the post-conversion state indicated by a plane extending in the width direction and the time direction by the magnification in the width direction with reference to the conversion reference point indicated by the above-mentioned line.

As a result, for example, as illustrated in FIG. 41, the display control function 152 switches the state before the conversion in which pieces of specimen inspection summary data are displayed for a plurality of time points to a state after the conversion in which pieces of medication summary data, the pieces of specimen inspection summary data, and pieces of vital summary data are displayed for the time points.

Figure 42:
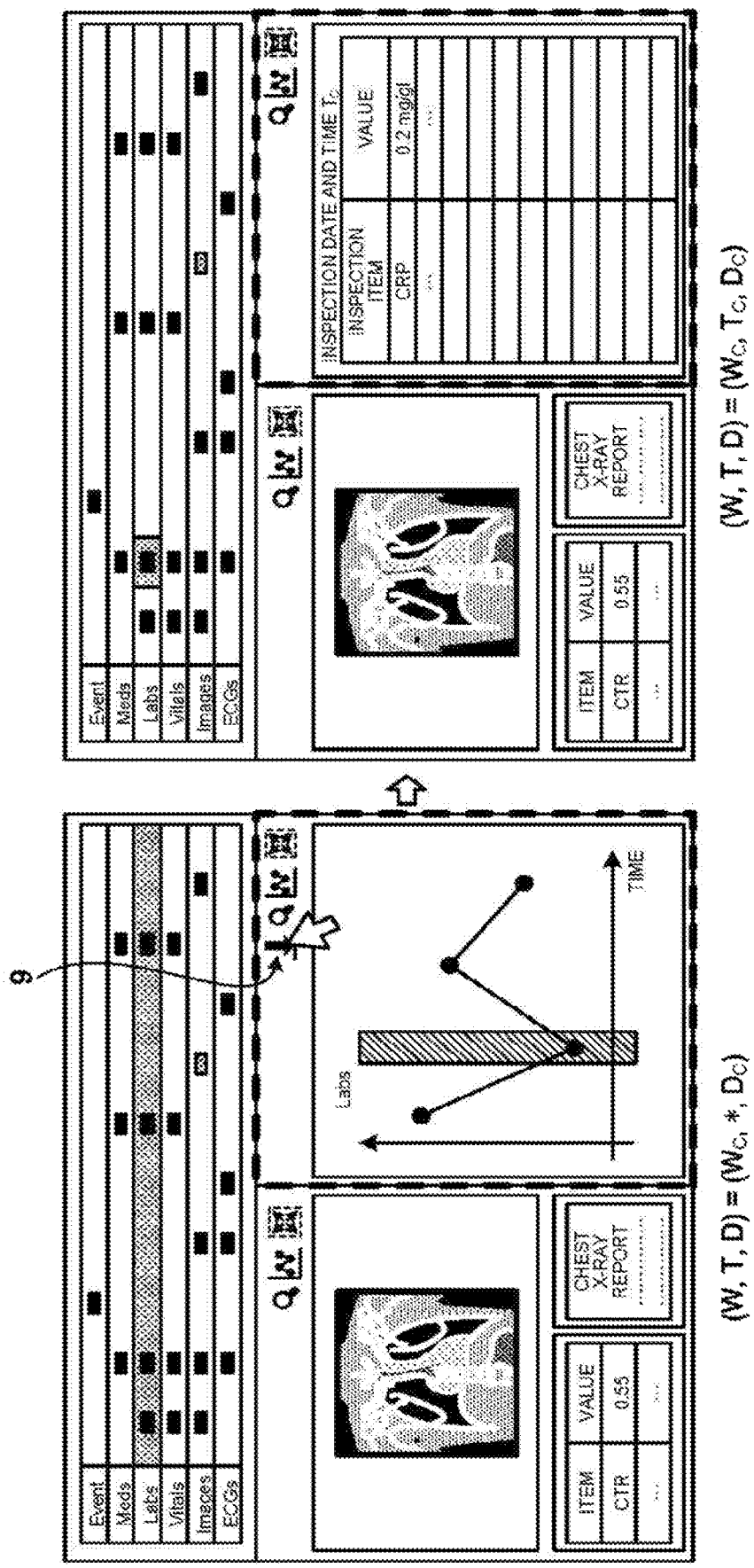
FIG. 42 is a diagram illustrating an example of reduction conversion that the converting function performs in the first embodiment.

FIG. 42 is a diagram illustrating an example of reduction conversion that the converting function 153 performs in the first embodiment. FIG. 42 illustrates an example of the case in which a line is converted into a point for display by reduction.

In the example illustrated in FIG. 42, in addition to the three icons for specifying the conversion direction, an icon 9 for specifying reduction in a specified direction is further arranged on the data display format.

For example, it is assumed that the operator specifies a data display format of $(W,T,D)=(W_C,*,D_C)$ as the pre-conversion state, specifies a position of $(W,T,D)=(W_C,T_C,D_C)$ as the conversion reference point, specifies the time direction $(T=*)$ as the conversion direction, and further specifies reduction in the direction, as illustrated on the left side in FIG. 42. In this case, for example, as illustrated on the right side in FIG. 42, the converting function 153 converts the coordinates $(W_C,*,D_C)$ indicating the pre-conversion state into coordinates $(W_C,T_C,D_C)$ indicating the post-conversion state.

The above-mentioned space conversion corresponds to conversion of the pre-conversion state indicated by a line extending in the time direction into the post-conversion state indicated by a point by the reduction in the time direction with reference to the conversion reference point indicated by one point contained in the above-mentioned line.

As a result, for example, as illustrated in FIG. 42, the display control function 152 switches the state before the conversion in which pieces of specimen inspection summary data are displayed for a plurality of time points to a state after the conversion in which specimen inspection measurement values is displayed for one time point of the time points.

Figure 43:
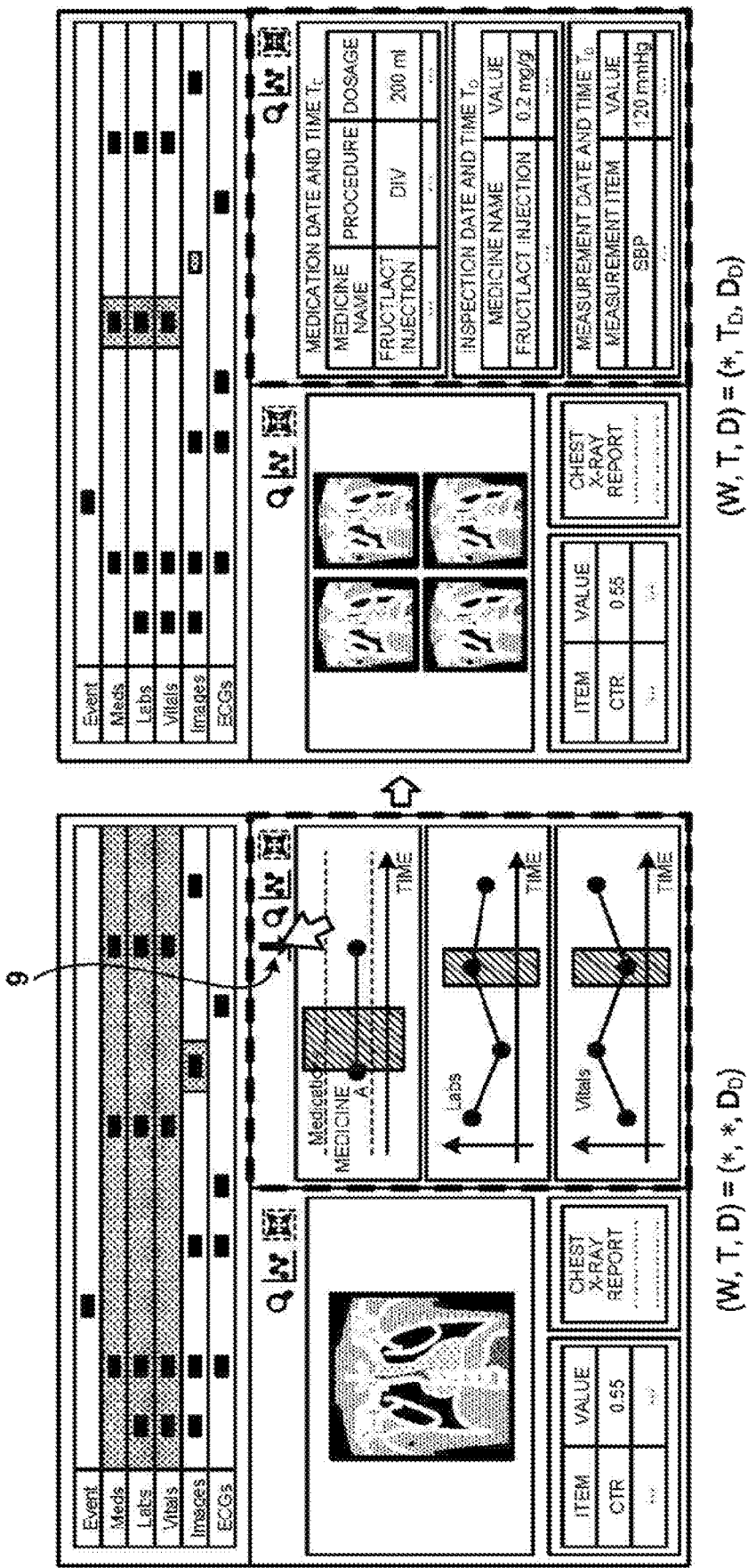
FIG. 43 is a diagram illustrating another example of the reduction conversion that the converting function performs in the first embodiment.

FIG. 43 is a diagram illustrating another example of the reduction conversion that the converting function 153 performs in the first embodiment. FIG. 43 illustrates an example of the case in which a plane is converted into a line for display by reduction.

Also in the example illustrated in FIG. 43, in addition to the three icons for specifying the conversion direction, the icon 9 for specifying reduction in a specified direction is further arranged on the data display format.

For example, it is assumed that the operator specifies a data display format of $(W,T,D)=(*,*,D_D)$ as the pre-conversion state, specifies a position of $(W,T,D)=(*,T_D,D_D)$ as the conversion reference point, specifies the time direction $(T=*)$ as the conversion direction, and further specifies reduction in the direction, as illustrated on the left side in FIG. 43. In this case, for example, as illustrated on the right side in FIG. 43, the converting function 153 converts the coordinates $(*,*,D_D)$ indicating the pre-conversion state into coordinates $(*,T_D,D_D)$ indicating the post-conversion state.

The above-mentioned space conversion corresponds to conversion of the pre-conversion state indicated by a plane extending in the width direction and the time direction into the post-conversion state indicated by a line extending in the width direction by the reduction in the time direction with reference to the conversion reference point indicated by one line extending in the width direction that is contained in the above-mentioned plane.

As a result, for example, as illustrated in FIG. 43, the display control function 152 switches the state before the conversion in which pieces of medication summary data, pieces of specimen inspection summary data, and pieces of vital summary data are displayed for a plurality of time points to a state after the conversion in which information indicating a medicine, specimen inspection measurement values, and vital measurement values are displayed for one time point of the time points.

Figure 44:
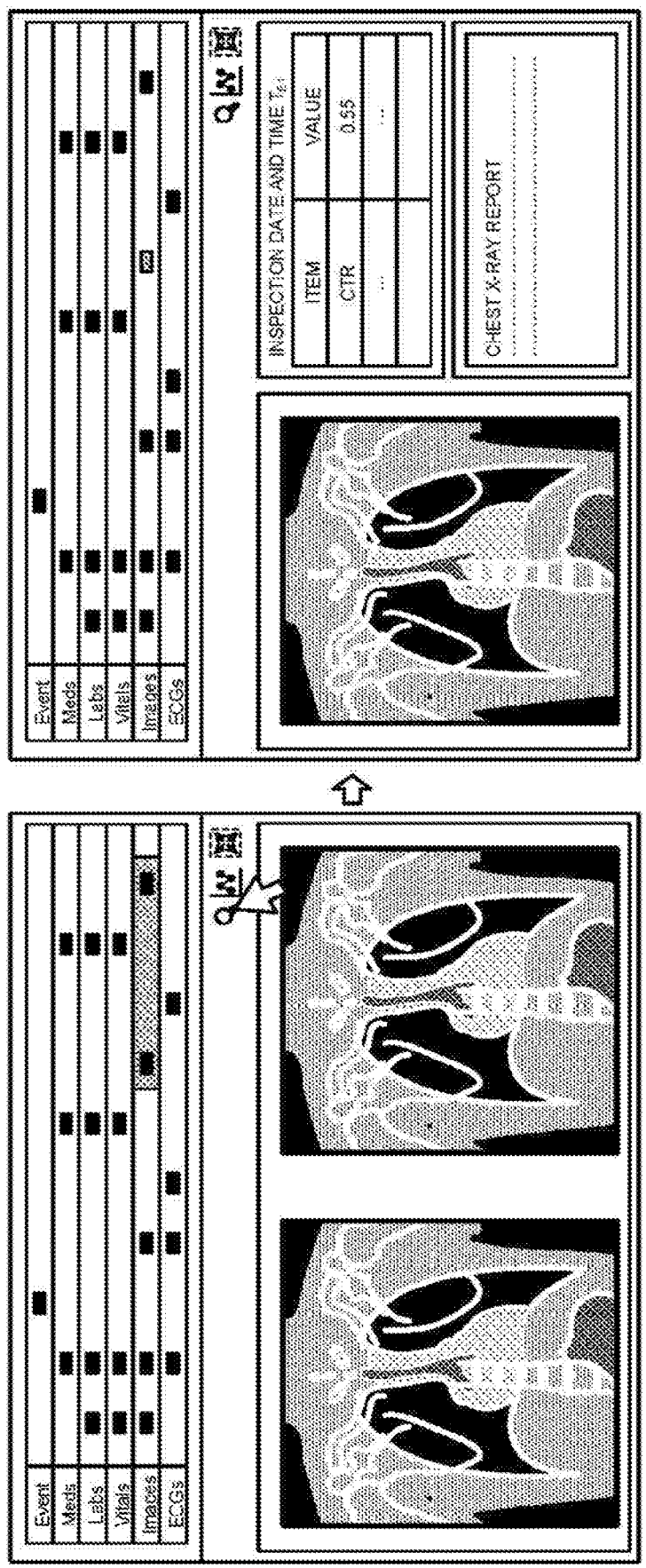
FIG. 44 is a diagram illustrating an example of rotation conversion that the converting function performs in the first embodiment.

FIG. 44 is a diagram illustrating an example of rotation conversion that the converting function 153 performs in the first embodiment. FIG. 44 illustrates an example of the case in which a line is subject to the rotation conversion.

For example, it is assumed that the operator specifies a data display format of $(W,T,D)=(W_{E1},*,D_{E1})$ as the pre-conversion state, specifies a position of $(W,T,D)=(W_{E1},T_{E1},D_{E1})$ as the conversion reference point, and specifies the depth direction $(D=*)$ as the conversion direction, as illustrated on the left side in FIG. 44. In this case, for example, as illustrated on the right side in FIG. 44, the converting function 153 converts the coordinates $(W_{E1},*,D_{E1})$ indicating the pre-conversion state into coordinates $(W_{E1},T_{E1},*)$ indicating the post-conversion state.

The above-mentioned space conversion corresponds to conversion of the pre-conversion state indicated by a line extending in the time direction into the post-conversion state indicated by a line extending in the depth direction by the rotation in the depth direction with reference to the conversion reference point indicated by one point contained in the above-mentioned line.

As a result, for example, as illustrated in FIG. 44, the display control function 152 switches the state before the conversion in which pieces of image data are displayed for a plurality of time points to a state after the conversion in which image data, an image measurement value, and an image reading report are displayed for one time point of the time points.

Figure 45:
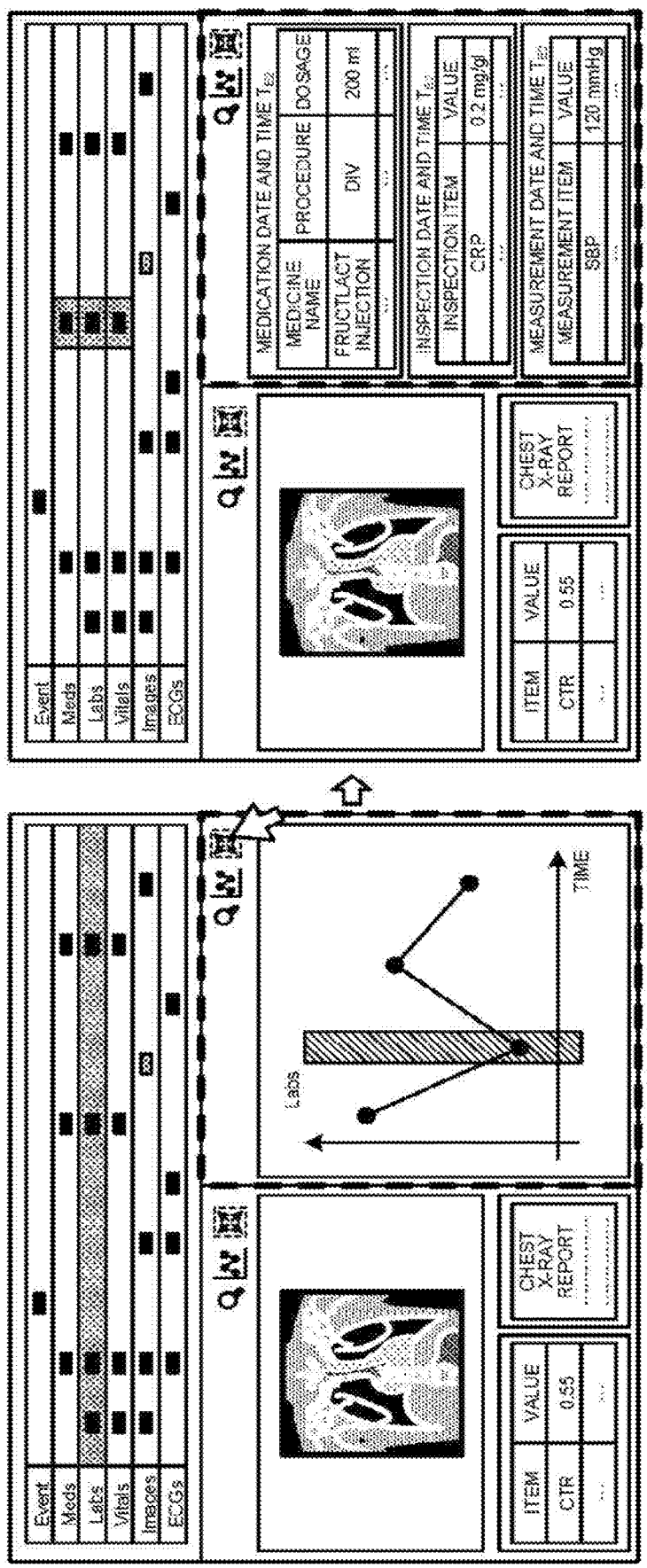
FIG. 45 is a diagram illustrating another example of the rotation conversion that the converting function performs in the first embodiment.

FIG. 45 is a diagram illustrating another example of the rotation conversion that the converting function 153 performs in the first embodiment. FIG. 45 illustrates another example of the case in which a line is subject to the rotation conversion.

For example, it is assumed that the operator specifies a data display format of $(W,T,D)=(W_{E2},*,D_{E2})$ as the pre-conversion state, specifies a position of $(W,T,D)=(W_{E2},T_{E2},D_{E2})$ as the conversion reference point, and specifies the width direction $(W=*)$ as the conversion direction, as illustrated on the left side in FIG. 45. In this case, for example, as illustrated on the right side in FIG. 45, the converting function 153 converts the coordinates $(W_{E2},*,D_{E2})$ indicating the pre-conversion state into coordinates $(*,T_{E2},D_{E2})$ indicating the post-conversion state.

The above-mentioned space conversion corresponds to conversion of the pre-conversion state indicated by a line extending in the time direction into the post-conversion state indicated by a line extending in the width direction by the rotation in the width direction with reference to the conversion reference point indicated by one point contained in the above-mentioned line.

As a result, for example, as illustrated in FIG. 45, the display control function 152 switches the state before the conversion in which pieces of specimen inspection summary data are displayed for a plurality of time points to a state after the conversion in which information indicating a medicine, specimen inspection measurement values, and vital measurement values are displayed for one time point of the time points.

Figure 46:
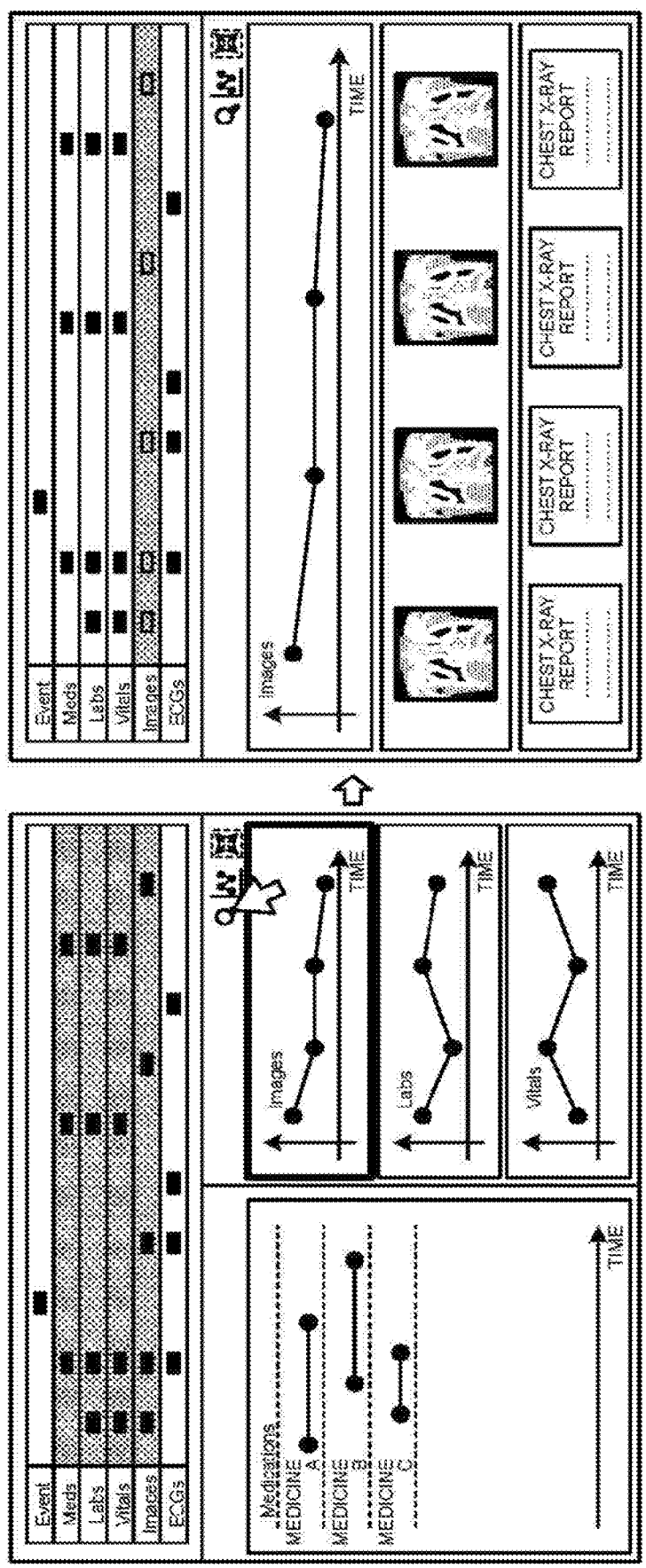
FIG. 46 is a diagram illustrating still another example of the rotation conversion that the converting function performs in the first embodiment.

FIG. 46 is a diagram illustrating still another example of the rotation conversion that the converting function 153 performs in the first embodiment. FIG. 46 illustrates an example of the case in which a plane is subject to the rotation conversion.

For example, it is assumed that the operator specifies a data display format of (W,T,D)=(*,*,$D_{F1}$) as the pre-conversion state, specifies a position of (W,T,D)=($W_{F1}$,*,$D_{F1}$) as the conversion reference point, and specifies the depth direction (D=*) as the conversion direction, as illustrated on the left side in FIG. 46. In this case, for example, as illustrated on the right side in FIG. 46, the converting function 153 converts coordinates (*,*,$D_{F1}$) indicating the pre-conversion state into coordinates ($W_{F1}$,*,*) indicating the post-conversion state.

The above-mentioned space conversion corresponds to conversion of the pre-conversion state indicated by a plane extending in the width direction and the time direction into the post-conversion state indicated by a plane extending in the time direction and the depth direction by the rotation in the depth direction with reference to the conversion reference point indicated by one line extending in the time direction that is contained in the above-mentioned plane.

As a result, for example, as illustrated in FIG. 46, the display control function 152 switches the state before the conversion in which image measurement values, pieces of specimen inspection summary data, and pieces of vital summary data are displayed for a plurality of time points to a state after the conversion in which image measurement values, pieces of image data, and image reading reports are displayed for the time points.

Figure 47:
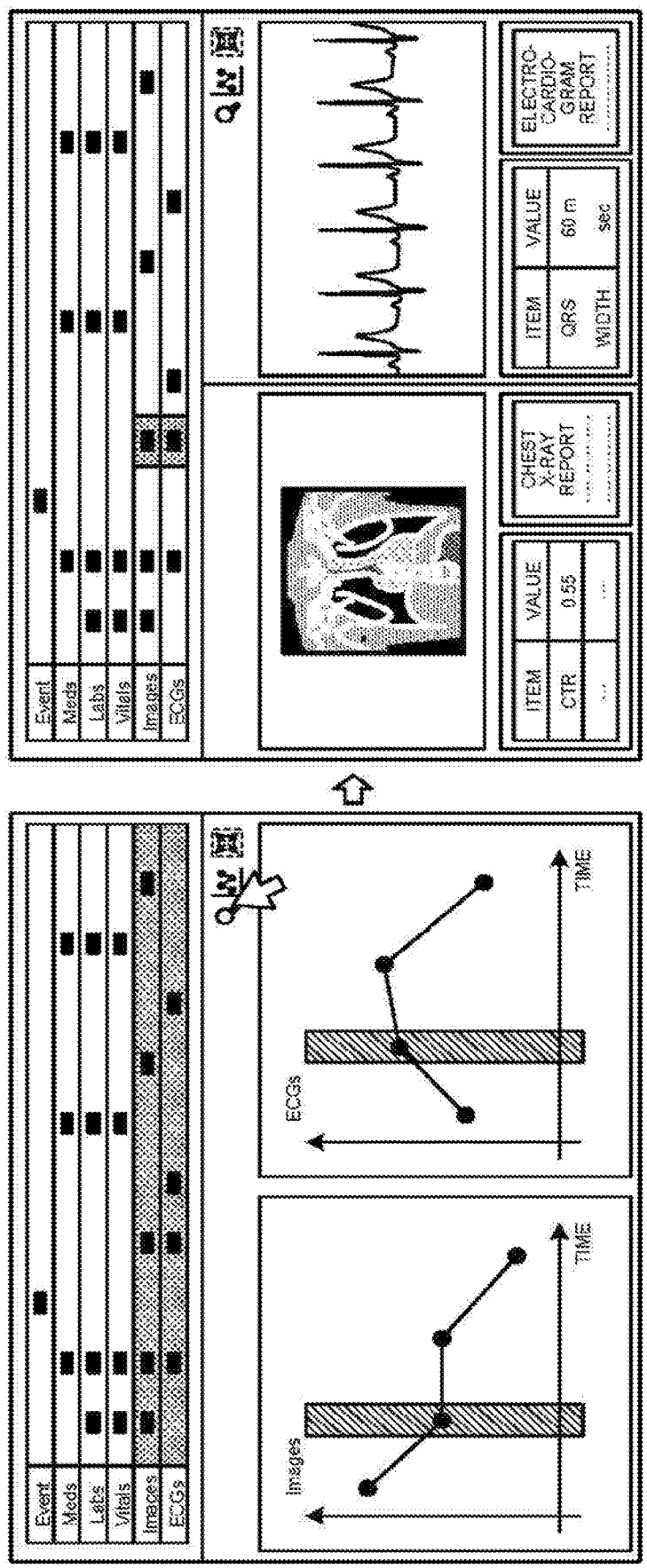
FIG. 47 is a diagram illustrating still another example of the rotation conversion that the converting function performs in the first embodiment.

FIG. 47 is a diagram illustrating still another example of the rotation conversion that the converting function 153 performs in the first embodiment. FIG. 47 illustrates another example of the case in which a plane is subject to the rotation conversion.

For example, it is assumed that the operator specifies a data display format of (W,T,D)=(*,*,$D_{F2}$) as the pre-conversion state, specifies a position of (W,T,D)=(*,$T_{F2}$,$D_{F2}$) as the conversion reference point, and specifies the depth direction (D=*) as the conversion direction, as illustrated on the left side in FIG. 47. In this case, for example, as illustrated on the right side in FIG. 47, the converting function 153 converts coordinates (*,*,$D_{F2}$) indicating the pre-conversion state into coordinates (*,$T_{F2}$,*) indicating the post-conversion state.

The above-mentioned space conversion corresponds to conversion of the pre-conversion state indicated by a plane extending in the width direction and the time direction into the post-conversion state indicated by a plane extending in the width direction and the depth direction by the rotation in the depth direction with reference to the conversion reference point indicated by one line extending in the width direction that is contained in the above-mentioned plane.

As a result, for example, as illustrated in FIG. 47, the display control function 152 switches the state before the conversion in which image measurement values and electrocardiogram measurement values are displayed for a plurality of time points to a state after the conversion in which image data, an image measurement value, an image reading report, electrocardiogram image data, an electrocardiogram measurement value, and an electrocardiogram report are displayed for one time point of the time points.

Figure 48:
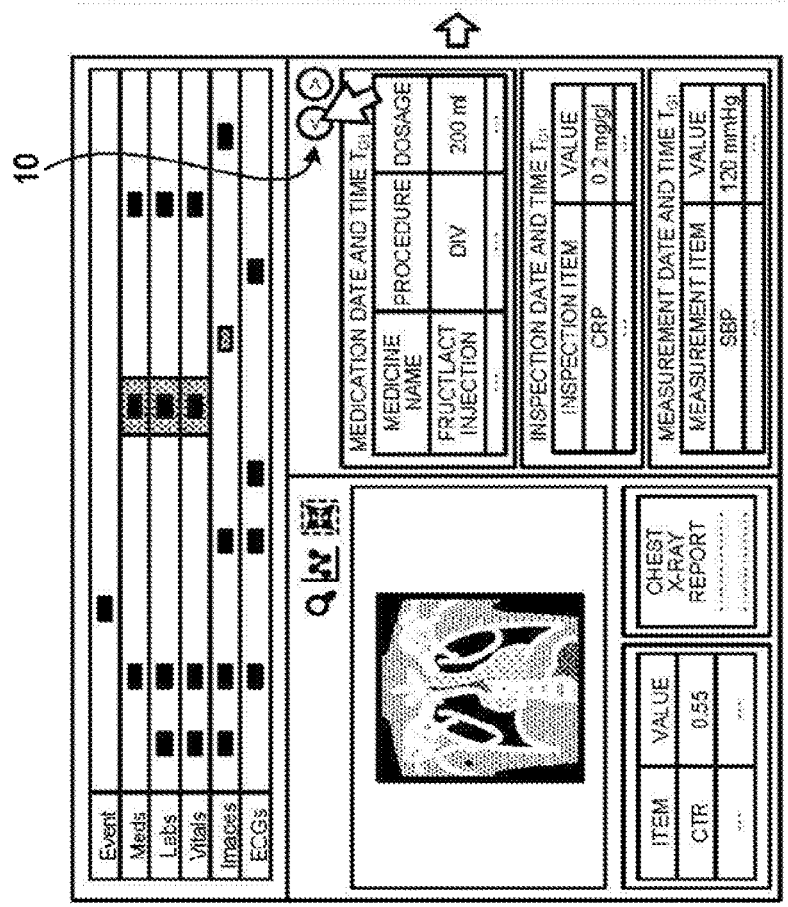
FIG. 48 is a diagram illustrating an example of parallel movement conversion that the converting function performs in the first embodiment.

FIG. 48 is a diagram illustrating an example of parallel movement conversion that the converting function 153 performs in the first embodiment. FIG. 48 illustrates an example of the case in which a line is subject to the parallel movement conversion.

In the example illustrated in FIG. 48, an icon 10 for specifying the rearward direction or the forward direction in the time direction as the conversion direction is arranged on the data display format.

For example, it is assumed that the operator specifies a data display format of (W,T,D)=(*,$T_G$,$D_G$) as the pre-conversion state and the conversion reference point and specifies the forward direction (−T) in the time direction as the conversion direction, as illustrated on the left side in FIG. 48. In this case, for example, as illustrated on the right side in FIG. 48, the converting function 153 converts the coordinates (*,$T_G$,$D_G$) indicating the pre-conversion state into coordinates (*,$T_G$−T,$D_G$) indicating the post-conversion state.

The above-mentioned space conversion corresponds to conversion of the pre-conversion state indicated by a line extending in the width direction into the post-conversion state indicated by another line extending in the width direction by the parallel movement in the time direction with reference to the conversion reference point indicated by the above-mentioned line.

As a result, for example, as illustrated in FIG. 48, the display control function 152 switches the state before the conversion in which information indicating a medicine, specimen inspection measurement values, and vital measurement values are displayed for one time point to a state after the conversion in which information indicating a medicine, specimen inspection measurement values, and vital measurement values are displayed for another time point.

Figure 49:
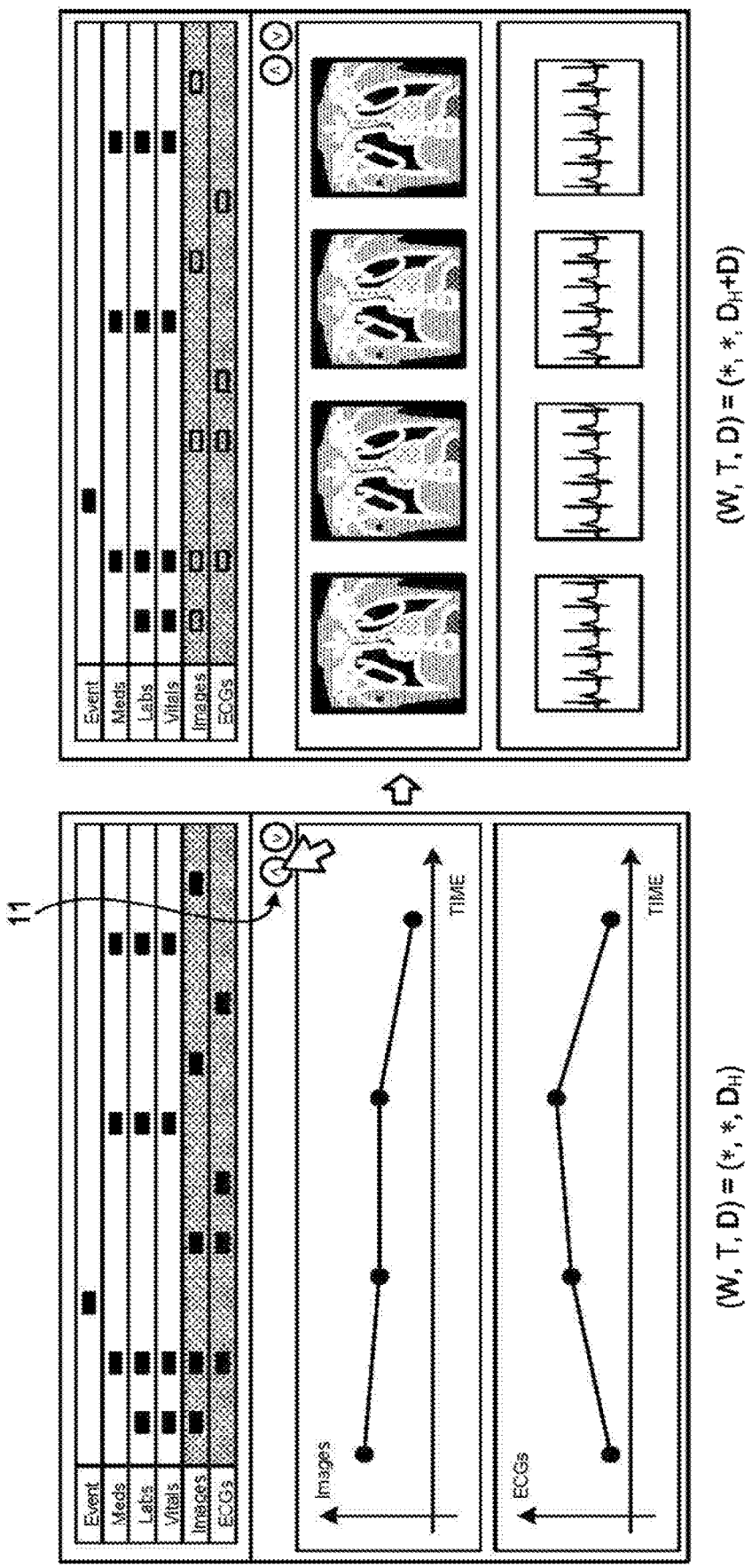
FIG. 49 is a diagram illustrating another example of the parallel movement conversion that the converting function performs in the first embodiment.

FIG. 49 is a diagram illustrating another example of the parallel movement conversion that the converting function 153 performs in the first embodiment. FIG. 49 illustrates an example of the case in which a plane is subject to the parallel movement conversion.

In the example illustrated in FIG. 49, an icon 11 for specifying the forward direction or the rearward direction in the depth direction as the conversion direction is arranged on the data display format.

For example, it is assumed that the operator specifies a data display format of (W,T,D)=(*,*,$D_H$) as the pre-conversion state and the conversion reference point and specifies the rearward direction (+D) in the depth direction as the conversion direction, as illustrated on the left side in FIG. 49. In this case, for example, as illustrated on the right side in FIG. 49, the converting function 153 converts coordinates (*,*,$D_H$) indicating the pre-conversion state into coordinates (*,*,$D_H$+D) indicating the post-conversion state.

The above-mentioned space conversion corresponds to conversion of the pre-conversion state indicated by a plane extending in the width direction and the time direction into the post-conversion state indicated by another plane extending in the width direction and the time direction by the parallel movement in the depth direction with reference to the conversion reference point indicated by the above-mentioned plane.

As a result, for example, as illustrated in FIG. 49, the display control function 152 switches the state before the conversion in which image measurement values and electrocardiogram measurement values are displayed for a plurality of time points to a state after the conversion in which pieces of image data and pieces of electrocardiogram image data are displayed for the time points.

Although some examples have been described above, the space conversion that the converting function 153 performs is not limited to the above-mentioned two-dimensional space conversion. The converting function 153 may perform space conversion of equal to or higher than the three dimensions such as magnification to a space from a plane, rotation and parallel movement of a space, and reduction to a plane from a space.

As mentioned above, in the first embodiment, the space conversion is performed with reference to the conversion reference point specified by the operator in the medical examination data space having the dimension corresponding to the data display format determined for each piece of medical examination data to thereby switch display of the medical examination data.

Among the conventional techniques, there is a technique in which pieces of information classified into two types of attributes (date, data item) are displayed in a table format and they are displayed in three display formats in accordance with three selection manners as a method for grasping the pieces of information multilaterally.

In general, when pieces of information are grasped multilaterally, the viewpoint is switched using information being currently displayed as a starting point. For example, when there is a concerning inspection result in checking of inspection results in a broad view, the viewpoint is switched to check details of the inspection result, check temporal shift of the inspection result, and so on. When there is a concerning inspection result in checking of the details of the inspection result, the viewpoint is switched to compare the concerning inspection result with treatment contents (medication or the like) just before, compare it with inspection results for other patients, and so on.

The above-mentioned conventional technique, however, does not take the information being currently displayed and information being focused into consideration in the switching of the display format, resulting in lack of relevancy of display contents and information of a focus point before and after the switching. As a result, the switching is not meaningful for the operator intuitively and clinically and prevents the operator from grasping a patient state, treatment contents, and the like in some cases. Moreover, in the above-mentioned conventional technique, the display in the table format is limited to the two types of attributes and this can limit the viewpoints of analysis. For example, when pieces of data with different degrees of verbosity are compared, the same data is compared between different patients, and so on, switching involving them cannot be performed by the table format and the selection manners thereof.

Unlike the conventional technique, the first embodiment enables the pieces of medical examination data to be multilaterally browsed using information being currently displayed as a starting point by switching the display of the medical examination data with the space conversion with reference to the specified conversion reference point. Accordingly, the embodiment can present the pieces of medical examination data in the appropriate display formats in accordance with the clinical examination objects.

Second Embodiment

Although in the above-mentioned embodiment, the converting function 153 performs the space conversion on the basis of the pre-conversion state, the conversion reference point, and the conversion direction specified by the operator, as an example, the embodiment is not limited thereto.

The converting function 153 may perform the space conversion on the basis of, for example, a specified conversion amount in addition thereto. Hereinafter, this example will be described as a second embodiment. In the second embodiment, different points from the above-mentioned embodiment are mainly described and description of overlapped contents with the above-mentioned embodiment is omitted.

In the embodiment, the display control function 152 provides a reception unit for receiving, from an operator, an operation of specifying the conversion amount of the space conversion through a display screen.

Figure 50:
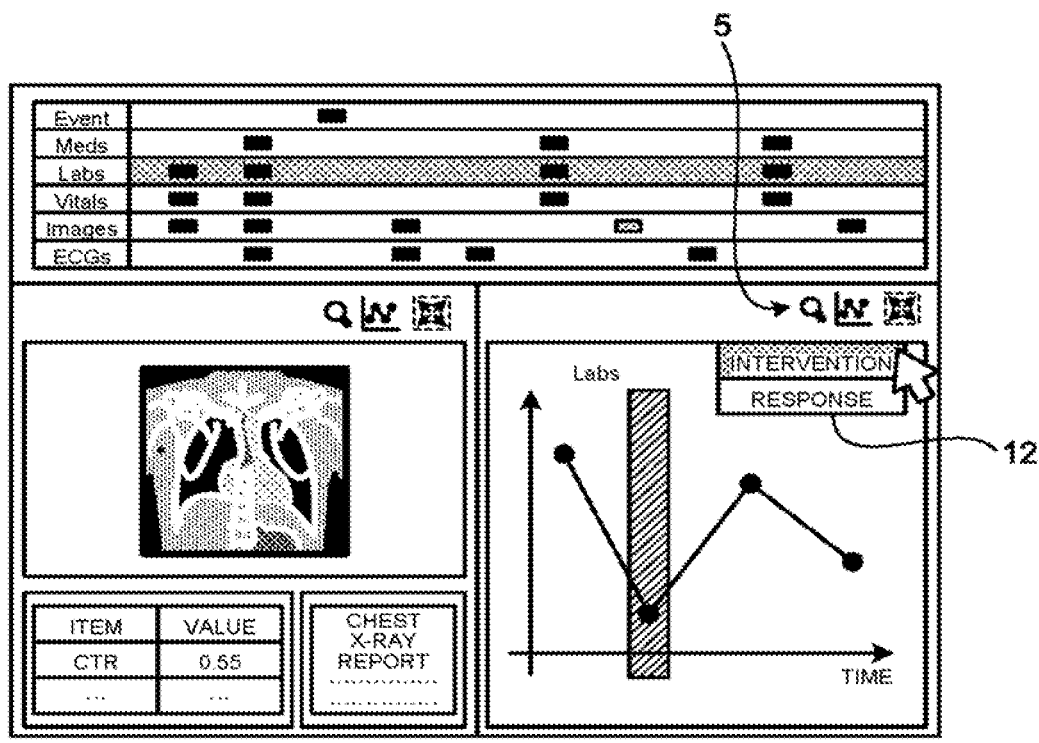
FIG. 50 is a diagram illustrating an example of a reception unit that a display control function provides according to a second embodiment.

FIG. 50 is a diagram illustrating an example of the reception unit that the display control function 152 provides in the second embodiment.

For example, as illustrated in FIG. 50, when an operation on an icon for specifying the conversion direction is performed, the display control function 152 displays an operation reception unit for specifying the conversion amount on the display screen. The display control function 152 displays, for example, a pull-down menu 12 listing classifications of the medical examination data as the operation reception unit for specifying the conversion amount.

FIG. 51 is a diagram illustrating an example of the pull-down menu 12 that the display control function 152 displays in the second embodiment.

As illustrated in FIG. 51, for example, pieces of information indicating classifications of "intervention" and "response" are listed on the pull-down menu 12 that the display control function 152 displays.

In this case, the storage 120 stores therein, for example, a granularity mapping table defining the conversion amounts for the respective classifications of the pieces of medical examination data as one integrated medical examination $D_B$.

FIG. 52 is a diagram illustrating an example of the granularity mapping table in the second embodiment.

As illustrated in FIG. 52, the granularity mapping table stores therein, for example, pieces of information while a mapping ID, a name, and a table are made to correspond to one another. Identification information for uniquely identifying the classification of the medical examination data is set to the mapping ID. The name of the classification is set to the name. Information indicating tables of the pieces of medical examination data as display targets, as information indicating the conversion amount in the direction corresponding to the classification is set to the table.

In the embodiment, the converting function 153 performs the space conversion on the basis of the pre-conversion state, the conversion reference point, the conversion direction, and the conversion amount specified by the operator. To be specific, the converting function 153 acquires coordinates and dimension of the post-conversion state on the basis of the acquired pre-conversion state, conversion reference point, and conversion direction, the information of the display coordinate master, and the information of the granularity mapping table.

Figure 53:
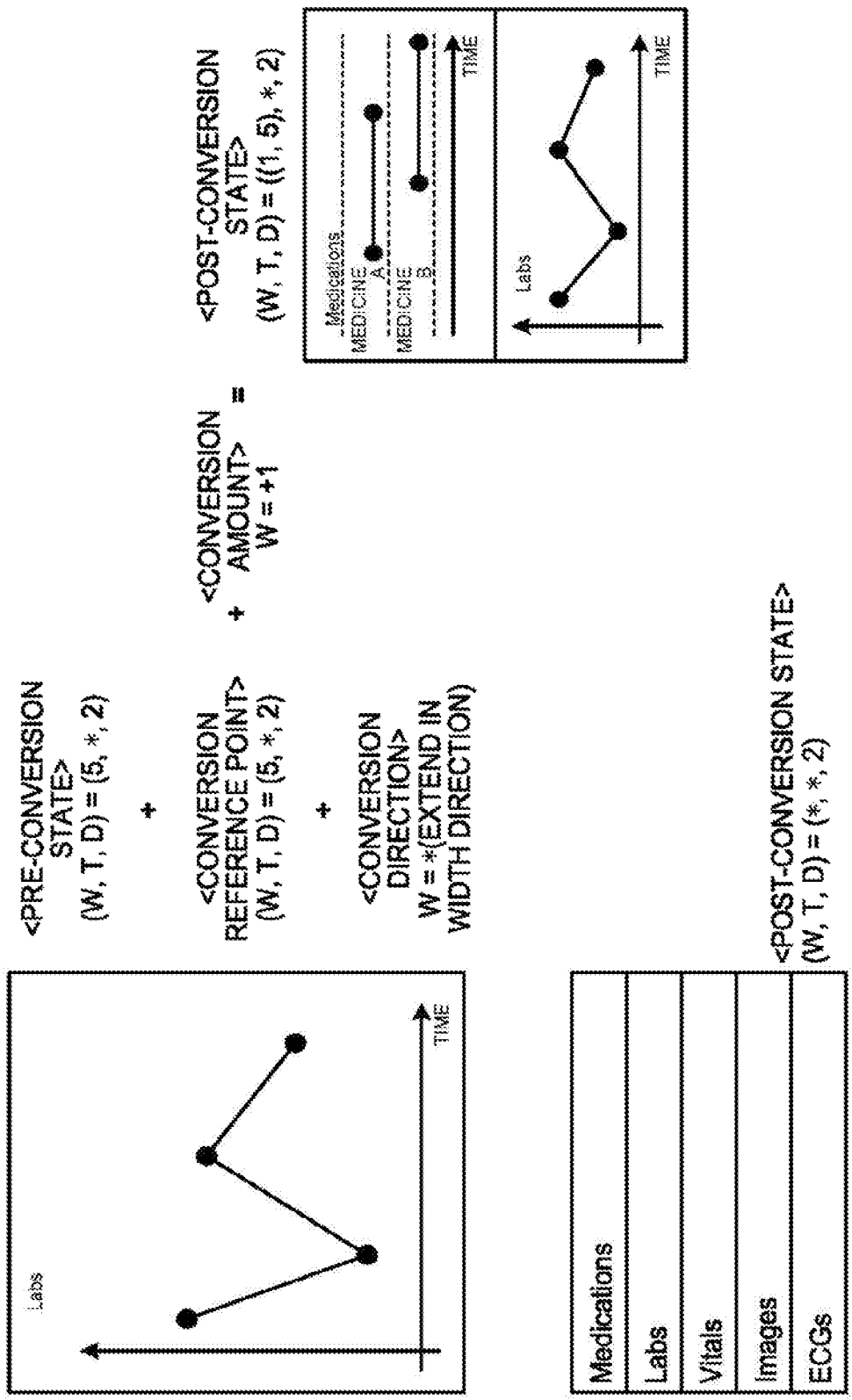
FIG. 53 is a diagram illustrating an example of calculation of coordinates indicating a post-conversion state by a converting function in the second embodiment.

FIG. 53 is a diagram illustrating an example of calculation of the coordinates indicating the post-conversion state by the converting function 153 in the second embodiment.

For example, when the coordinates indicating the pre-conversion state are (W,T,D)=(5,*,2), the coordinates indicating the conversion reference point are (W,T,D)=(5,*,2), the coordinate indicating the conversion direction is W=*, and the conversion amount is W=+1 as illustrated on the upper left side to the right side in FIG. 53, the converting function 153 calculates (W,T,D)=((1,5),*,2) as the coordinates indicating the post-conversion state. What the conversion amount is W=+1 indicates that in addition to a data display format of (W,T,D)=(5,*,2), a data display format of (W,T,D)=(1,*,2) is further displayed.

In this case, the converting function 153 acquires the medical examination data as the display target by referring to the table information stored in the granularity mapping table on the basis of the classification specified from the classifications displayed on the pull-down menu 12 and the specified conversion direction. Furthermore, the converting function 153 compares the acquired medical examination data and the medical examination data contained in the pre-conversion state to specify a data display format to be added or deleted as the display target.

As a result, for example, as illustrated on the upper left side to the right side FIG. 53, the display control function 152 switches the state before the conversion in which pieces of specimen inspection summary data are displayed for a plurality of time points as the pieces of medical examination data related to the specimen inspection to a state after the conversion in which pieces of medication summary data are displayed for the time points as the pieces of medical examination data related to the medication in addition to the pieces of specimen inspection summary data.

As described in the above-mentioned first embodiment, for example, when no conversion amount is used, the converting function 153 calculates (W,T,D)=(*,*,2) as the coordinates indicating the post-conversion state. In this case, as a result of increase in the number of data display formats that are displayed on the display screen, the amount of the pieces of medical examination data that are displayed is increased and information on the display screen can be difficult to be observed in some cases (see a lower left portion in FIG. 53). On the other hand, in the second embodiment, the number of pieces of medical examination data that are displayed on the display screen can be adjusted by performing the space conversion using the conversion amount, thereby making the information on the display screen easy to be observed.

Although in the above-mentioned example, the granularity mapping table is used as an example, the embodiment is not limited thereto. For example, the display coordinate master table of the display coordinate master may contain information indicating the conversion amount.

Figure 55:
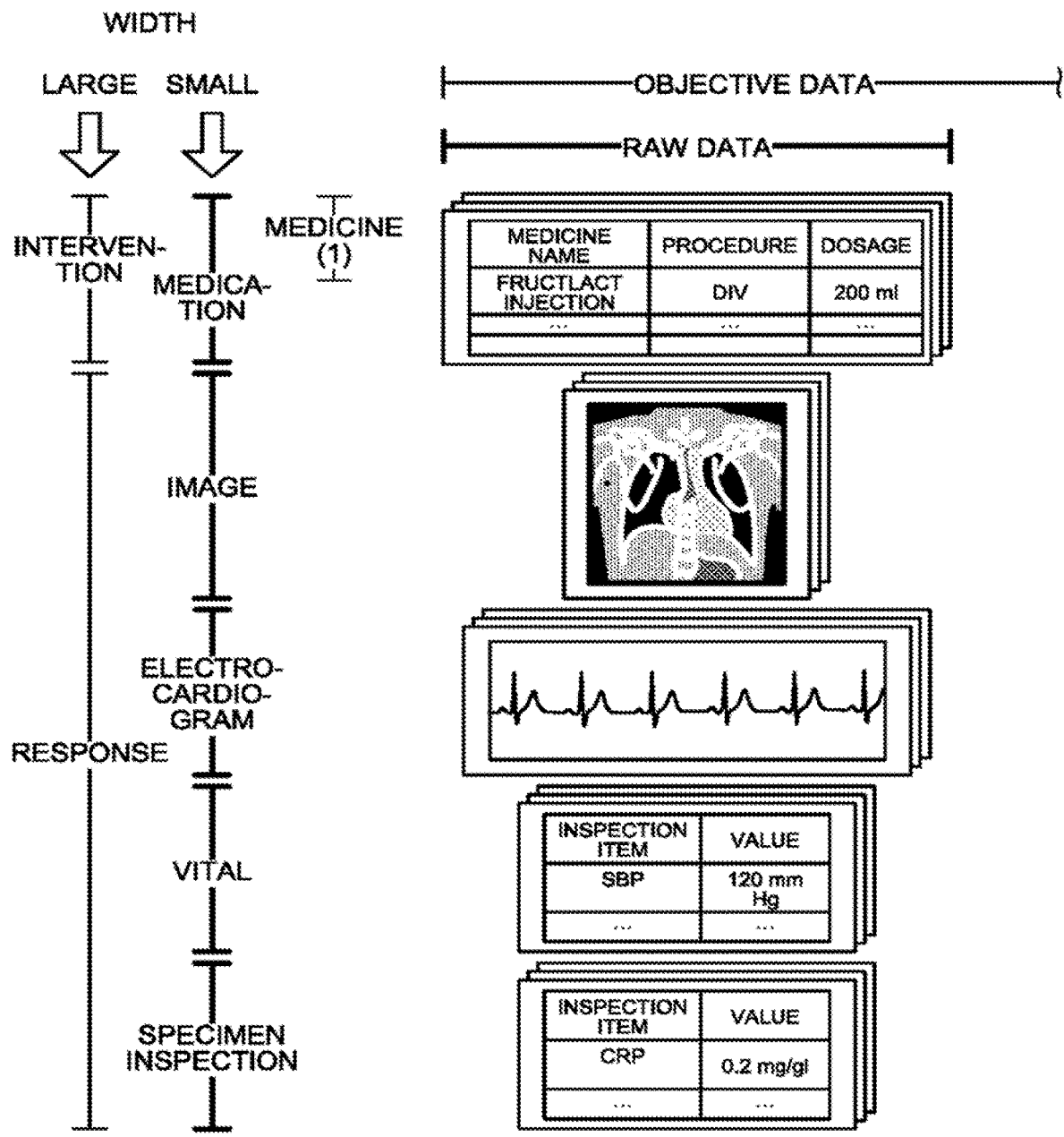
FIG. 55 is a diagram illustrating units of coordinate values in a width direction that are set to the display coordinate master table in the second embodiment.

FIG. 54 is a diagram illustrating an example of the display coordinate master table in the second embodiment. FIG. 55 is a diagram illustrating an example of units of coordinate values in the width direction that are set to the display coordinate master table in the second embodiment.

For example, as illustrated in FIG. 54, for the coordinate values in the width direction, two coordinate values of a large Width and a small Width are stored as pieces of information indicating different conversion amounts instead of Width illustrated in FIG. 20.

As illustrated in FIG. 55, for example, a coordinate value is set to the large Width by a unit of data related to the intervention or data related to the response. Furthermore, a coordinate value is set to the small Width by a unit of data related to the medication, data related to the image, data related to the electrocardiogram, data related to the vital, or data related to the specimen inspection. The coordinate values that are set to the large Width are set so as to cause more data display IDs to correspond to one coordinate value in comparison with those of the coordinate values that are set to those of the small Width.

In this case, the display control function 152 displays the pull-down menu 12 containing information indicating "large" and information indicating "small". The converting function 153 performs the space conversion on the basis of the coordinate value set to the large Width in the display coordinate master table when the operator specifies "large". The converting function 153 performs the space conversion on the basis of the coordinate value set to the small Width in the display coordinate master table when the operator specifies "small".

As a result, when the operator specifies "large", the display control function 152 displays more pieces of medical examination data on the display screen in comparison with those when the operator specifies "small".

Hereinafter, the space conversion that the converting function 153 performs in the second embodiment will be described using specific examples.

Figure 56:
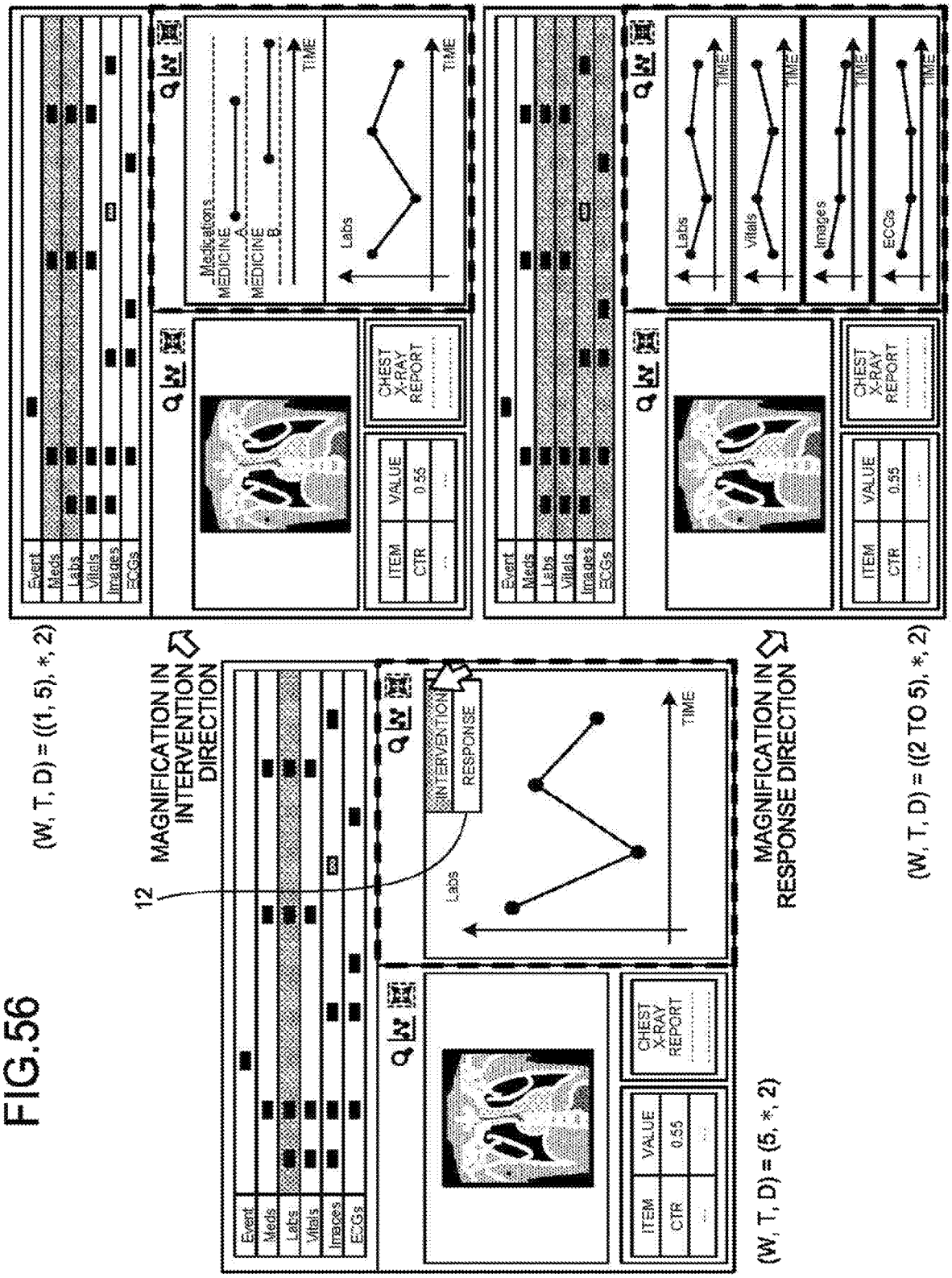
FIG. 56 is a diagram illustrating an example of magnification or reduction conversion that the converting function performs in the second embodiment.

FIG. 56 is a diagram illustrating an example of magnification or reduction conversion that the converting function 153 performs in the second embodiment. FIG. 56 illustrates an example of the case in which a magnification or reduction range in the width direction is specified.

In the example illustrated in FIG. 56, the pull-down menu 12 for specifying the classification of the medical examination data is displayed on a data display format as the operation reception unit for specifying the conversion amount. As illustrated in FIG. 56, for example, pieces of information indicating classifications of "intervention" and "response" are listed on the pull-down menu 12 that the display control function 152 displays.

For example, it is assumed that the operator specifies a data display format of (W,T D)=(5,*,2) as the pre-conversion state and the conversion reference point and specifies the width direction (W=*) as the conversion direction, as illustrated on the left side in FIG. 56.

When the operator further specifies "intervention" as the conversion amount, for example, as illustrated on the upper right side in FIG. 56, the converting function 153 converts coordinates (5,*,2) indicating the pre-conversion state into coordinates ((1,5),*,2) indicating the post-conversion state.

The above-mentioned space conversion corresponds to conversion of the pre-conversion state indicated by a line extending in the time direction into the post-conversion state indicated by a plane extending in the width direction and the time direction by the magnification in the width direction in a range of the intervention with reference to the conversion reference point indicated by the above-mentioned line.

As a result, for example, as illustrated on the left side to the upper right side in FIG. 56, the display control function 152 switches the state before the conversion in which pieces of specimen inspection summary data are displayed for a plurality of time points to a state after the conversion in which pieces of medication summary data and the pieces of specimen inspection summary data are displayed for the time points.

On the other hand, when the operator specifies "response" as the conversion amount, for example, as illustrated on the lower right side in FIG. 56, the converting function 153 converts coordinates (5,*,2) indicating the pre-conversion state into coordinates ((2 to 5),*,2) indicating the post-conversion state.

The above-mentioned space conversion corresponds to conversion of the pre-conversion state indicated by the line extending in the time direction into the post-conversion state indicated by a plane extending in the width direction and the time direction by the magnification in the width direction in a range of the response with reference to the conversion reference point indicated by the above-mentioned line.

As a result, for example, as illustrated on the left side to the lower right side in FIG. 56, the display control function 152 switches the state before the conversion in which the pieces of specimen inspection summary data are displayed for the time points to a state after the conversion in which the pieces of specimen inspection summary data, pieces of vital summary data, image measurement values, and electrocardiogram measurement values are displayed for the time points.

FIG. 57 is a diagram illustrating another example of the magnification or reduction conversion that the converting function 153 performs in the second embodiment. FIG. 57 illustrates an example of the case in which a magnification or reduction range in the time direction is specified.

In the example illustrated in FIG. 57, a pull-down menu 13 for specifying a range in the time direction is displayed on a data display format as the operation reception unit for specifying the conversion amount. For example, "to selection range", "before and after event", and "all time ranges" are listed on the pull-down menu 13.

For example, it is assumed that the operator specifies a data display format of (W,T,D)=(2,1,1) as the pre-conversion state and the conversion reference point and specifies the time direction (T=*) as the conversion direction, as illustrated on the left side in FIG. 57.

When the operator further specifies "to selection range" as the conversion amount, for example, as illustrated on the upper right side in FIG. 57, the converting function 153 converts coordinates (2,1,1) indicating the pre-conversion state into coordinates (2,(1,2),1) indicating the post-conversion state.

The above-mentioned space conversion corresponds to conversion of the pre-conversion state indicated by a point into the post-conversion state indicated by a line extending in the time direction by the magnification in the time direction to the selection range with reference to the conversion reference point indicated by the above-mentioned point.

As a result, for example, as illustrated on the left side to the upper right side in FIG. 57, the display control function 152 switches the state before the conversion in which image data is displayed for one time point to a state after the conversion in which pieces of image data are displayed for a plurality of time points from the one time point to the selection range.

On the other hand, when the operator specifies "before and after event" as the movement amount, for example, as illustrated on the lower right side in FIG. 57, the converting function 153 converts coordinates (2,1,1) indicating the pre-conversion state into coordinates (2,(1 to 3),1) indicating the post-conversion state.

The above-mentioned space conversion corresponds to conversion of the pre-conversion state indicated by the point into the post-conversion state indicated by a line extending in the time direction by the magnification in the time direction to after the event with reference to the conversion reference point indicated by the above-mentioned point.

As a result, for example, as illustrated on the left side to the lower right side in FIG. 57, the display control function 152 switches the state before the conversion in which the image data is displayed for one time point to a state after the conversion in which pieces of image data are displayed for a plurality of time points from the one time point to after the event.

FIG. 58 is a diagram illustrating an example of parallel movement conversion that the converting function 153 performs in the second embodiment. FIG. 58 illustrates an example of the case in which a movement amount in the time direction is specified.

In the example illustrated in FIG. 58, a pull-down menu 14 for specifying the movement amount in the time direction is displayed on a data display format as the operation reception unit for specifying the conversion amount. In the example illustrated in FIG. 58, for example, "previous time", "one month before", "one year before", and "before event" are listed on the pull-down menu 14.

For example, with the converting function 153, it is assumed that the operator specifies a data display format of (W,T,D)=(2,2,*) as the pre-conversion state and the conversion reference point and specifies the time direction (T=*) as the conversion direction, as illustrated on the left side in FIG. 58.

In this case, when the operator further specifies "previous time" as the movement amount, for example, as illustrated on the upper right side in FIG. 58, the converting function 153 converts coordinates (2,2,*) indicating the pre-conversion state into coordinates (2,1,*) indicating the post-conversion state.

The above-mentioned space conversion corresponds to conversion of the pre-conversion state indicated by a line extending in the depth direction into the post-conversion state indicated by another line extending in the depth direction by the movement in the time direction to the previous time with reference to the conversion reference point indicated by the above-mentioned line.

As a result, for example, as illustrated on the left side to the upper right side in FIG. 58, the display control function 152 switches the state before the conversion in which image data, an image measurement value, and an image reading report are displayed for one time point to a state after the conversion in which image data, an image measurement value, and an image reading report are displayed for a previous time point of the one time point.

On the other hand, when the operator specifies "before event" as the movement amount, for example, as illustrated on the lower right side in FIG. 58, the converting function 153 converts coordinates (2,2,*) indicating the pre-conversion state into coordinates (2,5,*) indicating the post-conversion state.

The above-mentioned space conversion corresponds to conversion of the pre-conversion state indicated by a line extending in the depth direction into the post-conversion state indicated by another line extending in the depth direction by the movement in the time direction to before a predetermined event with reference to the conversion reference point indicated by the above-mentioned line.

As a result, for example, as illustrated on the left side to the lower right side in FIG. 58, the display control function 152 switches the state before the conversion in which the image data, the image measurement value, and the image reading report are displayed for one time point to a state after the conversion in which image data, an image measurement value, and an image reading report are displayed for a different time point before the event from the one time point.

As mentioned above, in the second embodiment, the space conversion is performed on the basis of the specified conversion amount in addition to the pre-conversion state, the conversion reference point, and the conversion direction. Accordingly, with the second embodiment, a display range after the conversion that cannot be specified only by the conversion direction and the like can be desirably specified by acquiring the conversion amount of the space conversion.

For example, in the magnification conversion in the width direction, the display amount of the pieces of medical examination data is increased when the data type is increased and visibility of the pieces of medical examination data can thereby be lowered. Unlike this case, in the second embodiment, limitation to an appropriate magnification range (limitation of the data type that is displayed) can be set by specifying the conversion amount, thereby improving the visibility of the pieces of medical examination data. In the parallel movement conversion in the time direction, conversion into the medical examination data at a desired time point can be easily performed by specifying the movement amount.

Third Embodiment

In the above-mentioned embodiments, the data display formats are made to correspond to the width direction, the time direction, and the depth direction in the medical examination data space, as an example. The embodiment is, however, not limited thereto.

The medical examination data space may further have, for example, a dimension corresponding to a patient. Hereinafter, this example will be described as a third embodiment. In the third embodiment, different points from the above-mentioned embodiments are mainly described and description of overlapped contents with the above-mentioned embodiments is omitted.

In the embodiment, the display control function 152 provides a reception unit for receiving, from an operator, an operation of specifying a position in a patient direction through a display screen.

Figure 59:
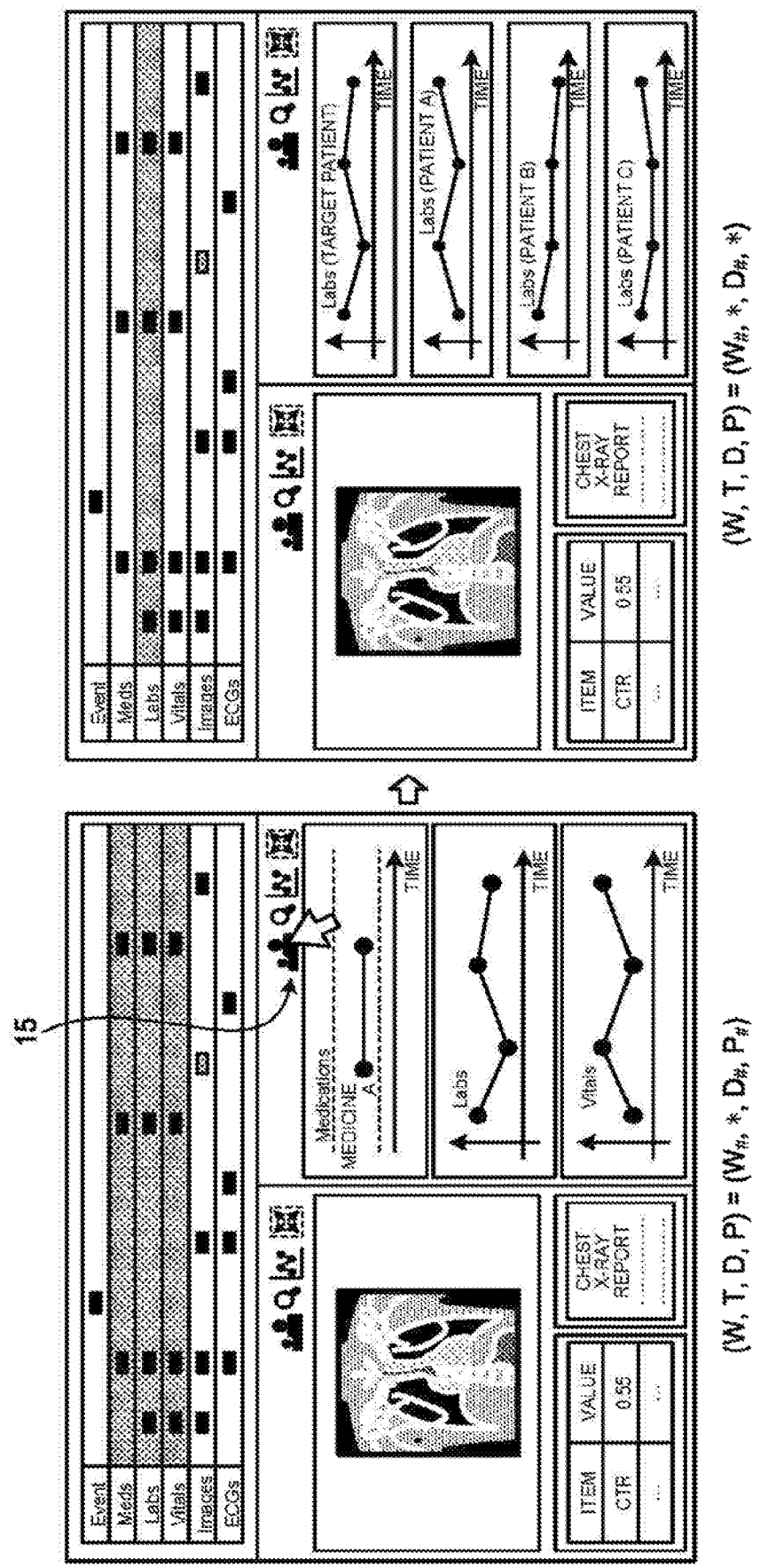
FIG. 59 is a diagram illustrating an example of a reception unit that a display control function provides according to a third embodiment.

FIG. 59 is a diagram illustrating an example of the reception unit that the display control function 152 provides in the third embodiment.

As illustrated in FIG. 59, the display control function 152 arranges, on a data display format, an icon 15 for specifying conversion in the patient direction in addition to the three icons for specifying the conversion direction.

In the embodiment, when the operator specifies the conversion in the patient direction, the converting function 153 displays pieces of medical examination data of other patients in the same data display format as that of pieces of medical examination data of a target patient that has been displayed in specification of the pre-conversion state. For example, coordinates in the medical examination data space that further has the patient (P) direction are expressed as (W,T,D,P).

As illustrated in FIG. 59, for example, when the operator specifies a data display format of $(W,T,D,P)=(W_\#,*,D_\#,P_\#)$ as the pre-conversion state and the conversion reference point and specifies the patient direction (P=*) as the conversion direction, the converting function 153 converts coordinates $(W_\#,*,D_\#,P_\#)$ indicating the pre-conversion state into coordinates $(W_\#,*,D_\#,*)$ indicating the post-conversion state.

The above-mentioned space conversion corresponds to conversion of the pre-conversion state indicated by a line extending in the time direction into the post-conversion state indicated by a plane extending in the time direction and the patient direction by reduction in the patient direction with reference to the conversion reference point indicated by the above-mentioned line.

As a result, for example, as illustrated in FIG. 59, the display control function 152 switches the state before the conversion in which medication summary data, specimen inspection summary data, and vital summary data are displayed as the pieces of medical examination data related to the medication, the specimen inspection, and the vitals for the target patient to a state after the conversion in which specimen inspection summary data is displayed as the medical examination data related to the specimen inspection for each of the target patient, a patient A, a patient B, and a patient C.

Although the pieces of medical examination data of other patients are displayed for the respective patients herein as an example, the embodiment is not limited thereto. The pieces of medical examination data of other patients may be displayed, for example, in one data display format provided by summarizing them with an average value or the like.

The patients as display targets may be narrowed by a disease, a medical examination phase, or the like or may be limited to patients specified by the operator or the system. The operator may be capable of specifying the patients as the display targets by specifying the conversion amount of the space conversion as in the second embodiment.

As mentioned above, the medical examination data space further has the dimension corresponding to the patient in the third embodiment. Accordingly, the third embodiment enables switching of data display formed by the dimensions containing the patient axis. Pieces of medical examination data can thereby be compared among the patients in a desired data display format.

Fourth Embodiment

In the above-mentioned embodiments, correspondence between the medical examination data space and various pieces of medical examination data is fixed as an example. The embodiments are not however limited thereto.

For example, the converting function 153 may dynamically change the medical examination data and the medical examination data space in accordance with a disease, an operator, or a medical examination phase. The operator referred herein is a physician, a radiologist, a nurse, or the like. The medical examination phase is an outpatient phase, a diagnosis phase, a preoperative phase, a postoperative phase, or the like.

The display control function 152 and the converting function 153, for example, change the types of the pieces of medical examination data that are made to correspond to the medical examination data space in accordance with the disease, the operator, or the medical examination phase. Alternatively, the display control function 152 and the converting function 153, for example, change coordinates that are made to correspond to the respective data display formats in the medical examination data space in accordance with the disease, the operator, or the medical examination phase.

In this case, for example, the storage 120 holds, in the integrated medical examination DB, tables storing therein the necessary types of the pieces of medical examination data and stores the data display formats of the respective pieces of medical examination data in the data display format master. Furthermore, the storage 120 stores therein a combination of the data display format master and the display coordinate master for each disease, operator, or medical examination phase. The display control function 152 and the converting function 153, for example, receive specification of the disease, profession of the operator, or the medical examination phase from the operator and switches the data display format master and the display coordinate master that are used for each processing in accordance with the received content.

When the disease is cardiac failure, for example, the display control function 152 and the converting function 153 switch the data display format master and the display coordinate master so as to use meal data as the medical examination data. When the disease is cancer, they switch the data display format master and the display coordinate master so as to use a pathological image as the medical examination data.

When the profession of the operator is the radiologist, for example, the display control function 152 and the converting function 153 switch the data display format master and the display coordinate master so as to use screen data of a clinical application instead of the image reading report of the image as the medical examination data. When the profession of the operator is an internist, for example, the display control function 152 and the converting function 153 switch the data display format master and the display coordinate master so as to use pieces of data related to intervention and response as the pieces of medical examination data. When the profession of the operator is the radiologist, for example, the display control function 152 and the converting function 153 switch the data display format master and the display coordinate master so as to use pieces of data acquired from the HIS 300, the RIS 400, and the PACS 500 as the pieces of medical examination data.

When the medical examination phase is the outpatient phase, for example, the display control function 152 and the converting function 153 switch the data display format master and the display coordinate master so as to contain no vital and no nursing record as the medical examination data.

As mentioned above, in the fourth embodiment, the pieces of medical examination data and the medical examination data space are dynamically changed in accordance with the disease, the operator, or the medical examination phase. Accordingly, the fourth embodiment can switch display of the medical examination data more appropriately in accordance with the clinical examination object.

Fifth Embodiment

In the above-mentioned first embodiment, the display control function 152 displays the icons indicating presence and absence of the pieces of medical examination data in the display format in which the transverse axis is the times series and the longitudinal axis is the data type (for example, see the guide information 8 illustrated in FIG. 31) as the guide information indicating the position in the medical examination data space that corresponds to the data display format being displayed, as an example. The guide information is however not limited thereto.

Hereinafter, another example related to the guide information will be described as a fifth embodiment. In the fifth embodiment, different points from the above-mentioned embodiments are mainly described and description of overlapped contents with the above-mentioned embodiments is omitted.

In the embodiment, the display control function 152 displays, as the guide information, a graphic indicating dimensions of the medical examination data space stereoscopically, and displays, on the graphic, information indicating a position that corresponds to a data display format being displayed.

Figure 60:
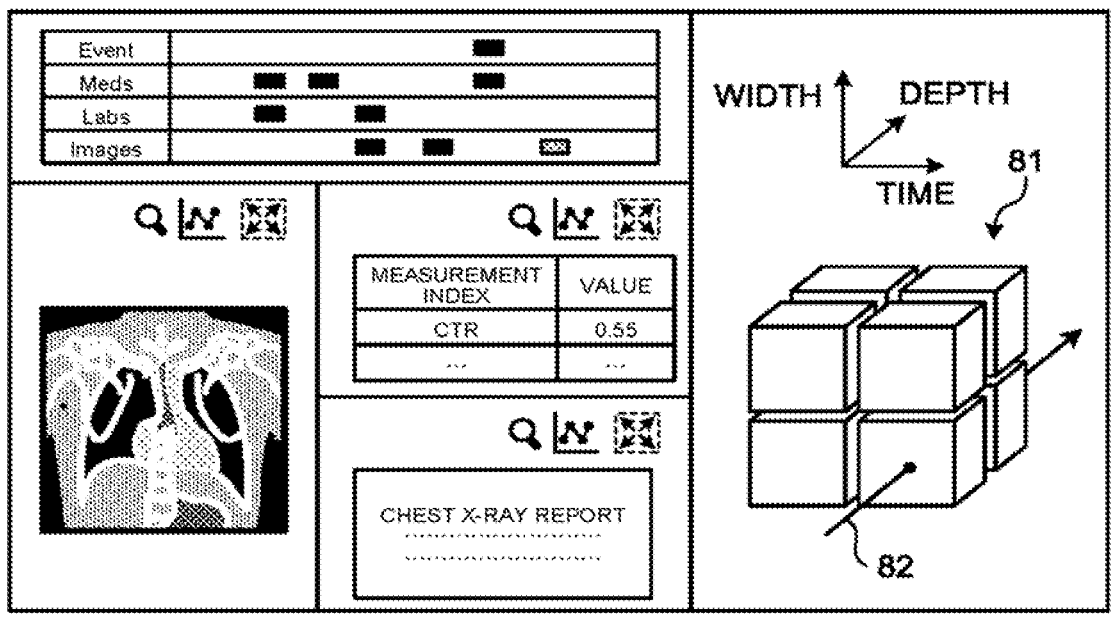
FIG. 60 is a diagram illustrating an example of guide information that a display control function displays according to a fifth embodiment.
Figure 61:
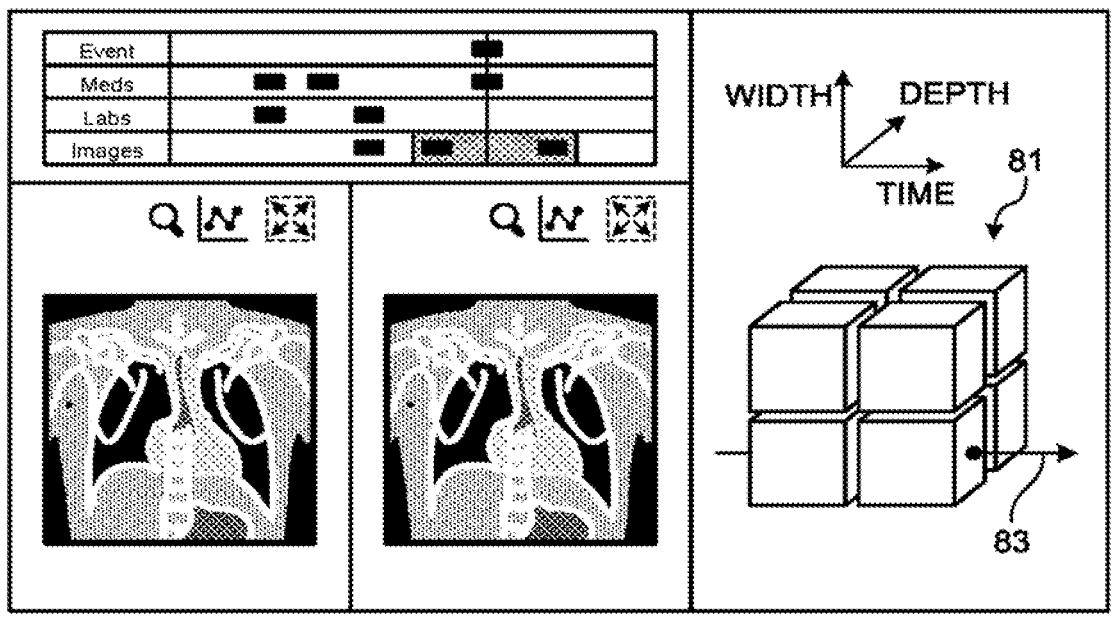
FIG. 61 is a diagram illustrating another example of the guide information that the display control function displays in the fifth embodiment.
Figure 62:
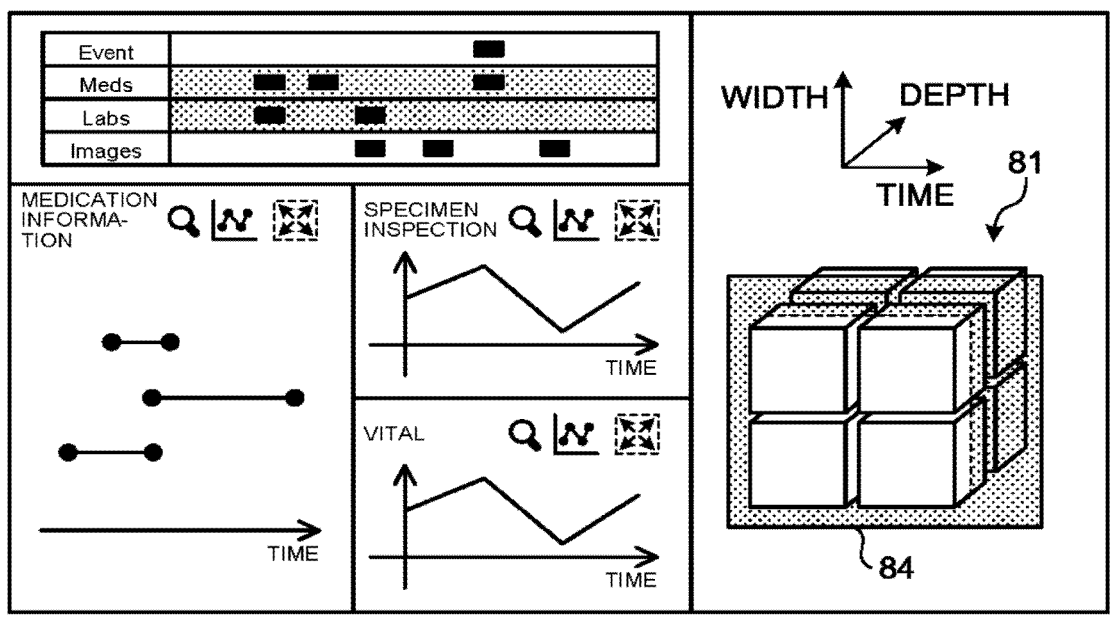
FIG. 62 is a diagram illustrating still another example of the guide information that the display control function displays in the fifth embodiment.

FIGS. 60 to 62 are diagrams illustrating examples of the guide information that the display control function 152 displays in the fifth embodiment.

As illustrated in FIGS. 60 to 62, the display control function 152 displays, for example, a cubic graphic 81 having sides along the width direction, the depth direction, and the time direction on a display screen. The display control function 152 may display the graphic 81 all the time while a display screen is displayed on the display 140 or may avoid displaying the graphic 81 in initial display and display it when requested from an operator. The display control function 152 may display the graphic 81 on a sub screen different from the display screen displaying the pieces of medical examination data as in a picture-in-picture (PIP) way.

The display control function 152 displays, on the cubic graphic 81, the information indicating the position that corresponds to the data display format being displayed.

As in the examples illustrated in FIGS. 27 and 33, FIG. 60 illustrates an example in which the display control function 152 displays the data display formats indicated by a line of (W,T,D)=(2,1,*) in the medical examination data space. In this case, as illustrated in FIG. 60, the display control function 152 displays, for example, a linear graphic 82 passing through positions of (W,T)=(2,1) and extending in the depth direction on the cubic graphic 81.

As in the example illustrated in FIG. 34, FIG. 61 illustrates an example in which the display control function 152 displays the data display formats indicated by a line of (W,T,D)=(2,*,1) in the medical examination data space. In this case, as illustrated in FIG. 61, the display control function 152 displays, for example, a linear graphic 83 passing through positions of (W,D)=(2,1) and extending in the time direction on the cubic graphic 81.

As in the example illustrated in FIG. 36, FIG. 62 illustrates an example in which the display control function 152 displays the data display formats indicated by a plane of (W,T,D)=(*,*,2) in the medical examination data space. In this case, as illustrated in FIG. 62, the display control function 152 displays, for example, a planar graphic 84 passing through positions of D=2 and extending in the width direction and the time direction on the cubic graphic 81.

For example, when the display control function 152 displays the data display formats indicated by points such as (W,T,D)=(2,1,1), (2,1,2), and (2,1,3) in the medical examination data space as in the examples illustrated in FIGS. 24 to 27, it displays dotted graphics at positions corresponding to the respective points on the cubic graphic 81.

For example, when the display control function 152 simultaneously displays the data display formats indicated by a plurality of points, lines, or planes in the medical examination data space, it simultaneously displays dotted, linear, or planar graphics corresponding to the respective formats on the cubic graphic 81.

For example, when the display control function 152 simultaneously displays the data display formats indicated by a line of (W,T,D)=(2,1,*) in the medical examination data space and the data display formats indicated by a plane of (W,T,D)=(*,*,2) in the medical examination data space as in the example illustrated in FIG. 37, it displays, on the cubic graphic 81, each of a linear graphic passing through positions of (W,T)=(2,1) and extending in the depth direction and a planar graphic passing through positions of D=2 and extending in the width direction and the time direction.

As illustrated in FIGS. 60 to 62, the display control function 152 displays the graphic 81 having a shape that a plurality of cubes are aligned in three-axis directions, as an example. In this case, for example, the display control function 152 may change display modes of the cubes in accordance with classification of the data display formats being displayed. As an example for the width direction, the display control function 152 displays a cube corresponding to the data display format related to intervention and a cube corresponding to the data display format related to response in different colors.

Thus, in the embodiment, the display control function 152 displays, as the guide information, the graphic indicating the dimensions of the medical examination data space stereoscopically, and displays, on the graphic, the pieces of information indicating the positions that correspond to the data display formats being displayed. An operator can thereby grasp the positions of the data display formats being displayed in the medical examination data space more intuitively.

In the embodiment, for example, the display control function 152 may further receive, from the operator, an instruction to switch display of the medical examination data on the above-mentioned graphic 81 indicating the dimensions of the medical examination data space stereoscopically.

The display control function 152 receives, from the operator, an operation of rotating, moving in parallel, magnifying, or reducing the dotted graphic, linear graphic, or planar graphic displayed on the graphic 81 indicating the dimensions of the medical examination data space, for example.

To be specific, the display control function 152 receives, from the operator, specification of a pre-conversion state, a conversion reference point, and a conversion direction by receiving an operation on the dotted graphic, linear graphic, or planar graphic displayed on the graphic 81 indicating the dimensions of the medical examination data space.

The display control function 152 receives specification of the pre-conversion state from the operator by, for example, receiving an operation of selecting a desired graphic displayed on the graphic 81 indicating the dimensions of the medical examination data space. The display control function 152 receives specification of the conversion reference point from the operator by receiving an operation of selecting a point, line, or plane on the selected graphic. The display control function 152 receives specification of the conversion direction from the operator by receiving an operation of rotating, moving in parallel, magnifying, or reducing a desired graphic displayed on the graphic 81 indicating the dimensions of the medical examination data space.

The magnification operation is an operation of switching the dotted graphic to the linear graphic or planar graphic, or an operation of switching the linear graphic to the planar graphic. The reduction operation is an operation of switching the planar graphic to the dotted graphic or linear graphic, or an operation of switching the linear graphic to the dotted graphic.

In the embodiment, the converting function 153 performs rotation conversion, parallel movement conversion, magnification conversion, or reduction conversion as in the first embodiment on the basis of the pre-conversion state, conversion reference point, and conversion direction received by the display control function 152, thereby switching the display of the medical examination data.

Thus, in the embodiment, the display control function 152 receives, from the operator, the instruction to switch the display of the medical examination data on the graphic 81 indicating the dimensions of the medical examination data space stereoscopically. The operator can thereby perform the switching of the display of the medical examination data more intuitively.

In the above-mentioned embodiments, the medical examination data space has the three dimensions as an example. The embodiments are not, however, limited thereto. The number of dimensions of the medical examination data space may be lower than three or may be equal to or higher than four.

In the above-mentioned embodiments, the above-mentioned respective processing functions are implemented by the single processing circuitry 150. The embodiments are not, however, limited thereto. For example, the processing circuitry 150 may be configured by combining a plurality of independent processors and the respective processors may execute the respective programs to implement the respective processing functions. The respective processing functions that the processing circuitry 150 has may be appropriately dispersed or integrated to a single or a plurality of processing circuits for implementation.

A terminology "processor" used in the above description is, for example, a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The processor reads and executes the programs stored in the storage 120 to implement the functions. It should be noted that instead of storage of the programs in the storage 120, the programs may be directly incorporated in a circuit of the processor. In this case, the processor reads and executes the programs incorporated in the circuit to implement the functions. Each processor in the embodiments is not limited to the configuration of a single circuit and a plurality of independent circuits may be combined to configure one processor and implement the functions thereof.

The programs that the processor executes are embedded and provided in a read only memory (ROM), the storage, or the like. The programs may be recorded and provided in a computer-readable recording medium such as a compact disc (CD)-ROM, a flexible disk (FD), a CD-recordable (R), and a digital versatile disc (DVD), as an installable or executable file in these devices. The programs may be stored in a computer connected to a network such as the Internet and provided or distributed by being downloaded via the network. For example, the programs are configured by modules including the above-mentioned functional units. As actual hardware, the CPU reads and executes the programs from the storage medium such as the ROM, so that the modules are loaded on a main storage device and generated on the main storage device.

At least one of the above-mentioned embodiments can have a function for presenting the pieces of medical examination data in the appropriate display formats in accordance with the clinical examination objects.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising processing circuitry configured to:
   display, based on a medical examination data space having a plurality of dimensions corresponding to a plurality of data display formats respectively determined for a plurality of medical examination data, at least one of the plurality of medical examination data in the respective data display format along a first dimension; and perform space conversion on the medical examination data space, based on one medical examination data specified, as a conversion reference point, by an operator from the displayed at least one of the plurality of medical examination data and a second dimension specified, as a conversion direction, by the operator from the plurality of dimensions, to switch display of the medical examination data.

2. The medical information processing apparatus according to claim 1, wherein the medical examination data space is a space having three axes of a data type, time, and data interpretation classification as coordinate axes.

3. The medical information processing apparatus according to claim 1, wherein the medical examination data has a data structure corresponding to a coordinate axis of the medical examination data space.

4. The medical information processing apparatus according to claim 1, wherein the processing circuitry is configured to convert, as the space conversion, a first display state indicated by a point, line, or plane into a second display state indicated by another point, line, or plane, based on the medical examination data and the second dimension which are specified as the conversion reference and the conversion direction, respectively, in the first display state in the medical examination data space.

5. The medical information processing apparatus according to claim 1, wherein the processing circuitry is configured to perform, as the space conversion, rotation, parallel movement, magnification or reduction in the medical examination data space.

6. The medical information processing apparatus according to claim 1, wherein the processing circuitry is further configured to perform the space conversion on the basis of a specified conversion amount.

7. The medical information processing apparatus according to claim 1, wherein the medical examination data space further has a dimension corresponding to a subject.

8. The medical information processing apparatus according to claim 1, wherein the medical examination data and the medical examination data space are dynamically changed in accordance with a disease, an operator, or a medical examination phase.

9. The medical information processing apparatus according to claim 1, wherein the processing circuitry is further configured to display guide information indicating a position in the medical examination data space that corresponds to the respective data display format being displayed.

10. The medical information processing apparatus according to claim 9, wherein the processing circuitry is configured to display, as the guide information, a graphic indicating dimensions of the medical examination data space stereoscopically, and to display, on the graphic, information indicating a position that corresponds to the respective data display format being displayed.

11. The medical information processing apparatus according to claim 10, wherein the processing circuitry further receives, from an operator, an instruction to switch display of the medical examination data on the graphic.

12. A medical information processing method comprising:

displaying, based on a medical examination data space having a plurality of dimensions corresponding to a plurality of data display formats respectively determined for a plurality of medical examination data, at least one of the plurality of medical examination data in the respective data display format along a first dimension; and performing space conversion on the medical examination data space, based on one medical examination data specified, as a conversion reference point, by an operator from the displayed at least one of the plurality of medical examination data and a second dimension specified, as a conversion direction, by the operator from the plurality of dimensions, to switch display of the medical examination data.

13. The method as claimed in claim 12, wherein the medical examination data space is a space having three axes of a data type, time, and data interpretation classification as coordinate axes.

14. The method as claimed in claim 12, wherein the medical examination data has a data structure corresponding to a coordinate axis of the medical examination data space.

15. The method as claimed in claim 12, wherein performing the space conversion comprises converting a first display state indicated by a point, line, or plane into a second display state indicated by another point, line, or plane based on the medical examination data and the second dimension which are specified as the conversion reference and the conversion direction, respectively, in the first display state in the medical examination data space.

16. The method as claimed in claim 12, performing the space conversion comprises performing rotation, parallel movement, magnification or reduction in the medical examination data space.

17. The method as claimed in claim 12, performing the space conversion comprises performing the space conversion on the basis of a specified conversion amount.

\* \* \* \* \*